(12) United States Patent
Osaka et al.

(10) Patent No.: US 8,729,310 B2
(45) Date of Patent: May 20, 2014

(54) HALOGENATED DIARYLAMINE COMPOUND AND SYNTHESIS METHOD THEREOF

(75) Inventors: Harue Osaka, Kanagawa (JP); Hiroto Inoue, Kanagawa (JP)

(73) Assignee: Semiconductor Energy Laboratory Co., Ltd., Kanagawa-ken (JP)

(*) Notice: Subject to any disclaimer, the term of this patent is extended or adjusted under 35 U.S.C. 154(b) by 761 days.

(21) Appl. No.: 12/885,698

(22) Filed: Sep. 20, 2010

(65) Prior Publication Data

US 2011/0071317 A1 Mar. 24, 2011

(30) Foreign Application Priority Data

Sep. 22, 2009 (JP) ................. 2009-218290

(51) Int. Cl.
*C07C 211/00* (2006.01)
(52) U.S. Cl.
USPC ........................................................ 564/431
(58) Field of Classification Search
None
See application file for complete search history.

(56) References Cited

U.S. PATENT DOCUMENTS

| 2005/0260442 | A1 | 11/2005 | Yu et al. |
| 2007/0075632 | A1 | 4/2007 | Kawakami et al. |
| 2007/0152572 | A1 | 7/2007 | Kawakami et al. |
| 2007/0267969 | A1 | 11/2007 | Nakashima et al. |
| 2008/0268284 | A1 | 10/2008 | Kawakami et al. |
| 2010/0099890 | A1 | 4/2010 | Ogita et al. |

FOREIGN PATENT DOCUMENTS

JP 2007-015933 1/2007

OTHER PUBLICATIONS

Database Caplus Chemical Abstracts Service, Columbus, Ohio, US; Database Accession No. 2010:1161283, Abstract of JP 201020619, Shimizu et al., Sep. 16, 2010.*
Database Caplus Chemical Abstracts Service, Columbus, Ohio, US; Database Accession No. 2009:791541, Abstract of EP 2075309, Eum et al., Jul. 1, 2009.*

* cited by examiner

*Primary Examiner* — Karl J Puttlitz
(74) *Attorney, Agent, or Firm* — Nixon Peabody LLP; Jeffrey L. Costellia

(57) ABSTRACT

An object is to provide a new halogenated diarylamine compound serving as a source material for synthesis of a variety of diarylamine compounds and triarylamine compounds and a synthesis method of the new halogenated diarylamine compound. A halogenated diarylamine compound represented by the following general formula (G1) and a synthesis method thereof are provided. Note that a variety of diarylamine compounds and triarylamine compounds can be synthesized using the halogenated diarylamine compound represented by the following general formula (G1).

9 Claims, 23 Drawing Sheets para position (450)

para position (451)

HALOGENATED DIARYLAMINE COMPOUND AND SYNTHESIS METHOD THEREOF

BACKGROUND OF THE INVENTION

1. Field of the Invention

The present invention relates to a halogenated diarylamine compound and a synthesis method thereof.

2. Description of the Related Art

A display device using a light-emitting element in which an organic compound is used as a light-emitting substance (an organic EL element) has been developed rapidly as a next generation display device because it has advantages such as thinness, lightness in weight, high response speed, low power consumption, and flexibility. Although there have been various obstacles, technique has been improved such that organic EL televisions have become commercially available recently.

In an organic EL element, when voltage is applied between a pair of electrodes with a light-emitting layer provided therebetween, electrons and holes (carriers) injected from the pair of electrodes form a light-emitting substance in an excited state. When the carriers are recombined, the light-emitting substance in the exited state returns to a ground state, and light is emitted. The wavelength of light emitted from a light-emitting substance is peculiar to the light-emitting substance; thus, by using different types of organic compounds as light-emitting substances, light-emitting elements which exhibit a variety of wavelengths, i.e., a variety of colors can be obtained.

In the case of a display device which is expected to display images, such as a display, at least three colors of light, i.e., red, green, and blue are required in order to reproduce full-color images. To achieve this, for example, there are following methods: a method in which a light-emitting element emitting light with a light-emitting spectrum in a wide wavelength and a color filter are combined, a method in which a light-emitting element emitting light with a shorter wavelength than the wavelength of a desired color and a color conversion layer are combined, a method in which a light-emitting element emitting light with a desired wavelength is used. Among those three methods, the final one, i.e., a method in which a desired wavelength is obtained directly is preferable because loss in energy is small if the method is used.

This method in which a desired color is obtained directly is adapted to the organic EL televisions which have become commercially available; however, in addition to that method, a color filter is used in practice, and a micro cavity structure is employed for a light-emitting element in order to improve color purity. Organic EL televisions have got many advantages but are expected to provide high quality images as next generation televisions, and light-emitting elements exhibiting an appropriate emission color are required to live up to the expectation.

As described above, light emitted from a light-emitting substance is peculiar to the light-emitting substance. There are many measures to improve the color purity of organic EL televisions, but it is very difficult to obtain a light-emitting element which exhibits light emission of a favorable color and has other important properties such as lifetime, power consumption. The important properties such as lifetime, power consumption of the light-emitting element are not only dependent on a light-emitting substance, but also greatly dependent on layers other than a light-emitting layer, an element structure, properties and a relationship between a light-emitting substance and a host, or the like. Therefore, many kinds of materials for light-emitting elements are needed for the growth in this field. Accordingly, materials having various molecular structures for light-emitting elements have been proposed (for example, see Patent Document 1).

As a molecular structure of a material for transport of holes, a triarylamine compound is particularly often used. The structure thereof is thought to be electrochemically stable toward holes. Thus, a triarylamine compound is widely used as a hole-injection material, a hole-transport material, a light-emitting material, and a host material.

A triarylamine compound is combined with a variety of substituents, so that a compound which has a variety of properties can be obtained while the compound can maintain the above-mentioned property of a triarylamine compound. Therefore, a compound which is superior in a luminous quantum yield, a carrier-transport property, a carrier-injection property, an oxidation-reduction property, thermal stability, evaporativity, or solubility in a solvent; a compound which can provide a desired emission wavelength can be obtained; or a compound which is stable toward carrier recombination can be obtained.

Accordingly, a triarylamine compound having a desired aryl group and a simple and easy synthesis method thereof have been expected. In addition, a source material by which the synthesis of a triarylamine compound is simplified and a simpler synthesis method of the source material have been desired.

REFERENCE

[Patent Document 1] Japanese Published Patent Application No. 2007-15933

SUMMARY OF THE INVENTION

It is an object of one embodiment of the present invention to provide a new halogenated diarylamine compound serving as a source material for synthesis of a variety of diarylamine compounds and triarylamine compounds and to provide a synthesis method of the new halogenated diarylamine compound.

One embodiment of the present invention is a halogenated diarylamine compound represented by the following general formula (G1) and a synthesis method thereof. Note that a variety of diarylamine compounds and triarylamine compounds can be synthesized using the halogenated diarylamine compound.

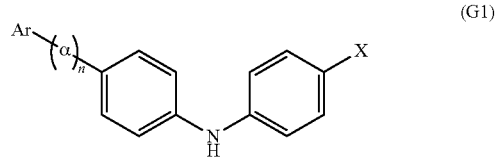

In the formula, Ar represents any of substituted or unsubstituted polycyclic aromatic hydrocarbon groups having 2 to 6 rings, and α represents a substituted or unsubstituted phenylene group. Further, n represents 0 or 1, and X represents any of chlorine, bromine, and iodine.

Note that examples of Ar in the general formula (G1) include a substituted or unsubstituted naphthyl group, a substituted or unsubstituted fluoranthenyl group, a substituted or unsubstituted fluorenyl group, a substituted or unsubstituted 9,9'-spirofluorenyl group, a substituted or unsubstituted phenanthryl group, a substituted or unsubstituted pyrenyl group, a substituted or unsubstituted triphenylenyl group, a substituted or unsubstituted chrysenyl group, a substituted or unsubstituted anthryl group, a substituted or unsubstituted pentacenyl group, and a substituted or unsubstituted tetracenyl group. Specifically, the following formulae (Ar-1) to (Ar-17) are given, for example.
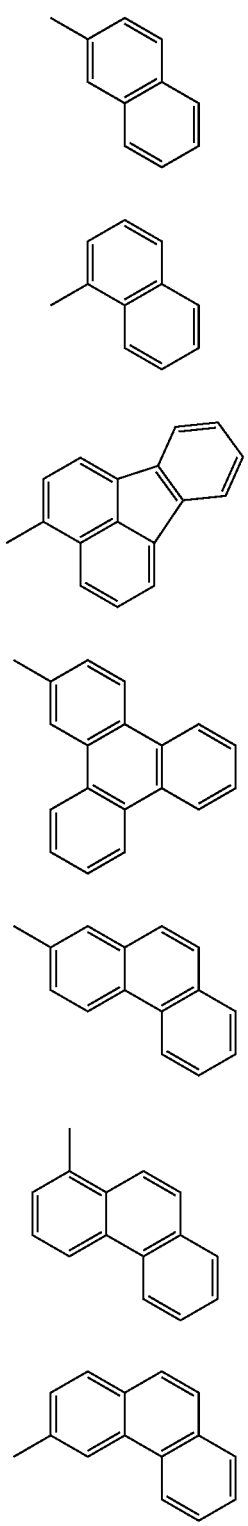
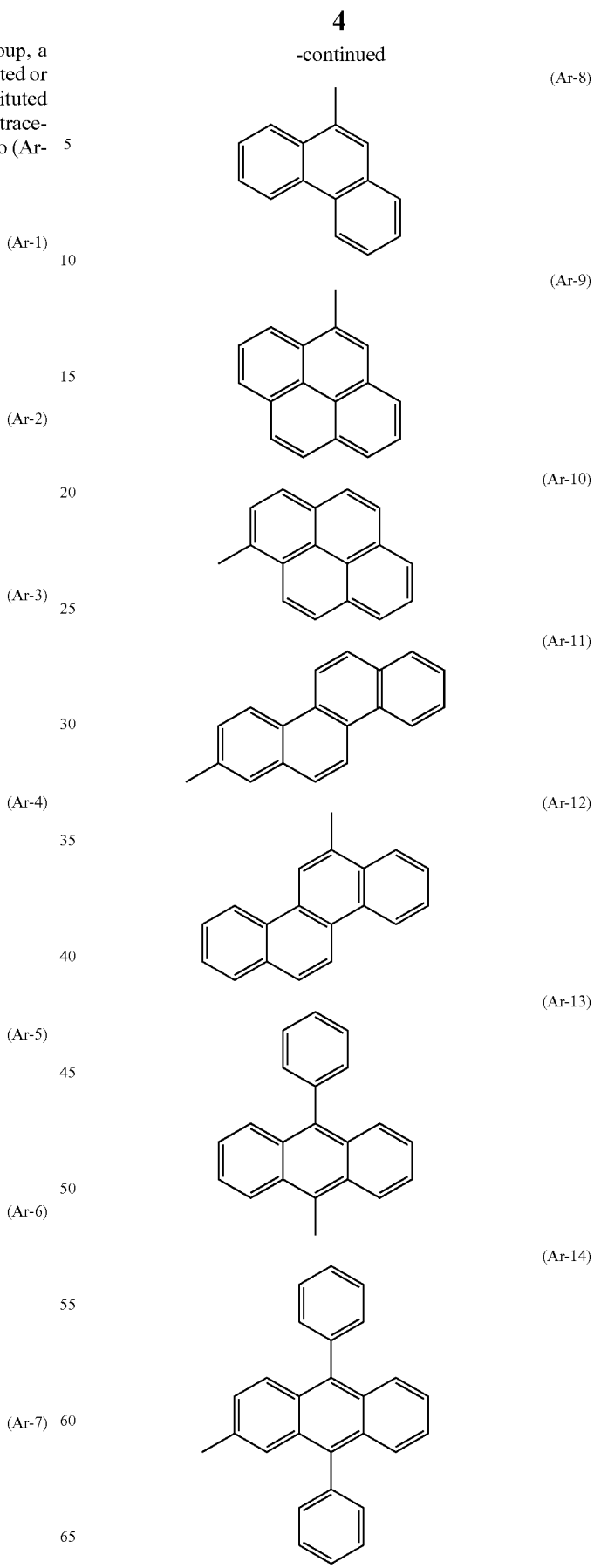

(Ar-15)
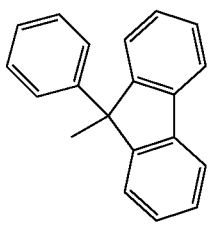

(Ar-16)
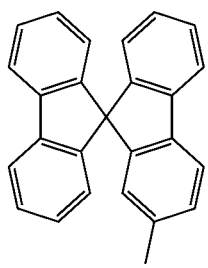

(Ar-17)
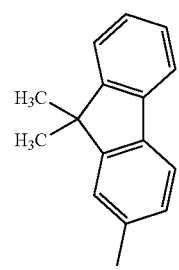

Further, as α in the general formula (G1), the following formulae (α-1) to (α-3) are given.

(α-1)
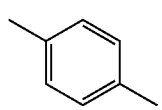

(α-2)
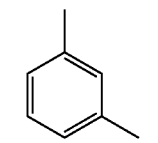

(α-3)
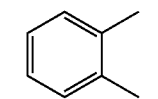

As a substituent of Ar or α in the general formula (G1), an alkyl group having 1 to 6 carbon atoms or an aryl group having 6 to 12 carbon atoms are given. For example, substituents represented by the following structural formulae (R-1) to (R-8) are given.

(R-1)
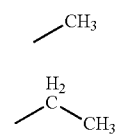

(R-2)
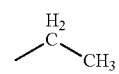

(R-3)
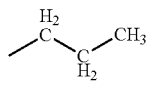

(R-4)
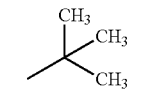

(R-5)
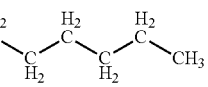

(R-6)
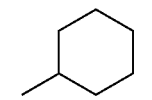

(R-7)
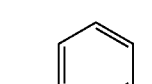

(R-8)
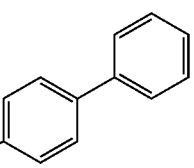

The halogenated diarylamine compound which is one embodiment of the present invention is preferably represented by any one of the following structural formulae (100) and (126).

(100)
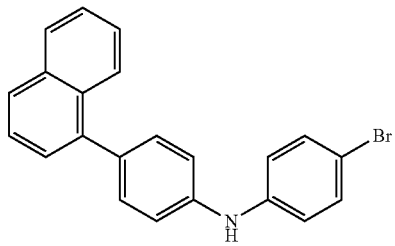

(126)
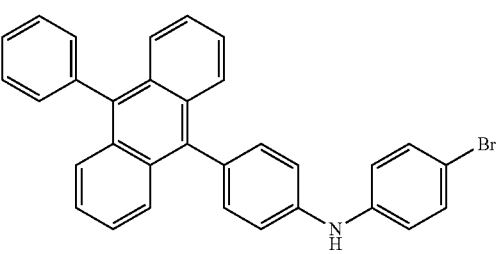

A secondary halogenated diarylamine compound (G1) which is one embodiment of the present invention is synthesized by halogenating a compound represented by the following general formula (G0) using any one of chlorine, bromine, and iodine. Specifically, as shown by the following general formula (A-3), the fourth position of phenylamine represented by the general formula (G0) is specifically-halogenated. Thus, the halogenated diarylamine compound can be obtained easily.

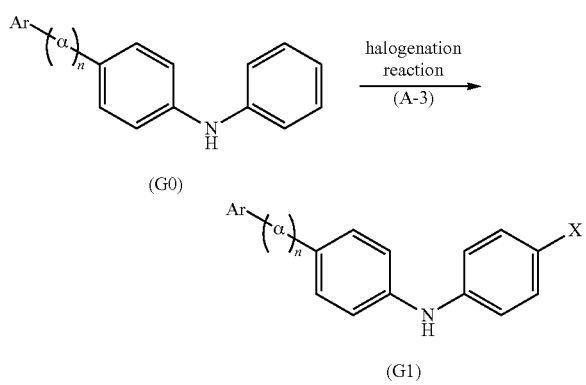

Further, according to one embodiment of the present invention, a variety of secondary diarylamine compounds and tertiary triarylamine compounds can be synthesized using the secondary halogenated diarylamine compound (G1).

One embodiment of the present invention is a light-emitting element using a triarylamine compound synthesized using the halogenated diarylamine compound (G1). The triarylamine compound has a favorable stability with respect to repetition of an oxidation state and a neutral state, and can be favorably used for a hole-injection layer, a hole-transport layer, and a light-emitting layer, which are included in an EL layer of the light-emitting element. In the light-emitting element of one embodiment of the present invention, the triarylamine compound is used for at least a layer of the EL layer. Note that one embodiment of the present invention includes a constitution in which the triarylamine compound is used for a light-emitting material in a light-emitting layer or a host material of the light-emitting material.

One embodiment of the present invention is a light-emitting device using a light-emitting element. The category of a light-emitting device includes a lighting device and an electronic appliance which each have a light-emitting device. Accordingly, a light-emitting device in this specification refers to an image display device, a light-emitting device, or a light source (including a lighting device). Further, the light-emitting device includes any of the following modules in its category: a module in which a connector such as a flexible printed circuit (FPC), a tape automated bonding (TAB) tape, or a tape carrier package (TCP) is attached to a light-emitting device; a module having a TAB tape or a TCP provided with a printed wiring board at the end thereof; and a module having an integrated circuit (IC) directly mounted over a light-emitting device by a chip on glass (COG) method.

One embodiment of the present invention can provide a new halogenated diarylamine compound and a synthesis method thereof. Further, one embodiment of the present invention can provide simpler synthesis methods of a variety of diarylamine compounds and triarylamine compounds by using the halogenated diarylamine compound synthesized by the above method as a source material.

BRIEF DESCRIPTION OF THE DRAWINGS

In the accompanying drawings:
FIGS. 21A and 2113 are diagrams illustrating the highest occupied molecular orbitals (HOMO) of structural formulae (426) and (428), respectively.

DETAILED DESCRIPTION OF THE INVENTION

Figure 1A:
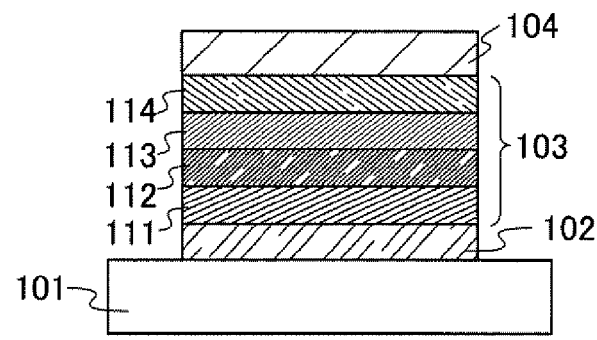
FIGS. 1A and 1B are conceptual diagrams of a light-emitting element according to one embodiment of the present invention.

One embodiment of the present invention is described below with reference to the accompanying drawings. Note that the present invention is not limited to the description given below, and modes and details of the present invention can be modified in various ways without departing from the spirit and scope of the present invention. Therefore, the invention should not be construed as being limited to the description in the following embodiment. Note that a common reference numeral refers to the same part or a part having a similar function throughout the drawings in the structure of the invention described below, and the description thereof is omitted.

Embodiment 1

One embodiment of the present invention is a halogenated diarylamine compound represented by the following general formula (G1). Note that a variety of diarylamine compounds and triarylamine compounds can be synthesized using the halogenated diarylamine compound.

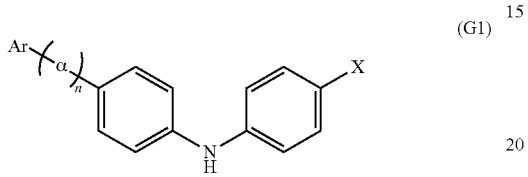
(G1)

In the formula, Ar represents any of substituted or unsubstituted polycyclic aromatic hydrocarbon groups having 2 to 6 rings, and a represents a substituted or unsubstituted phenylene group. Further, n represents 0 or 1, and X represents any of chlorine, bromine, and iodine.

In the general formula (G1), the following can be given as Ar: a substituted or unsubstituted naphthyl group; a substituted or unsubstituted fluoranthenyl group; a substituted or unsubstituted fluorenyl group; a substituted or unsubstituted 9,9'-spirofluorenyl group; a substituted or unsubstituted phenanthryl group; a substituted or unsubstituted pyrenyl group; a substituted or unsubstituted triphenylenyl group; a substituted or unsubstituted chrysenyl group; a substituted or unsubstituted anthryl group; a substituted or unsubstituted pentacenyl group; and a substituted or unsubstituted tetracenyl group. Specifically, the following formulae (Ar-1) to (Ar-17) are given, for example.

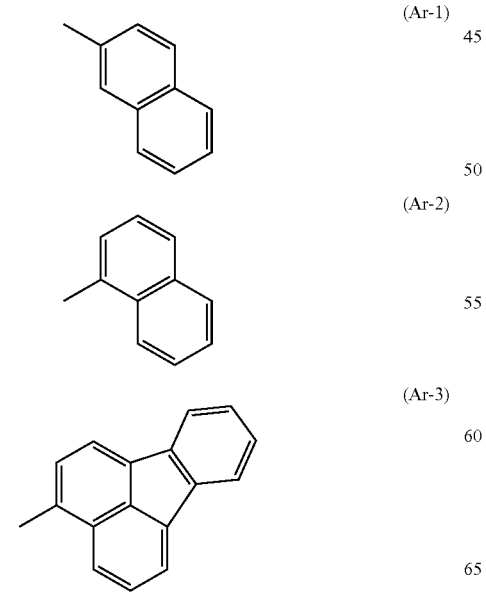

(Ar-1)
(Ar-2)
(Ar-3)

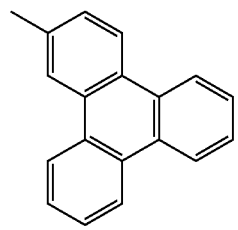
(Ar-4)

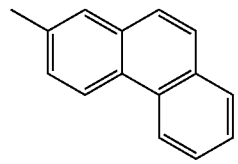
(Ar-5)

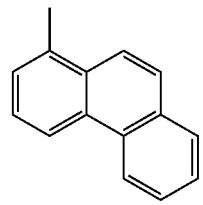
(Ar-6)

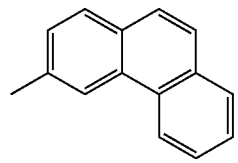
(Ar-7)

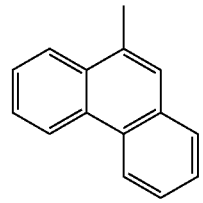
(Ar-8)

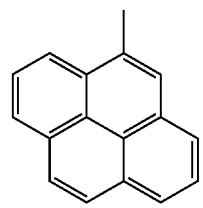
(Ar-9)

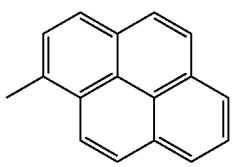
(Ar-10)

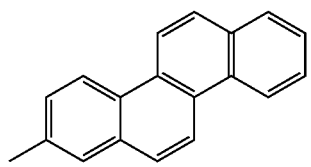
(Ar-11)

-continued (Ar-12)
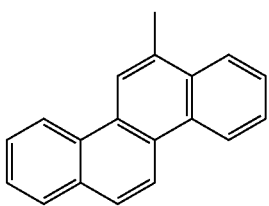

(Ar-13)
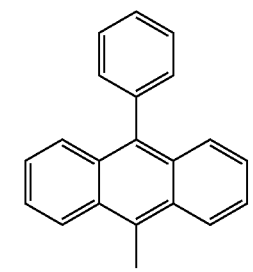

(Ar-14)
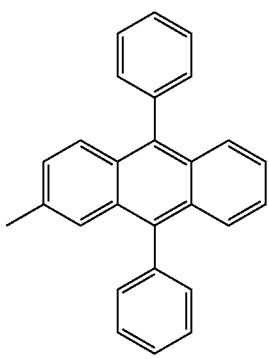

(Ar-15)
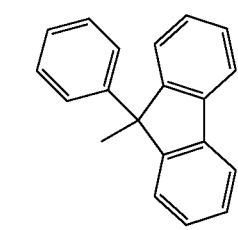

(Ar-16)
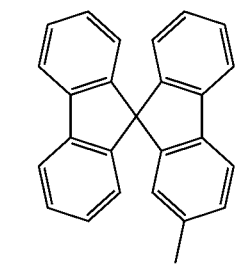

(Ar-17)
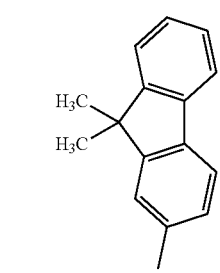

Further, as α in the general formula (G1), the following formulae (α-1) to (α-3) are given.

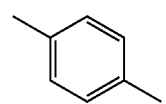
(α-1)

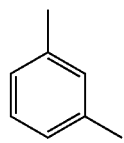
(α-2)

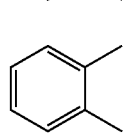
(α-3)

As substituents of Ar and α in the general formula (G1), an alkyl group having 1 to 6 carbon atoms and an aryl group having 6 to 12 carbon atoms are given. For example, substituents represented by the following structural formulae (R-1) to (R-8) are given.

(R-1)

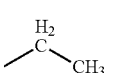
(R-2)

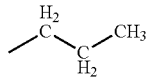
(R-3)

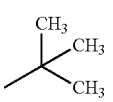
(R-4)

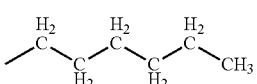
(R-5)

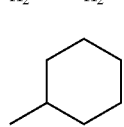
(R-6)

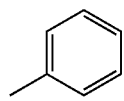
(R-7)

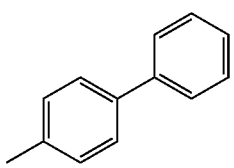
(R-8)

It is preferable to employ a halogenated diarylamine compound represented by the following structural formula (100)

or (126) as the halogenated diarylamine compound which is one embodiment of the present invention and represented by the general formula (G1).

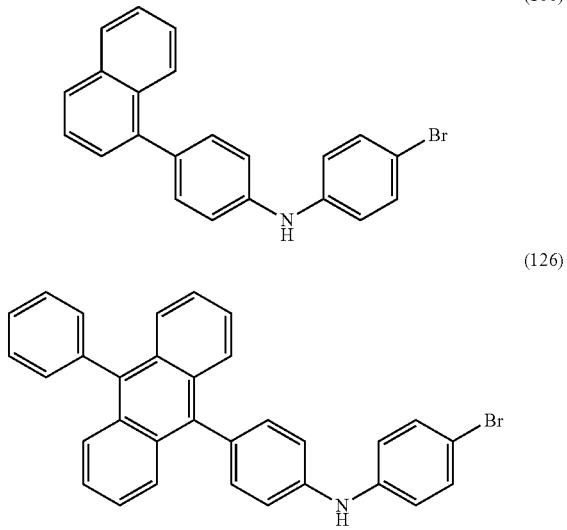

An example of an example of a synthesis method of the halogenated diarylamine compound of this embodiment which is represented by the general formula (G1) is described below.

《Synthesis Method 1 of Halogenated Diarylamine Compound》

The halogenated diarylamine compound represented by the following general formula (G1) can be synthesized by any of synthesis methods shown by synthesis schemes (A-1) to (A-3) below.

First, as in the synthesis scheme (A-1), an arylboronic acid compound (a1) and a dihalogenated arene compound (a2) are coupled, so that a halogenated arene compound (a3) is synthesized.

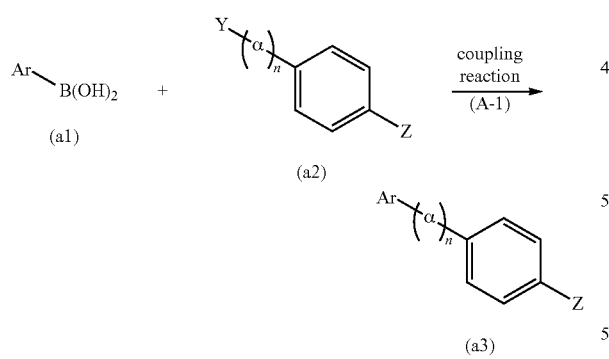

In the synthesis scheme (A-1), Ar represents any of substituted or unsubstituted polycyclic aromatic hydrocarbon groups having 2 to 6 rings, α represents a substituted or unsubstituted phenylene group, and n represents 0 or 1. Further, Y and Z each represent halogen; iodine, bromine, or chlorine is preferable as the halogen. In the case where Z is chlorine, Y is preferably bromine or iodine, since Y preferentially reacts with a boronic acid group. Alternatively, in the case where Z is bromine, Y is preferably iodine, since Y preferentially reacts with a boronic acid group.

A coupling reaction of an aryl compound including a halogen group and an aryl compound including a boronic acid (an arylboronic acid) as in the synthesis scheme (A-1) has a variety of reaction conditions. As an example thereof, a synthesis method using a metal catalyst in the presence of a base can be employed. The case of using, for example, a Suzuki-Miyaura reaction is described below.

In the synthesis scheme (A-1), a palladium catalyst can be used as the metal catalyst and a mixture of a palladium complex and a ligand thereof can be used as the palladium catalyst. As the palladium complex, palladium(II) acetate, tetrakis(triphenylphosphine)palladium(0), bis(triphenylphosphine)palladium(II) dichloride, and the like are given. As the ligand of the palladium complex, tri(ortho-tolyl)phosphine, triphenylphosphine, tricyclohexylphosphine, and the like are given. As a substance which can be used for the base, an organic base such as sodium tert-butoxide, an inorganic base such as potassium carbonate, and the like are given.

The reaction is preferably performed in a solution. As the solvent, a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like can be used. However, the catalyst, base, and solvent which can be used are not limited thereto.

Alternatively, in the coupling reaction shown in the synthesis scheme (A-1), an organoboron compound of an aryl compound, an aryl aluminum compound, an aryl zirconium compound, an aryl zinc compound, an aryl tin compound, or the like may be used as a reactive group, instead of an arylboronic acid. In addition, the reaction is preferably performed under an inert atmosphere of nitrogen, argon, or the like.

Next, as in a synthesis scheme (A-2), a halogenated arene compound (a3) and aniline (a4) are coupled, so that a diarylamine compound (G0) is synthesized.

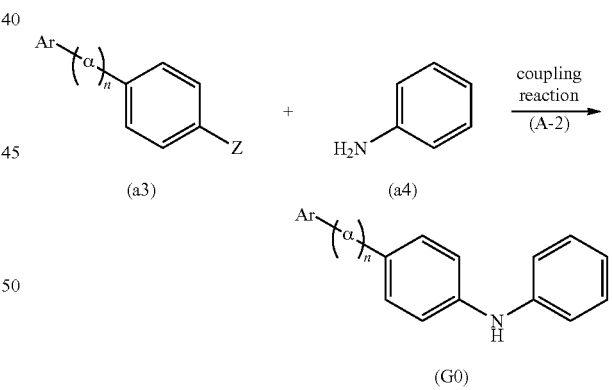

In the synthesis scheme (A-2), Ar represents any of substituted or unsubstituted polycyclic aromatic hydrocarbon groups having 2 to 6 rings, α represents a substituted or unsubstituted phenylene group, and n represents 0 or 1. Further, Z represents halogen; and iodine, bromine, or chlorine is preferable as the halogen.

A coupling reaction of an aryl compound including a halogen group and an aryl compound including amine (a primary arylamine compound or a secondary arylamine compound) as in the synthesis scheme (A-2) has a variety of reaction conditions. As an example thereof, a synthesis method using a metal catalyst in the presence of a base can be employed. As an example of this synthesis method, the case of using a Buchwald-Hartwig reaction is described below.

In the synthesis scheme (A-2), a palladium catalyst can be used as the metal catalyst and a mixture of a palladium complex and a ligand thereof can be used as the palladium catalyst. As the palladium complex, bis(dibenzylideneacetone) palladium(0), palladium(II) acetate, and the like are given. As a ligand of the palladium complex, tri(tert-butyl)phosphine, tri(n-hexyl)phosphine, tricyclohexylphosphine, 1,1-bis (diphenylphosphino)ferrocene (abbreviation: DPPF), and the like are given. As a substance which can be used for the base, an organic base such as sodium tert-butoxide, an inorganic base such as potassium carbonate, and the like are given. The reaction is preferably performed in a solution, and toluene, xylene, benzene, and the like are given as a solvent that can be used in the reaction. However, the catalyst, base, and solvent which can be used are not limited thereto. In addition, the reaction is preferably performed under an inert atmosphere of nitrogen, argon, or the like.

As another synthesis method of this reaction, the case of using an Ullmann reaction is described. A copper catalyst can be used as the metal catalyst, and copper iodide (I) and copper acetate (II) are given as the copper catalyst. As an example of a substance which can be used for the base, an inorganic base such as potassium carbonate is given. The reaction is preferably performed in a solution, and 1,3-dimethyl-3,4,5,6-tetrahydro-2(1H)-pyrimidinone (abbreviation: DMPU), toluene, xylene, benzene, and the like are given as a solvent that can be used. However, the catalyst, base, and solvent which can be used are not limited thereto. In addition, the reaction is preferably performed under an inert atmosphere of nitrogen, argon, or the like.

Note that a solvent having a high boiling point such as DMPU or xylene is preferably used because, by an Ullmann reaction, a desired substance can be obtained in a shorter time and in a higher yield when the reaction temperature is higher than or equal to 100° C. In particular. DMPU is more preferable because it is more preferable that the reaction temperature is higher than or equal to 150° C.

Next, as in a synthesis scheme (A-3), the diarylamine compound (G0) is halogenated, so that a secondary halogenated diarylamine compound represented by the general formula (G1) can be synthesized.

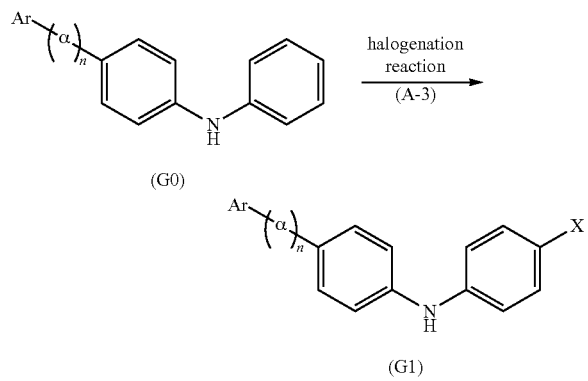

In the synthesis scheme (A-3), Ar represents any of substituted or unsubstituted polycyclic aromatic hydrocarbon groups having 2 to 6 rings, a represents a substituted or unsubstituted phenylene group, and n represents 0 or 1. Further, X represents any of chlorine, bromine, and iodine.

A halogenation reaction in the synthesis scheme (A-3) has a variety of reaction conditions. For example, a reaction in which a halogenating agent is used in the presence of a polar solvent can be used. As the halogenating agent, N-bromosuccinimide (abbreviation: NBS), N-iodosuccinimide (abbreviation: NIS), bromine, iodine, potassium iodide, or the like can be used. As the halogenating agent, the use of bromide is preferable because synthesis can be performed at low cost. It is preferable to use iodide as the halogenating agent. This is because, in the case where a reaction using the generated compound (iodide) as a source material is performed, in the generated iodide, a portion which is replaced by iodine is highly active, so that the reaction proceeds more easily.

In the synthesis scheme (A-3), the para position of phenylamine represented by the general formula (G0) is selectively halogenated, so that the halogenated diarylamine compound represented by the general formula (G1) can be easily synthesized and purified, which is preferable.

Note that a reaction that passes through the synthesis scheme (A-2) and the synthesis scheme (A-3) is preferable, since reaction sites are localized and a side reaction hardly occurs, reading to simple and easy purification and a high yield.

《Synthesis Method 2 of Halogenated Diarylamine Compound》

As in the following synthesis scheme (A-4), the halogenated arene compound (a3) obtained through the synthesis scheme (A-1) and halogenated aniline (a5) are coupled, so that the halogenated diarylamine compound represented by the general formula (G1) can be synthesized.

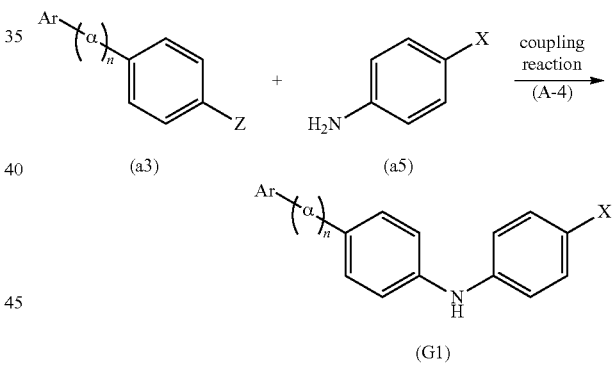

In the synthesis scheme (A-4), Ar represents any of substituted or unsubstituted polycyclic aromatic hydrocarbon groups having 2 to 6 rings, a represents a substituted or unsubstituted phenylene group, and n represents 0 or 1. Further, Z represents halogen; iodine, bromine, or chlorine is preferable as the halogen. Furthermore, X represents any of chlorine, bromine, and iodine.

A coupling reaction of an aryl compound including a halogen group and an aryl compound including amine (a primary arylamine compound or a secondary arylamine compound) as in the synthesis scheme (A-4) has a variety of reaction conditions. As an example thereof, a synthesis method using a metal catalyst in the presence of a base (e.g., the Buchwald-Hartwig reaction or the Ullmann reaction mentioned in the description of the synthesis scheme (A-2)) can be employed.

Note that the reaction that passes through the synthesis scheme (A-4) has a small number of reaction steps, which is simple and favorable.

《Synthesis Method 3 of Halogenated Diarylamine Compound》

The diarylamine compound represented by the general formula (G0) shown in the above synthesis scheme (A-2) can be synthesized by coupling an arylboronic acid compound (b1) and halogenated didiphenylamine (b2) as shown in the following synthesis scheme (B-1).

In the synthesis scheme (B-1), Ar represents any of substituted or unsubstituted polycyclic aromatic hydrocarbon groups having 2 to 6 rings, α represents a substituted or unsubstituted phenylene group, and n represents 0 or 1. Further, Y represents halogen; iodine, bromine, or chlorine is preferable as the halogen.

A coupling reaction of an aryl compound including a halogen group and an aryl compound including a boronic acid (an arylboronic acid) as in the synthesis scheme (B-1) has a variety of reaction conditions. As an example thereof, a synthesis method using a metal catalyst in the presence of a base (e.g., the Suzuki-Miyaura reaction described in the synthesis scheme (A-1)) can be employed.

After the diarylamine compound (G0) is obtained, the diarylamine compound (G0) is halogenated as in the synthesis scheme (A-3), so that the halogenated diarylamine compound represented by the general formula (G1) can be synthesized.

Note that the reaction that passes through the synthesis scheme (B-1) has a small number of reaction steps, which is preferable.

As described above, there are various synthesis methods of the halogenated diarylamine compound represented by the general formula (G1).

Specific examples of structural formulae of the halogenated diarylamine compound which is one embodiment of the present invention are shown below (structural formulae (100) to (133), (150) to (167), (200) to (217), (250) to (267), and (270) to (275)). Note that the present invention is not limited thereto.

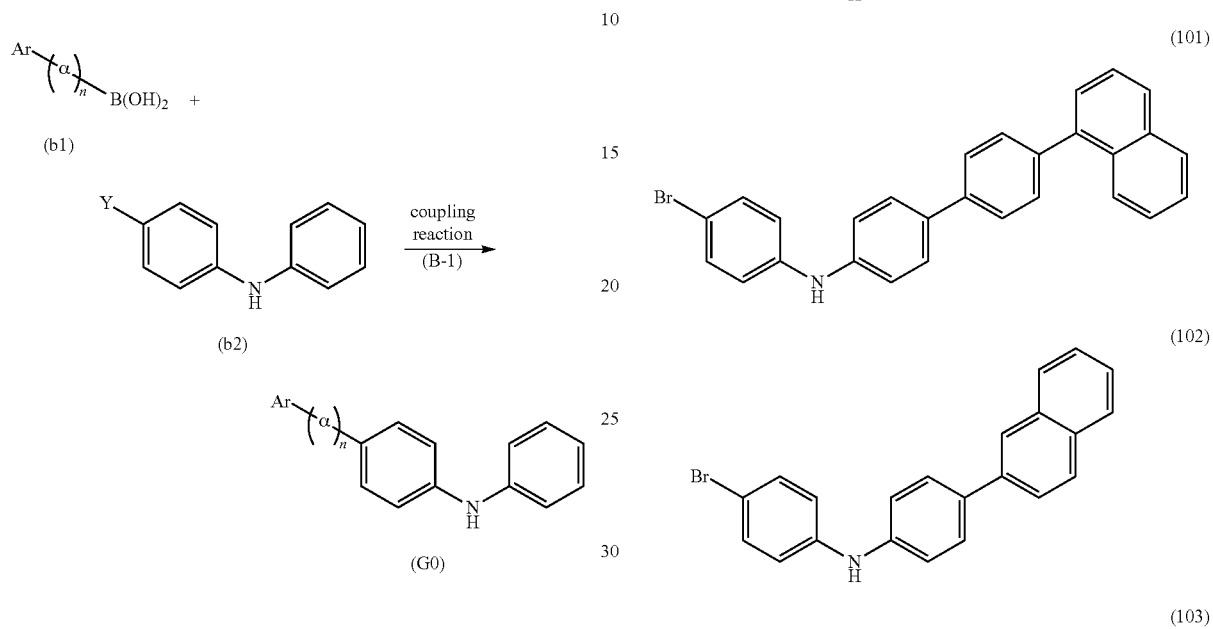

(106)
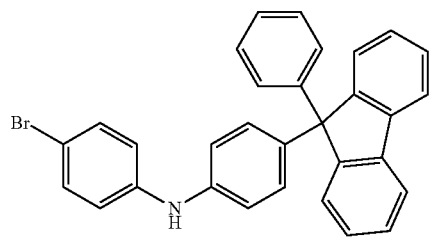
(107)
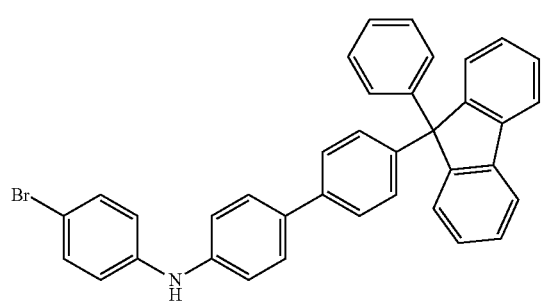
(108)
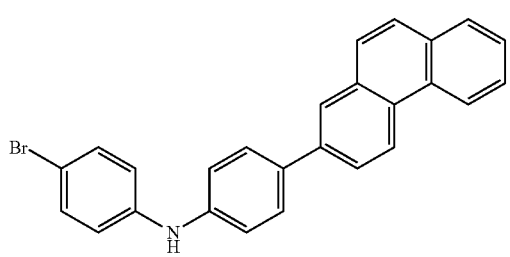
(109)
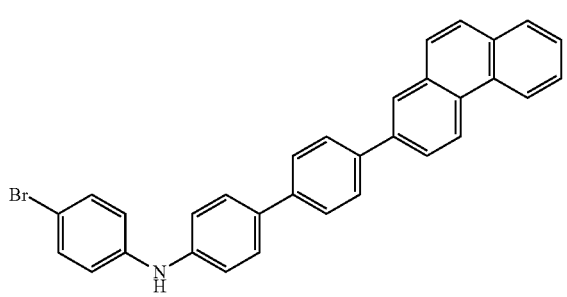
(110)
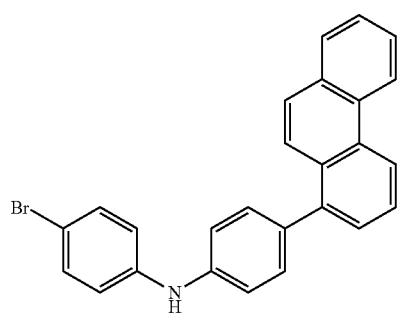
(111)
(112)
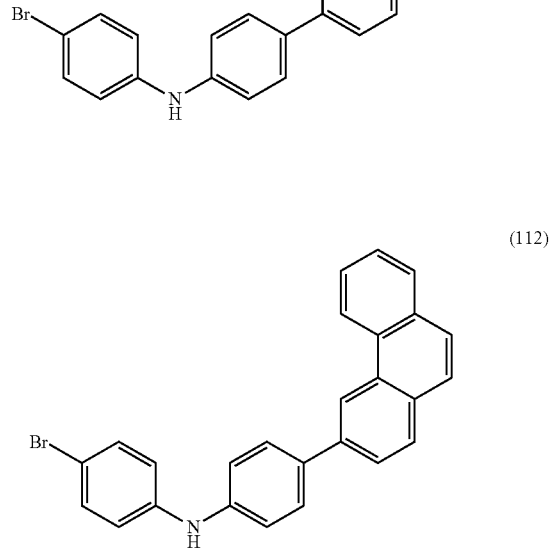
(113)
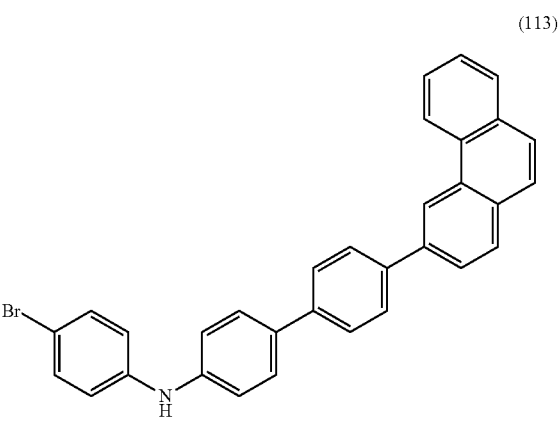
(114)
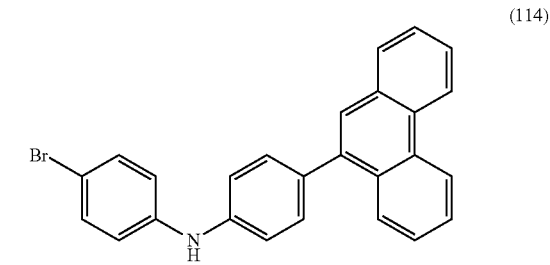

(115)
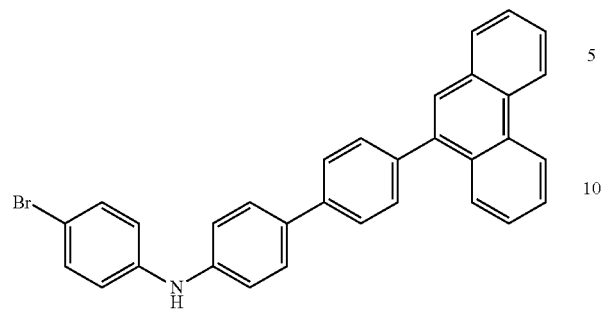
(116)
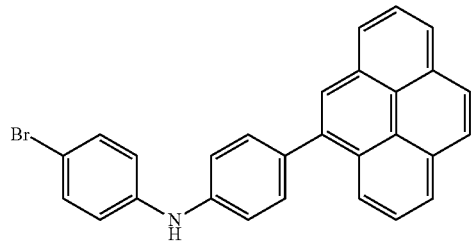
(117)
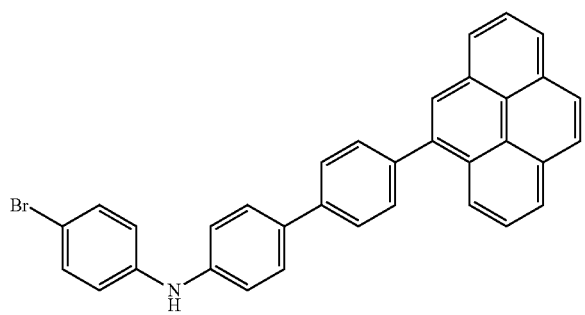
(118)
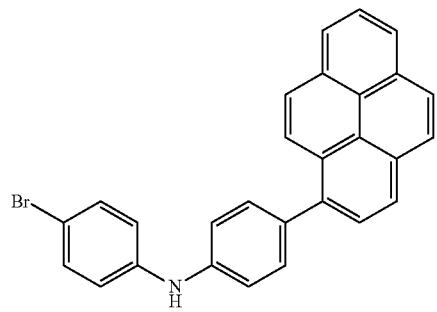
(119)
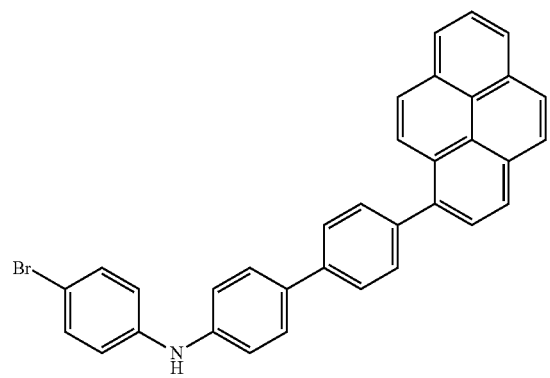
(120)
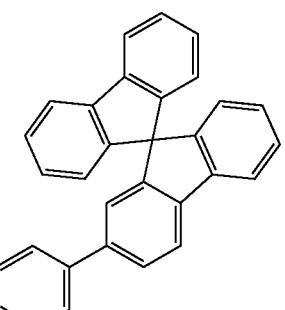
(121)
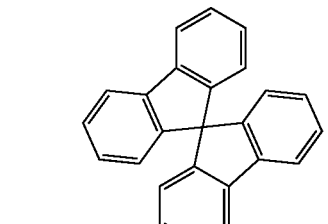
(122)
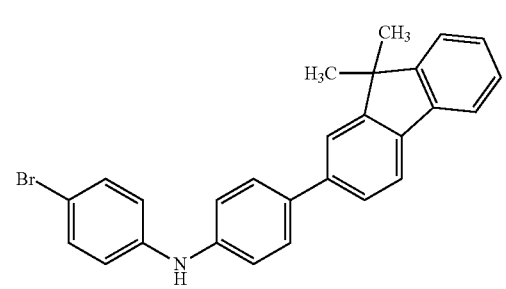
(123)
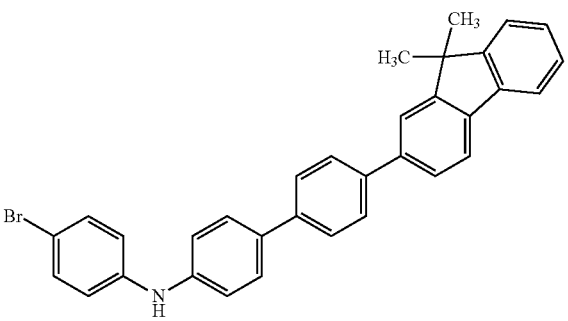

(124)
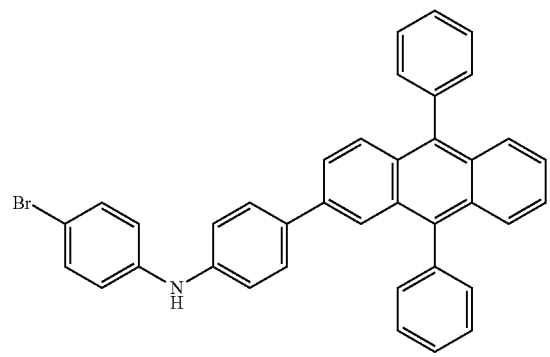
(125)
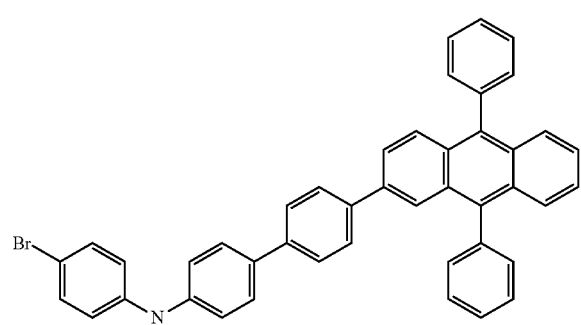
(126)
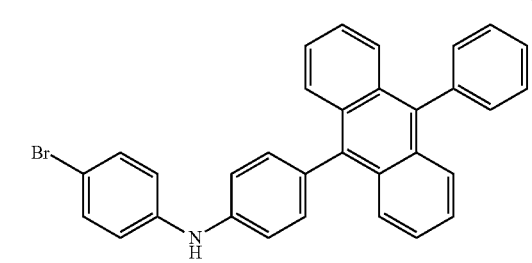
(127)
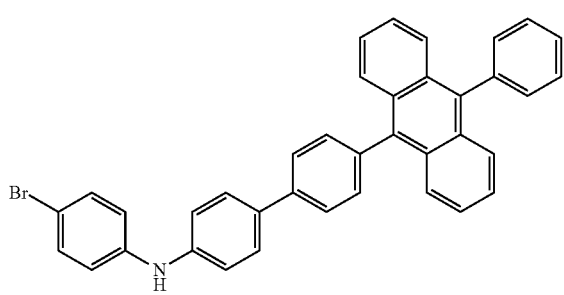
(128)
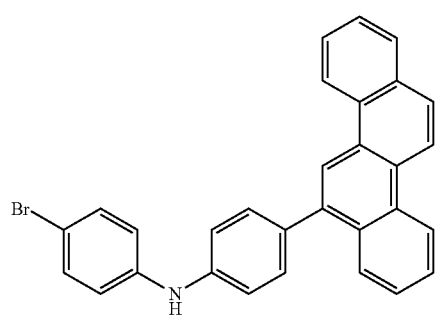
(129)
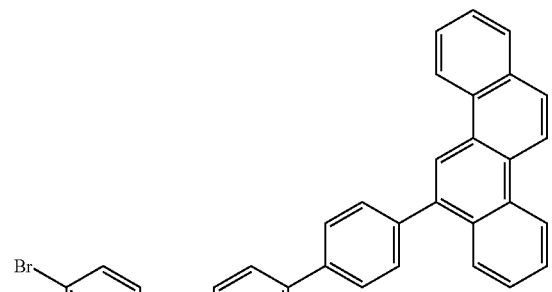
(130)
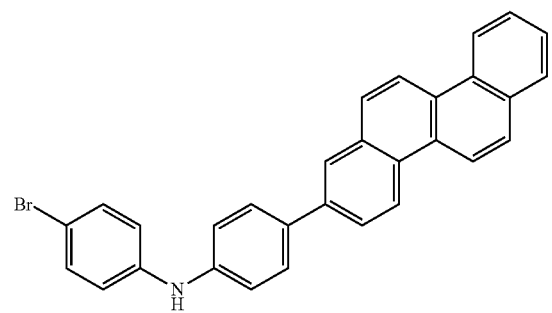
(131)
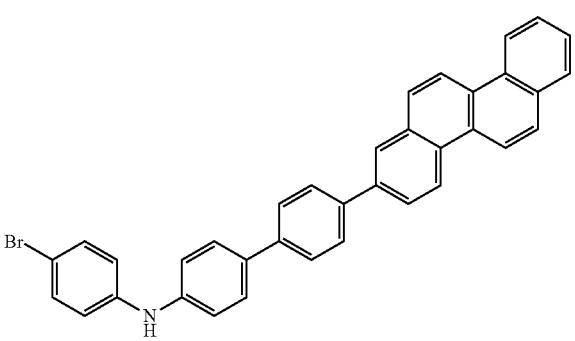
(132)
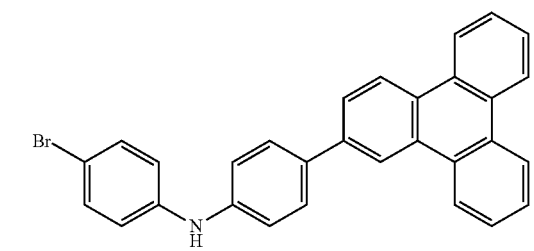

-continued
(133)
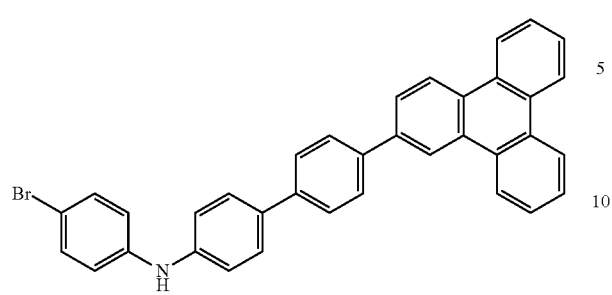
(150)
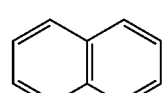
(151)
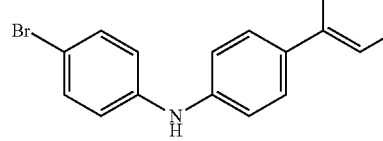
(152)
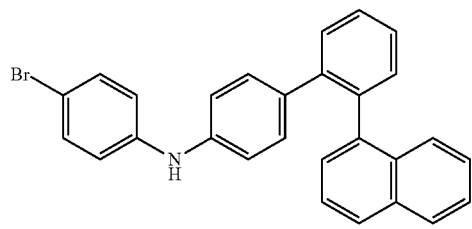
(153)
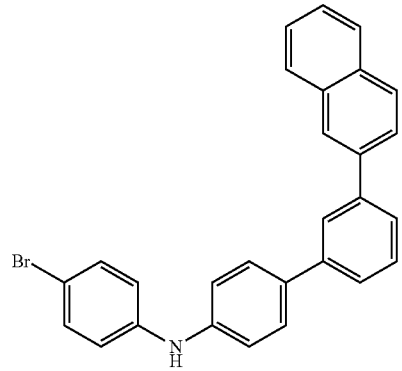
-continued
(154)
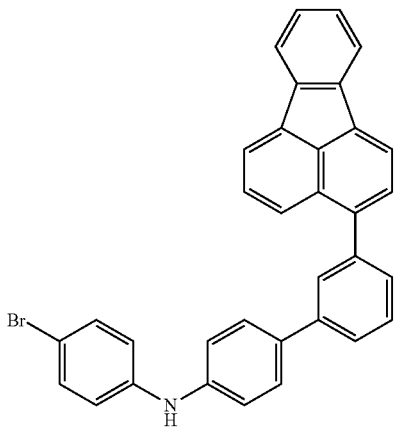
(155)
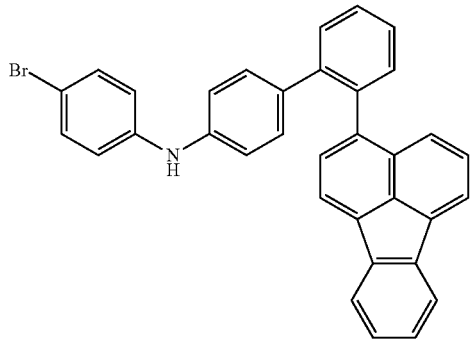
(156)
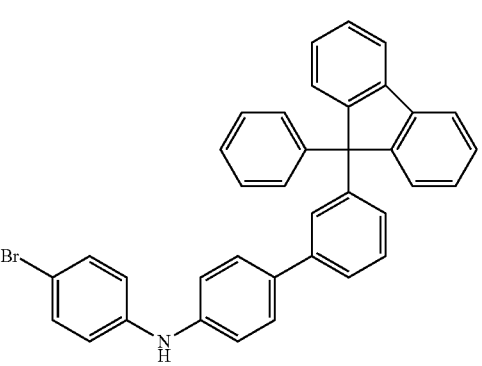
(157)
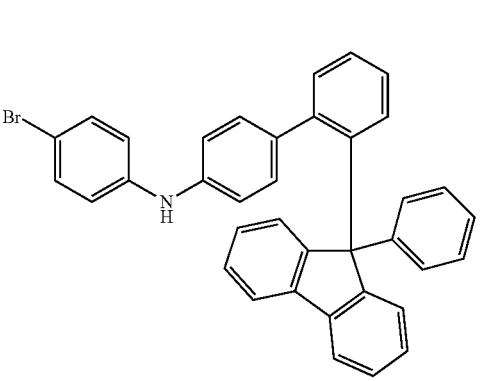

(158)
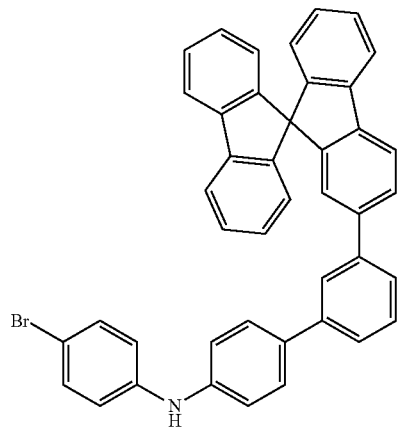
(159)
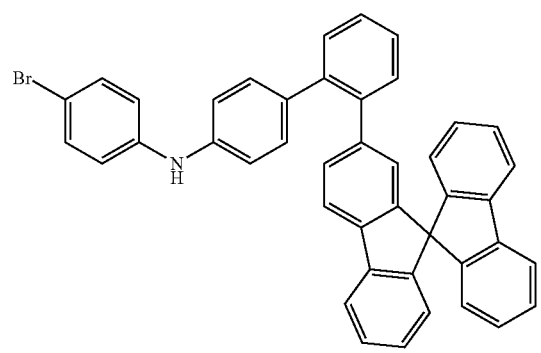
(160)
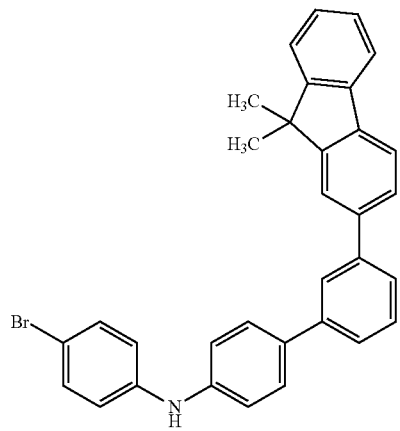
(161)
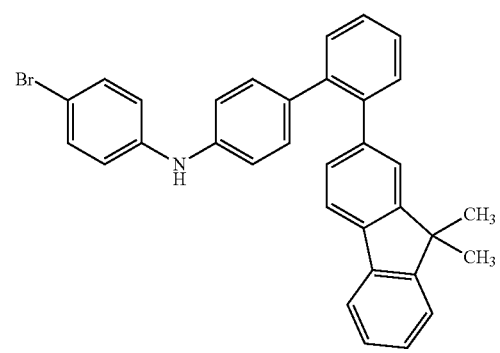
(162)
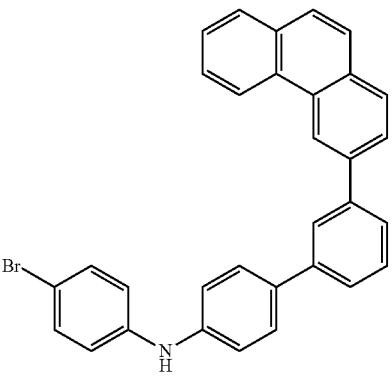
(163)
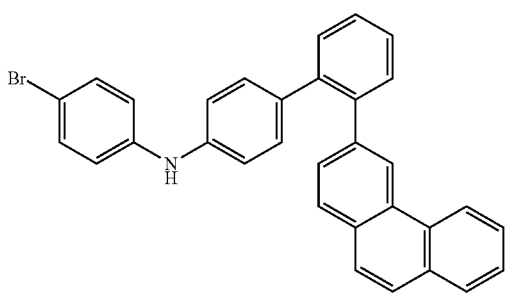
(164)
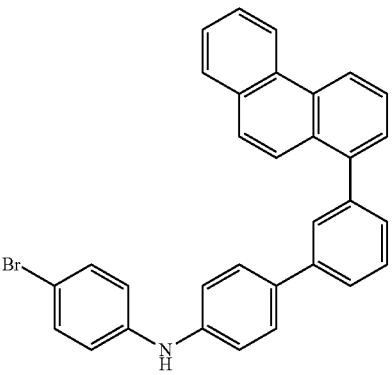
(165)
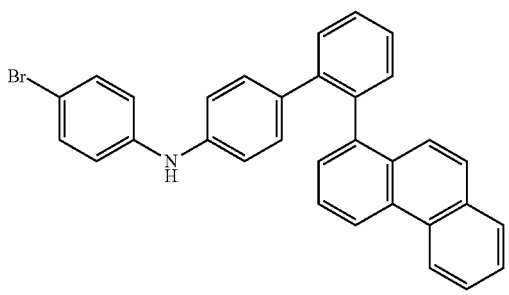

(166)
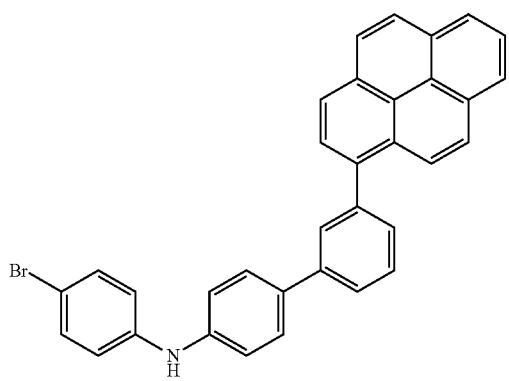
(167)
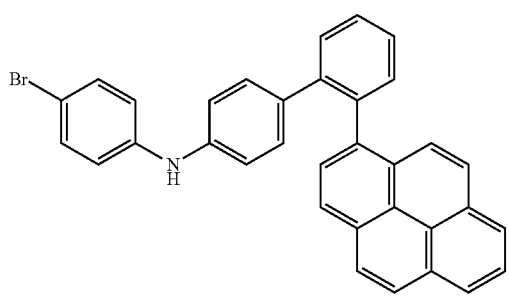
(200)
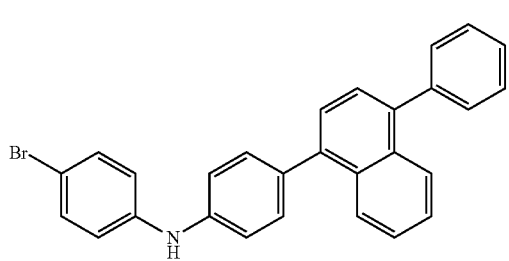
(201)
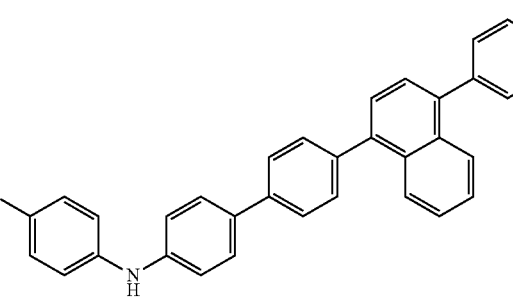
(202)
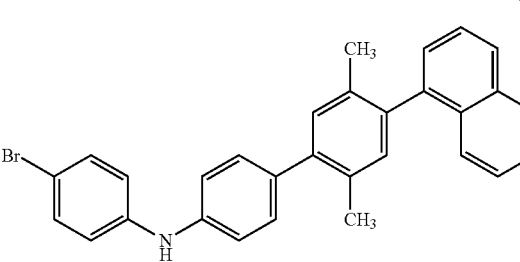
(203)
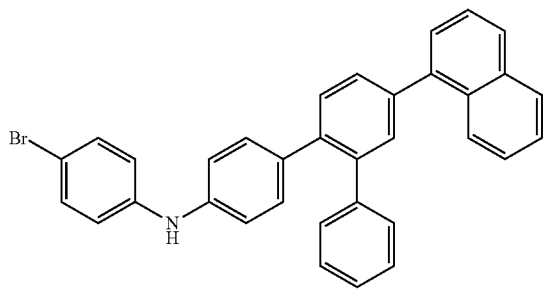
(204)
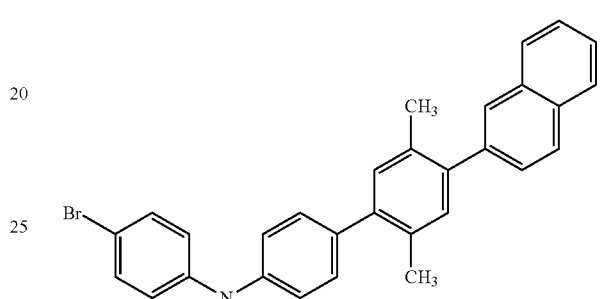
(205)
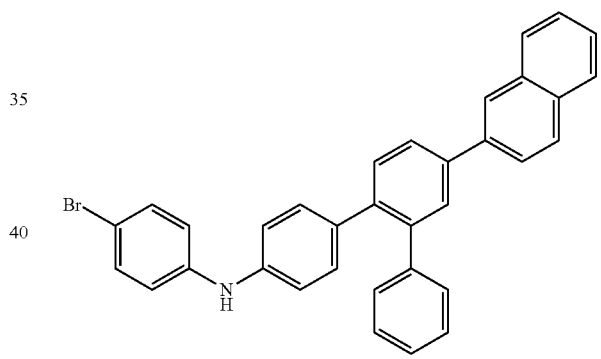
(206)
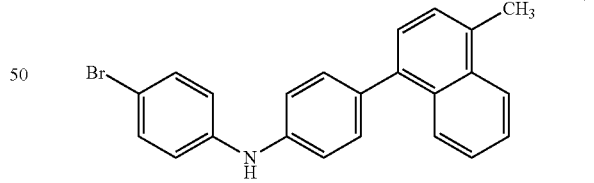
(207)
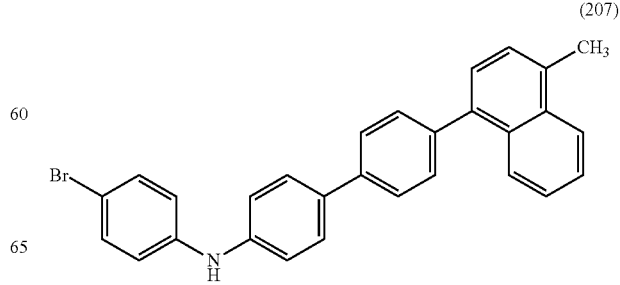

-continued
(208)
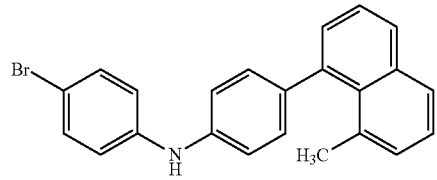
(209)
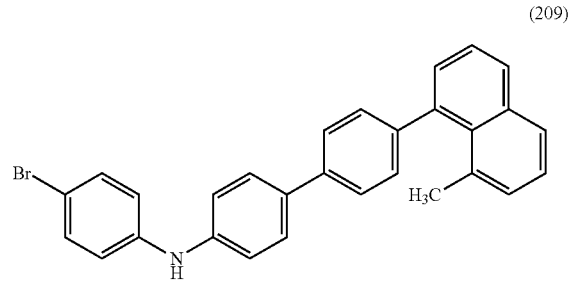
(210)
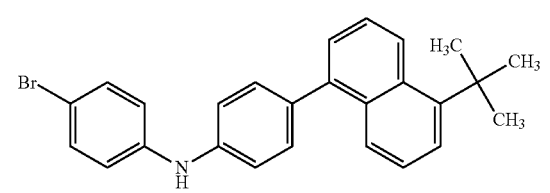
(211)
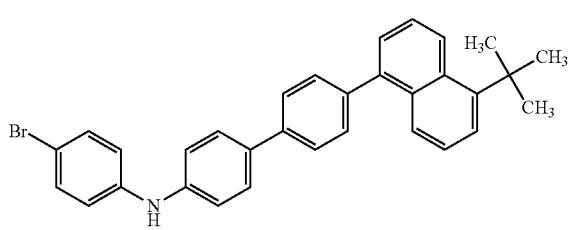
(212)
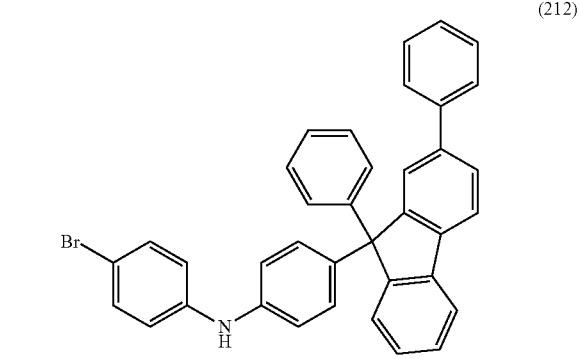
-continued
(213)
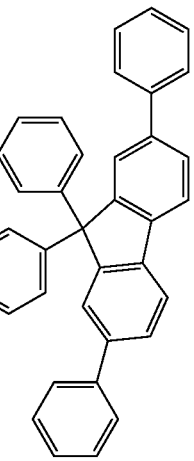
(214)
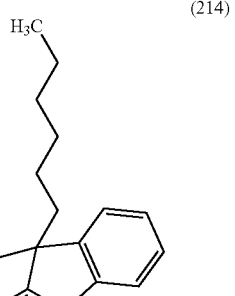
(215)
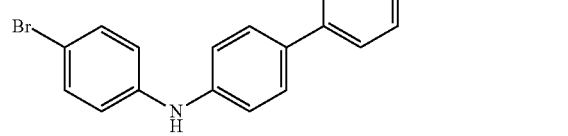

(216)
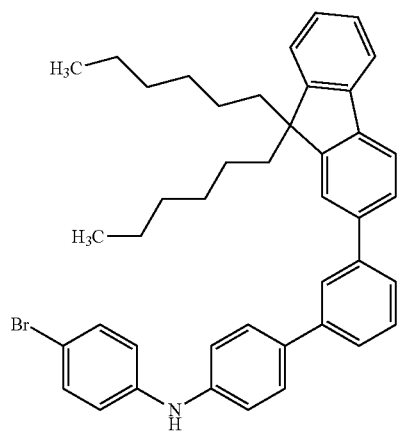
(217)
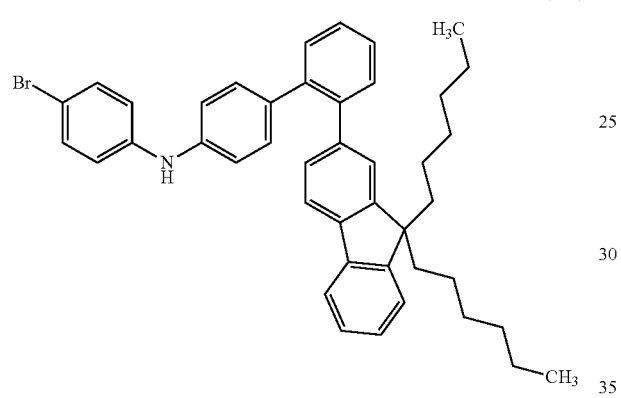
(250)
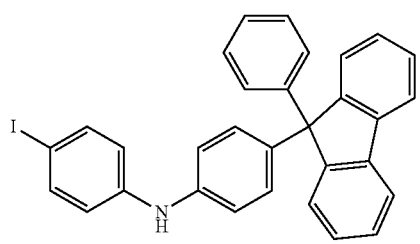
(251)
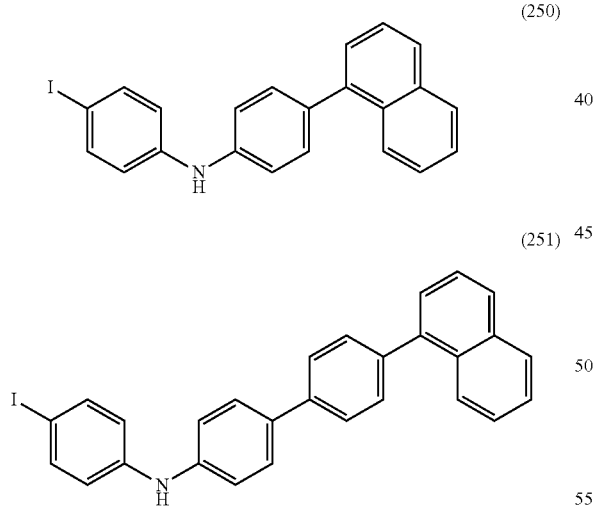
(252)
(253)
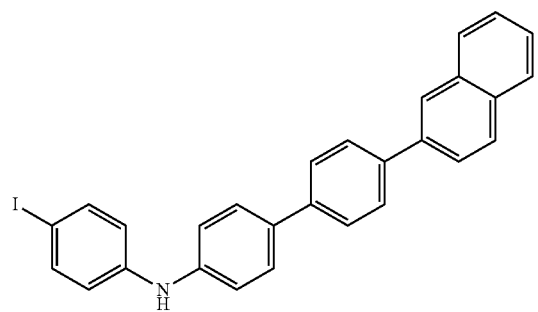
(254)
(255)
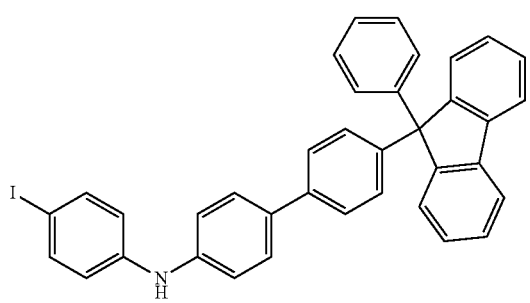
(256)
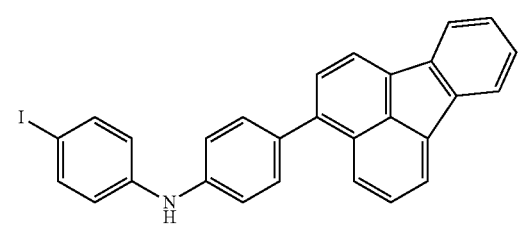
(257)
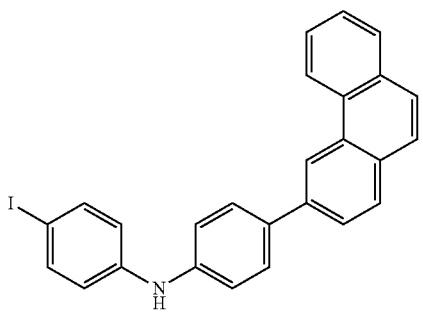

-continued
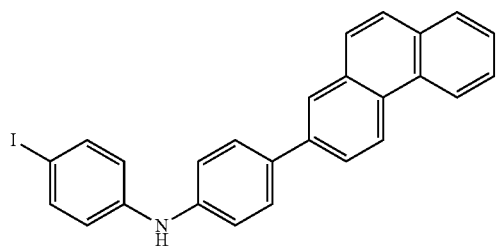
(258)
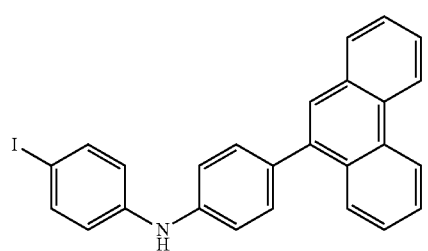
(259)
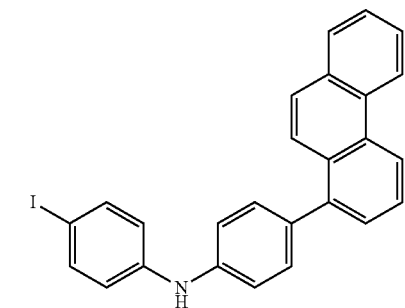
(260)
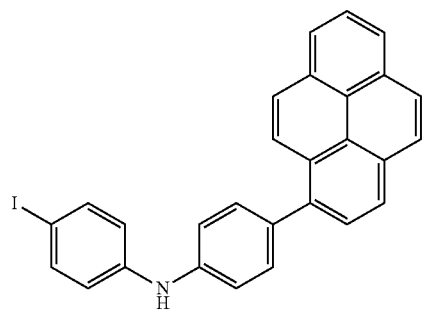
(261)
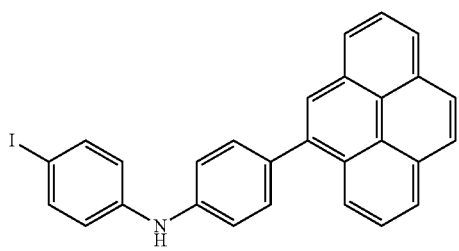
(262)
-continued
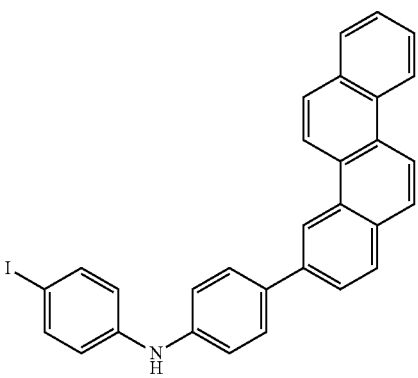
(263)
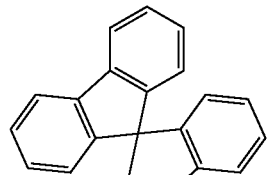
(264)
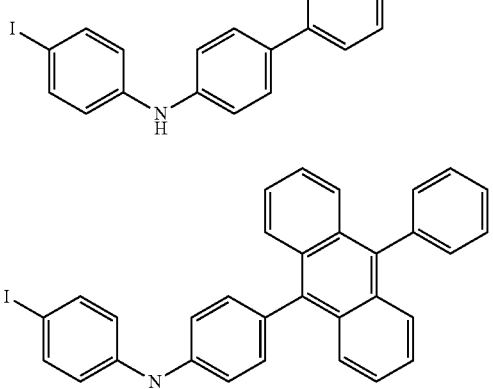
(265)
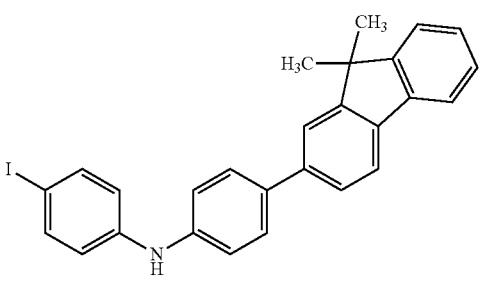
(266)
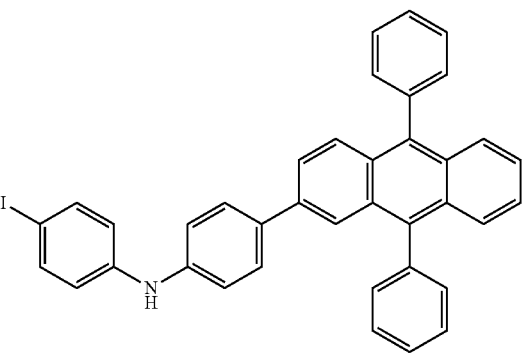
(267)

-continued

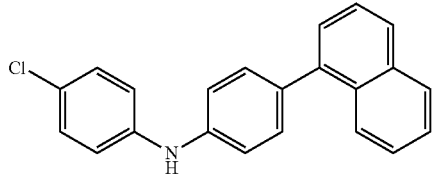 (270)

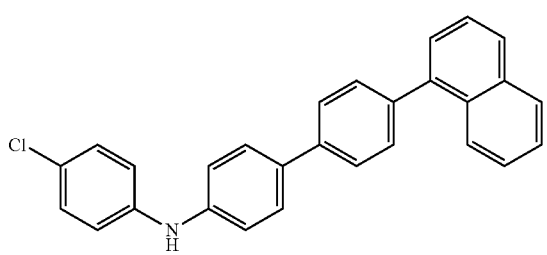 (271)

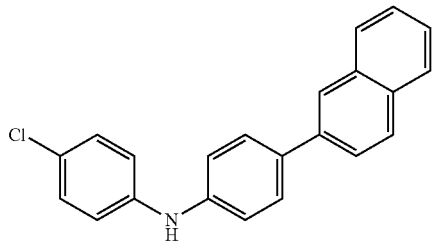 (272)

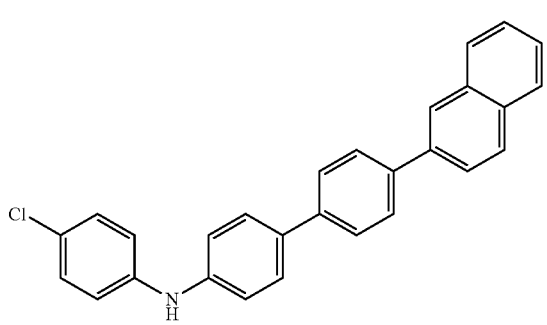 (273)

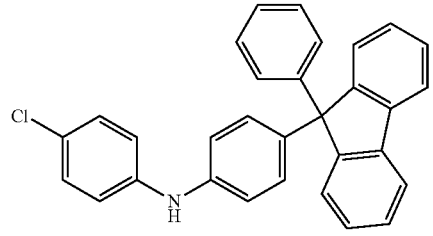 (274)

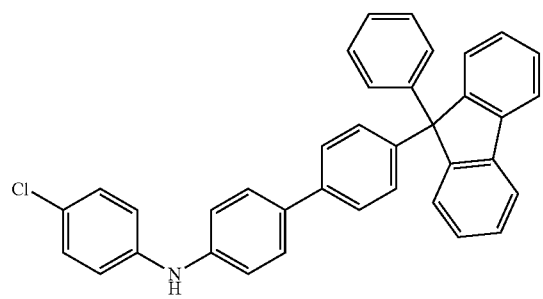 (275)

The structures, methods, and the like described in this embodiment can be combined as appropriate with any of the structures, methods, and the like described in the other embodiments.

Embodiment 2

In this embodiment, a synthesis method of a diarylamine compound using, as a source material, the halogenated diarylamine compound which is one embodiment of the present invention and described in Embodiment 1 is described. Further, a synthesis method of a triarylamine compound using the diarylamine compound as a source material is described.

《Synthesis Method of Diarylamine Compound》

For example, as shown in the following synthesis scheme (C-1), the secondary halogenated diarylamine compound represented by the general formula (G1) which is one embodiment of the present invention and an arylboronic acid compound (c1) are coupled, whereby a secondary diarylamine compound represented by a general formula (G2) can be obtained.

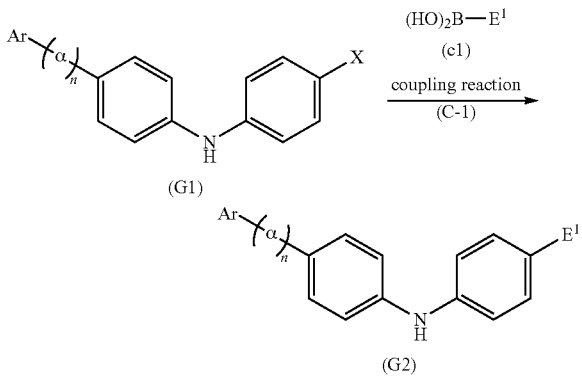

In the synthesis scheme (C-1), Ar represents any of substituted or unsubstituted polycyclic aromatic hydrocarbon groups having 2 to 6 rings, α represents a substituted or unsubstituted phenylene group, and n represents 0 or 1. Further, X represents any of chlorine, bromine, and iodine. Furthermore, $E^1$ represents an aryl group and the aryl group includes a heteroaryl group.

A coupling reaction in the synthesis scheme (C-1) has a variety of reaction conditions. As an example thereof, a synthesis method using a metal catalyst in the presence of a base can be employed. As a synthesis reaction, the Suzuki-Miyaura reaction, or the like can be employed. The detailed description of the reaction conditions is made in Embodiment 1, and this reaction can also be performed as in Embodiment 1; thus, a repeated description is omitted here.

According to the synthesis scheme (C-1), Ar and E' can be different substituents in the general formula (G2), which is preferable because various compounds can be synthesized. Ar and E' can be the same substituents.

《Synthesis Method of Triarylamine Compound》

For example, as shown in the following synthesis scheme (C-2), the secondary diarylamine compound represented by the general formula (G2) and a halogenated arene compound (c2) are coupled, whereby a tertiary triarylamine compound represented by a general formula (G3) can be obtained.

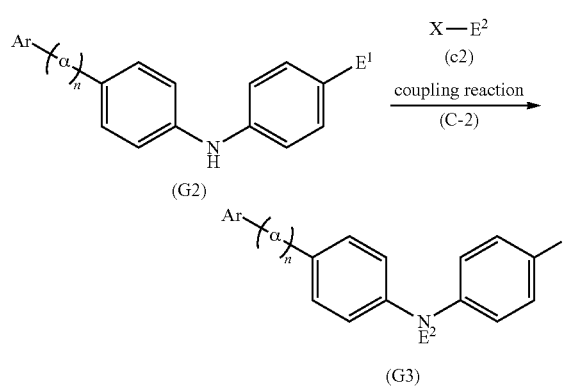

In the synthesis scheme (C-2), Ar represents any of substituted or unsubstituted polycyclic aromatic hydrocarbon groups having 2 to 6 rings, α represents a substituted or unsubstituted phenylene group, and n represents 0 or 1. Further, X represents any of chlorine, bromine, and iodine. Furthermore, $E^1$ and $E^2$ independently represent an aryl group and the aryl group includes a heteroaryl group. In the case where the heteroaryl group has an electron-transport property, the obtained tertiary triarylamine compound (G3) serves as a bipolar material that transports both electrons and holes, which is suitable for a light-emitting material or a host material thereof.

A coupling reaction in the synthesis scheme (C-2) has a variety of reaction conditions. As an example thereof, a synthesis method using a metal catalyst in the presence of a base can be employed. As a synthesis reaction, the Buchwald-Hartwig reaction or the Ullmann reaction can be employed. The detailed description of the reaction conditions is made in Embodiment 1, and this reaction can also be performed as in Embodiment 1; thus, a repeated description is omitted here.

According to the synthesis scheme (C-2), Ar, $E^1$, and $E^2$ can be different substituents, which is preferable because various compounds can be synthesized. Ar, $E^1$, and $E^2$ can be the same substituents or two of them can be the same substituents.

The triarylamine compound represented by the general formula (G3) in this embodiment is stable toward repetition of an oxidation state and a neutral state, whereby the triarylamine compound can be used for various applications.

As described above, the halogenated diarylamine compound represented by the general formula (G1) can be used as a source material for synthesis of a variety of diarylamine compounds and triarylamine compounds; thus the halogenated diarylamine compound is effective. Further, the diarylamine compound represented by the general formula (G2) which is synthesized using the halogenated diarylamine compound represented by the general formula (G1) can serve as a source material for synthesis of the triarylamine compound represented by the general formula (G3), which is effective. Furthermore, the triarylamine compound represented by the general formula (G3) which is synthesized using one embodiment of the present invention as a starting material can be used for a hole-injection material or a hole-transport material with respect to a light-emitting material, a light-emitting material, or a host material. Note that in the case where the triarylamine represented by the general formula (G3) serves as a light-emitting material, either a material emitting fluorescence or a material emitting phosphorescence can be synthesized.

The structures, methods, and the like described in this embodiment can be combined as appropriate with any of the structures, methods, and the like described in the other embodiments.

Embodiment 3

One embodiment of a light-emitting element using the triarylamine compound described in Embodiment 2 is described below with reference to FIG. 1A.

A substrate 101 is used as a support of a light-emitting element. As the substrate 101, glass, plastic, or the like can be used, for example. Note that materials other than glass or plastic can be used as long as they can function as the support of the light-emitting element.

A first electrode 102 is preferably formed using metal, an alloy, a conductive compound, a mixture thereof, or the like each having a high work function (specifically, greater than or equal to 4.0 eV). Specifically, for example, indium tin oxide (ITO), indium tin oxide containing silicon or silicon oxide, indium zinc oxide (IZO), indium oxide containing tungsten oxide and zinc oxide (IWZO), and the like are given. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like are given.

There is no particular limitation on a stacked structure of an EL layer 103. The EL layer 103 may be formed as appropriate using a layer containing a substance having a high electron-transport property, a layer containing a substance having a high hole-transport property, a layer containing a substance having a high electron-injection property, a layer containing a substance having a high hole-injection property, a layer containing a bipolar substance (a substance having a high electron property and a high hole-transport property), and the like combined with a layer containing the triarylamine compound described in Embodiment 2 according to one embodiment of the present invention. For example, the EL layer 103 can be formed in an appropriate combination of a hole-injection layer, a hole-transport layer, a light-emitting layer, an electron-transport layer, an electron-injection layer, and the like. In this embodiment, the EL layer 103 has a structure in which a hole-injection layer 111, a hole-transport layer 112, a light-emitting layer 113, and an electron-transport layer 114 are sequentially stacked over the first electrode 102.

The hole-injection layer can be using synthesis of the triarylamine compound (general formula (G3)) described in Embodiment 2 which has a preferable hole-injection property and is synthesized using, as a source material, the halogenated diarylamine compound which is one embodiment of the present invention and represented by the general formula (G1). In such a case, as the triarylamine compound represented by the general formula (G3), a compound having a HOMO or LUMO level of 5.0 to 6.0 eV is preferably used. Further, the compound preferably has a hole mobility of greater than or equal to $1 \times 10^{-6}$ cm²/Vs. Specifically, a compound in which at least one of an aryl group Ar, an aryl group $E^1$, and an aryl group $E^2$ in the general formula (G3) corresponds to a substituent of any one of a phenyl group, a naphthalene compound, a fluoranthene compound, a fluorene compound, a phenanthrene compound, a pyrene derivative compound, a triphenylene compound, a chrysene derivative compound, an anthracene compound, a tetracene compound, a carbazole compound, a dibenzofuran compound, and a dibenzothiophene compound can be used.

Alternatively, for the hole-injection layer, the triarylamine compound represented by the general formula (G3) described in Embodiment 2 and a composite material of a substance having a high hole-transport property containing an acceptor substance can be used. Note that, by using the substance having a high hole-transport property containing an acceptor substance, a material for forming an electrode can be selected regardless of its work function. That is, not only a high-work function material, but also a low-work function material can be used for the first electrode 102. As the acceptor substance, 7,7,8,8-tetracyano-2,3,5,6-tetrafluoroquinodimethane (abbreviation: $F_4$-TCNQ), chloranil, and the like are given. Further, transition metal oxide is given. Furthermore, oxide of metal that belongs to Group 4 to Group 8 in the periodic table is given. Specifically, vanadium oxide, niobium oxide, tantalum oxide, chromium oxide, molybdenum oxide, tungsten oxide, manganese oxide, and rhenium oxide are preferable since their electron-accepting property is high. Among these substances, molybdenum oxide is easily treated and preferable since it is stable in the atmosphere and its hygroscopic property is low.

The triarylamine compound represented by the general formula (G3) described in Embodiment 2 can also used for the hole-transport layer. In such a case, as the triarylamine compound represented by the general formula (G3), a substance having a HOMO level of 5.0 to 6.0 eV is preferably used. Further, the band gap (a difference between a HOMO level and a LUMO level) is preferably wide, specifically, it is preferable to use a substance whose band gap is 2.5 eV to 3.5 eV. The substance preferably has a hole mobility of greater than or equal to $1\times10^{-6}$ cm$^2$/Vs. Note that a substance in which the hole-transport property is higher than the electron-transport property is preferably used for the hole-transport layer.

Specifically, a compound in which at least one of an aryl group Ar, an aryl group $E^1$, and an aryl group $E^2$ in the general formula (G3) corresponds to a substituent of any one of a phenyl group, a naphthalene compound, a fluoranthene compound, a fluorene compound, a phenanthrene compound, a pyrene derivative compound, a triphenylene compound, a chrysene derivative compound, an anthracene compound, a tetracene compound, a carbazole compound, a dibenzofuran compound, and a dibenzothiophene compound can be used.

The triarylamine compound represented by the general formula (G3) described in Embodiment 2 can also used for the light-emitting layer. In such a case, as the light-emitting layer, a single layer of the triarylamine compound represented by the general formula (G3) may be formed and used as a light-emitting material. Alternatively, a mixture of the triarylamine compound represented by the general formula (G3) and another organic compound may be formed. When the volume mixing ratio of the triarylamine compound represented by the general formula (G3) to the organic compound is larger, the triarylamine compound serves as a host material, while when the volume mixing ratio of the triarylamine compound to the organic compound is smaller, the triarylamine compound serves as a dopant material.

At this time, the host material preferably has a larger band gap than the dopant material in order to efficiently transfer excitation energy from the host material to the dopant material. In addition, the emission spectrum of the host material preferably overlaps the absorption spectrum of the dopant material in a larger area.

In the case of using the triarylamine compound represented by the general formula (G3) as a blue light-emitting material, the emission wavelength is preferably 420 nm to 500 nm. In the case of using it as a green light-emitting material, the emission wavelength is preferably 500 nm to 600 nm. In the case of using it as a red light-emitting material, the emission wavelength is preferably 600 nm to 750 nm. In order to obtain white light emission, the triarylamine compound preferably has a broad emission wavelength of 420 nm to 750 nm.

In the case of using the triarylamine compound represented by the general formula (G3) for the light-emitting layer, it is preferable to use a stable bipolar material which transports both electrons and holes. Specifically, a compound in which at least one of an aryl group Ar, an aryl group $E^1$, and an aryl group $E^2$ in the general formula (G3) corresponds to a substituent of any one of a phenyl group, a naphthalene compound, a fluoranthene compound, a fluorene compound, a phenanthrene compound, a pyrene derivative compound, a triphenylene compound, a chrysene derivative compound, an anthracene compound, a tetracene compound, a carbazole compound, a dibenzofuran compound, and a dibenzothiophene compound, a pyridine compound, a quinoline compound, an indole compound, an imidazole compound, a purine compound, a pyrimidine compound, a pyrazole compound, an oxazole compound, an oxadiazole compound, a phenanthrene compound, and a thiophene compound. In particular, the anthracene compound and the pyrene compound are preferable because skeletons thereof have a high luminous quantum yield.

In the case of using the triarylamine compound represented by the general formula (G3) as a host material of a phosphorescent material, the T1 level of the triarylamine compound is preferably higher than that of a dopant material of the phosphorescent material in order that T1 energy transfers efficiently. In the case of using the triarylamine compound represented by the general formula (G3) as a dopant of a phosphorescent material, a complex compound formed with a transition metal such as iridium or platinum may be used.

The electron-transport layer contains a substance having a high electron-transport property. For example, the electron-transport layer is a layer including a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances mentioned here are mainly ones that have an electron mobility of greater than or equal to $1\times10^{-6}$ cm$^2$/Vs. Note that a substance other than the above substances may be used for the electron-transport layer as long as it has a higher electron-transport property than a hole-transport property.

Further, the electron-transport layer is not limited to a single layer and may be a stacked layer of two or more layers containing the aforementioned substances.

A layer for controlling transport of electron carriers may be provided between the electron-transport layer and the light-emitting layer. The layer for controlling transport of electron carriers is a layer formed by adding a small amount of substance having a high electron-trapping property to the material having a high electron-transport property as described above and suppresses transfer of electron carriers, so that carrier balance can be adjusted. Such a structure is very effective in suppressing problems (for example, a reduction in the lifetime of the element) which are caused by electrons passing through the light emitting layer.

An electron-injection layer may be provided between the electron-transport layer and the second electrode 104 to be in contact with the second electrode 104. As the electron-injection layer, an alkali metal, an alkaline earth metal, or a compound thereof such as lithium fluoride (LiF), cesium fluoride (CsF), or calcium fluoride (CaF$_2$) may be used. For example, a layer made of a substance having an electron-transport property, in which an alkali metal, an alkaline earth metal, or a compound thereof is contained, specifically a layer of Alq containing magnesium (Mg), and the like can be used. When a layer made of a substance having an electron-transport property, in which an alkali metal or an alkaline earth metal is contained, is used as the electron-injection layer, electrons are efficiently injected from the second electrode, which is preferable.

For the second electrode, metal, an alloy, a conductive compound, or a mixture thereof, or the like, having a low work function (specifically, 3.8 eV or lower) can be used. As specific examples of such a cathode material include an element that belongs to Group 1 or Group 2 in the periodic table, that is, an alkali metal such as lithium (Li) or cesium (Cs); an alkaline-earth metal such as magnesium (Mg), calcium (Ca), or strontium (Sr); an alloy containing the element that belongs to Group 1 or Group 2 (MgAg, AlLi); a rare-earth metal such as europium (Eu) or ytterbium (Yb); an alloy thereof. However, in the case where the electron-injection layer is provided between the second electrode 104 and the electron-transport layer, the second electrode 104 can be formed from any of a variety of conductive materials such as Al, Ag, ITO, or indium tin oxide containing silicon or silicon oxide regardless of its work function. Film formation using such a conductive material can be performed by a sputtering method, an inkjet method, a spin coating method, or the like.

Any of various methods can be employed for forming the EL layer 103 regardless of whether it is a dry method or a wet method. For example, a vacuum evaporation method, an inkjet method, a spin coating method, or the like may be used. A different method may be employed for forming each electrode or each layer. In the case where a film is formed using the triarylamine compound represented by the general formula (G3) by a vacuum evaporation method or in the case where the above triarylamine compound is purified by a sublimation purification method, it is preferable to select a triarylamine compound having a molecular weight of less than or equal to 1000, more preferably less than or equal to 800, in order to avoid influence caused by heating the triarylamine compound. When a wet method is employed, in order to improve solubility in a solvent, it is preferable to use the triarylamine compound described in Embodiment 2, in which an alkyl group is introduced as a substituent. Further, in order to prevent crystallization after the film formation, it is preferable to use a molecule that has a high level of amorphousness, specifically, a molecule having a molecular weight of greater than or equal to 500, more preferably greater than or equal to 600.

Similarly, the electrode may be formed by a wet method such as a sol-gel method or by a wet method using a paste of a metal material. Alternatively, a dry method such as a sputtering method or a vacuum evaporation method may be used.

In the light-emitting element of one embodiment of the present invention having the structure as described above, the potential difference generated between the first electrode 102 and the second electrode 104 makes a current flow, whereby holes and electrons are recombined in the light-emitting layer 113 that contains a substance having a high light-emitting property and thus light is emitted. That is, a light-emitting region is formed in the light-emitting layer 113.

Light emission is extracted out through one or both of the first electrode 102 and the second electrode 104. Therefore, one or both of the first electrode 102 and the second electrode 104 is/are light-transmissive electrodes. In the case where only the first electrode 102 is a light-transmissive electrode, light emission is extracted from a substrate side through the first electrode 102. On the other hand, in the case where only the second electrode 104 is a light-transmissive electrode, light emission is extracted from the side opposite to the substrate side through the second electrode 104. In the case where both the first electrode 102 and the second electrode 104 are light-transmissive electrodes, light emission is extracted from both the substrate side and the side opposite to the substrate side through the first electrode 102 and the second electrode 104.

The structure of the layers provided between the first electrode 102 and the second electrode 104 is not limited to the above structures. However, it is preferable to use a structure in which a light-emitting region where holes and electrons are recombined is provided away from the first electrode 102 and the second electrode 104 so as to prevent quenching due to the proximity of the light-emitting region and metal used for the electrode or a carrier (electron or hole) injection layer. The order of stacking the layers is not limited to the above, and the following order, which is opposite to that in FIG. 1A, may be employed: the second electrode, the electron-injection layer, the electron-transport layer, the light-emitting layer, the hole-transport layer, the hole-injection layer, and the first electrode from the substrate side.

In addition, as for the hole-transport layer or the electron-transport layer in direct contact with the light-emitting layer, particularly a carrier (electron or hole) transport layer in contact with a side closer to a light-emitting region in the light-emitting layer 113, in order to suppress energy transfer from an exciton which is generated in the light-emitting layer, it is preferable that an energy gap thereof be larger than an energy gap of a light-emitting substance which forms the light-emitting layer or an energy gap of an emission center substance included in the light-emitting layer.

The structures, methods, and the like described in this embodiment can be combined as appropriate with any of the structures, methods, and the like described in the other embodiments.

Embodiment 4

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element has a plurality of light-emitting units between a first electrode and a second electrode. The light-emitting unit may have a structure similar to that of the EL layer 103 described in Embodiment 3. That is, the light-emitting element having a single light-emitting unit is described in Embodiment 3, and a light-emitting element having a plurality of light-emitting units is described in this embodiment.

Figure 1B:
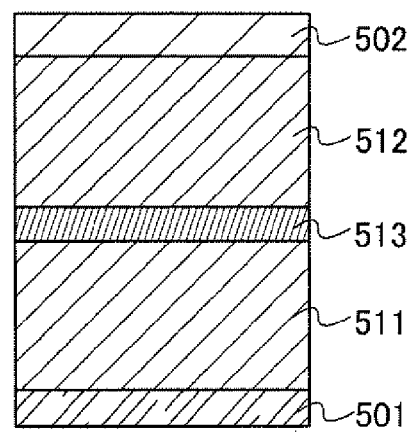

In FIG. 1B, a first light-emitting unit 511 and a second light-emitting unit 512 are stacked between a first electrode 501 and a second electrode 502. Electrodes similar to those described in Embodiment 3 can be used as the first electrode 501 and the second electrode 502. Further, the first light-emitting unit 511 and the second light-emitting unit 512 may have the same or different structures. The structure similar to that in Embodiment 3 can be applied to the structures of the first and second light-emitting units 511 and 512.

A charge generation layer 513 includes a composite material of an organic compound and a metal oxide. This composite material of an organic compound and a metal oxide is the composite material described in Embodiment 3 and includes an organic compound and a metal oxide such as $V_2O_5$, $MoO_3$, or $WO_3$. As the organic compound, a variety of compounds such as an aromatic amine compound, a carbazole compound, aromatic hydrocarbon, and a high molecular compound (an oligomer, a dendrimer, a polymer, or the like) can be used. Note that as the organic compound, it is preferable to use an organic compound having a hole mobility of greater than or equal to $1\times10^{-6}$ cm$^2$/Vs, which serves as a hole-transport organic compound. The composite material of an organic compound and a metal oxide is superior in a carrier-injection property and a carrier-transport property, so that it can achieve low-voltage driving and low-current driving.

Note that the charge generation layer 513 may be formed by combination of the composite material of an organic compound and a metal oxide with another material. For example, a layer including the composite material of an organic compound and a metal oxide may be used in combination with a layer including a compound selected from electron-donating substances and a compound with a high electron-transport property. Further, a layer including the composite material of an organic compound and a metal oxide may be used in combination with a transparent conductive film.

In any case, any layer can be employed as the charge generation layer 513 sandwiched between the first light-emitting unit 511 and the second light-emitting unit 512 as long as the layer injects electrons into one of these light-emitting units and holes into the other when voltage is applied to the first electrode 501 and the second electrode 502.

Although the light-emitting element having two light-emitting units is described in this embodiment, a light-emitting element in which three or more light-emitting units are stacked can be employed in a similar way. When the charge generation layer is provided between the pair of electrodes so as to partition the plural light-emitting units like in the light-emitting element of this embodiment, the element can have a long lifetime in a high luminance region while the current density is kept low.

A blue light-emitting element, a green light-emitting element, and a red light-emitting element according to Embodiments 3 and 4 are combined, so that a full-color display can be manufactured. Further, white lighting can be obtained with the use of a material that emits white light. When a white light-emitting element is used as a back light and combined with a color filter of blue, green, and red, a full-color display also can be manufactured. An intermediate color light-emitting element such as blue-green light-emitting element and a primary color light-emitting element such as red light-emitting element are used to make white light, which can be used as a back light of a display or lighting.

The light-emitting elements according to Embodiments 3 and 4 can be used as light-emitting components of a variety of light-emitting devices. Further, the light-emitting device can be applied to a variety of electronic appliances. Specifically, the light-emitting device can be applied to applications to displays such as TVs, cellular phones, and the like; applications to lighting of streetlights; traffic lights; lighting of refrigerators; lighting for breeding that can be used in a vinyl house; or the like are given.

In Embodiments 3 and 4, the light-emitting element is manufactured over a substrate formed using glass, plastic, or the like. A plurality of such light emitting elements is formed over one substrate, whereby a passive matrix light-emitting device can be manufactured. Further, for example, a thin film transistor (TFT) may be formed over the substrate formed using glass, plastic, or the like, and a light-emitting element may be manufactured over an electrode electrically connected to the TFT. In this manner, an active matrix light-emitting device in which the TFT controls the drive of the light-emitting element can be manufactured. Note that there is no particular limitation on the structure of the TFT. Either a staggered TFT or an inverted staggered TFT may be employed. There is no particular limitation on the crystallinity of a semiconductor used for the TFT, and an amorphous semiconductor or a crystalline semiconductor may be used. Furthermore, a driver circuit formed over a TFT substrate may be formed using both n-channel and p-channel TFTs or may be formed using n-channel TFTs or p-channel TFTs.

Note that this embodiment can be combined with any of the other embodiments as appropriate.

Embodiment 5

In this embodiment, an example in which the triarylamine compound described in Embodiment 2 is used for an active layer of a vertical transistor (SIT), which is a kind of an organic semiconductor element, is described.

The triarylamine compound described in Embodiment 2 has an excellent stability with respect to holes, and can be used for transporting carriers.

Figure 2:
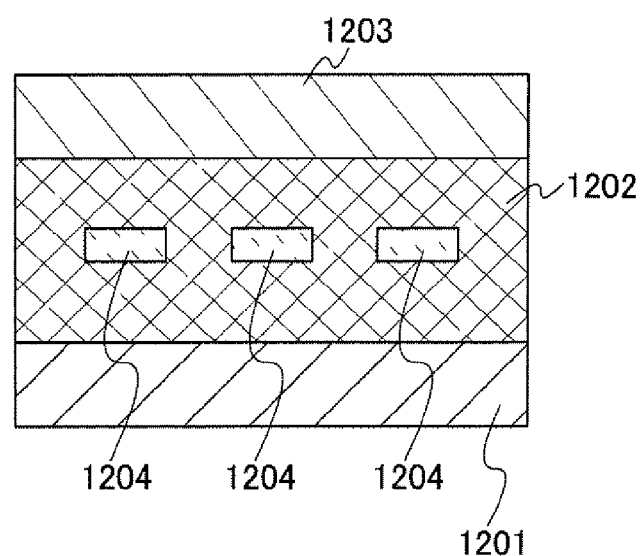
FIG. 2 is a conceptual diagram of an organic semiconductor element according to one embodiment of the present invention.

The element structure is as follows: a thin active layer 1202 including the triarylamine compound described in Embodiment 2 is sandwiched between a source electrode 1201 and a drain electrode 1203, and a gate electrode 1204 is embedded in the active layer 1202, as illustrated in FIG. 2. The gate electrode 1204 is electrically connected to a unit to apply a gate voltage, and the source electrode 1201 and the drain electrode 1203 are electrically connected to a unit to control the voltage between the source and the drain.

Embodiment 6

In this embodiment, as examples of a light-emitting device which is manufactured with the use of the light-emitting element described in the above embodiments, a passive matrix light-emitting device and an active matrix light-emitting device are described.

FIGS. 24A to 24D and FIG. 25 illustrate an example of a passive matrix light-emitting device.

In a passive-matrix (also referred to as "simple-matrix") light-emitting device, a plurality of anodes arranged in stripes (in stripe form) are provided to be orthogonal to a plurality of cathodes arranged in stripes, and a light-emitting layer is interposed at each intersection. Therefore, a pixel at an intersection of an anode selected (to which voltage is applied) and a cathode selected emits light.

Figure 24A:
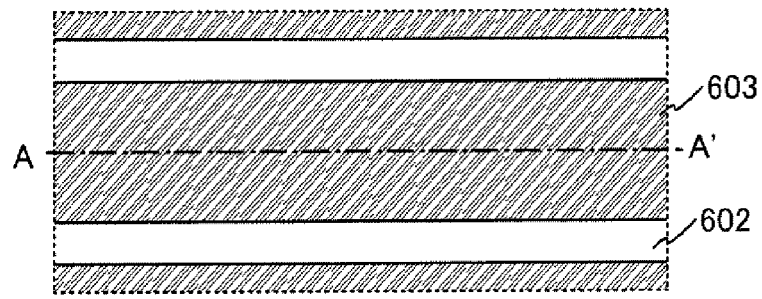
FIGS. 24A to 24D are diagrams illustrating an example of a light-emitting device according to one embodiment of the present invention.
Figure 24B:
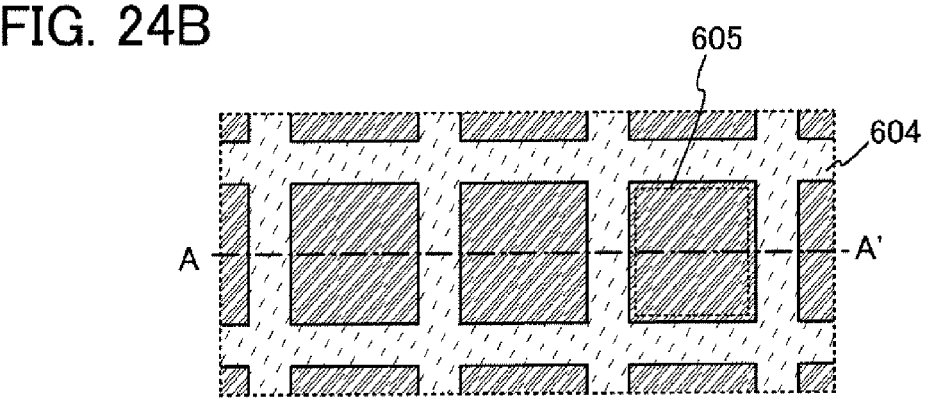
Figure 24C:
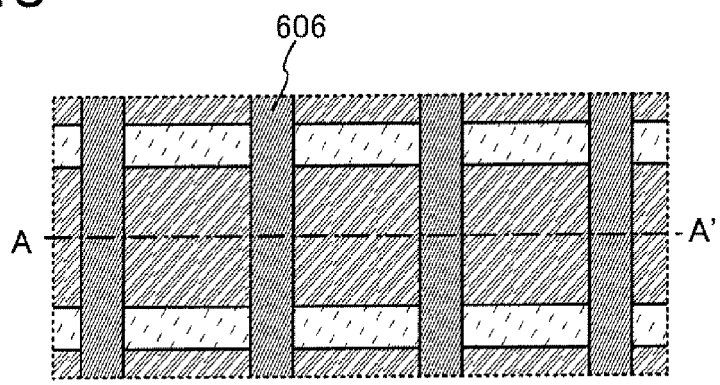
Figure 24D:
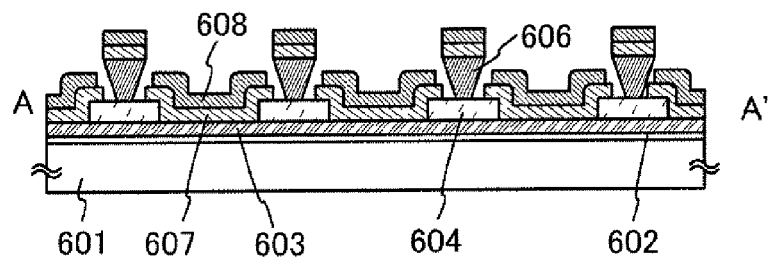

FIGS. 24A to 24C are top views of a pixel portion before sealing, and FIG. 24D is a cross-sectional view taken along chain line A-A' in FIGS. 24A to 24C.

Over a substrate 601, an insulating layer 602 is formed as a base insulating layer. Note that the insulating layer 602 is not necessarily formed if the base insulating layer is not needed. Over the insulating layer 602, a plurality of first electrodes 603 are arranged in stripes with equal spacing therebetween (FIG. 24A). Note that the first electrode 603 corresponds to the first electrode 102 in Embodiment 3.

A partition wall 604 having openings each corresponding to a pixel is provided over the first electrodes 603. The partition wall 604 having openings is formed using an insulating material (a photosensitive or nonphotosensitive organic material (polyimide, acrylic, polyamide, polyimide amide, resist, or benzocyclobutene) or an SOG film (such as a silicon oxide film containing an alkyl group)). Note that an opening 605 corresponding to each pixel acts as a light-emitting region (FIG. 24B).

Over the partition wall 604 having openings, a plurality of mutually parallel inversely tapered partition walls 606 are provided to intersect with the first electrodes 603 (FIG. 24C). The inversely tapered partition walls 606 are formed by a photolithography method using a positive-type photosensitive resin by which a portion unexposed to light remains as a pattern, and the amount of light exposure or the length of development time is adjusted so that a lower portion of the pattern is etched more.

After the inversely tapered partition walls 606 are formed as illustrated in FIG. 24C, EL layers 607 and second electrodes 608 are sequentially formed as illustrated in FIG. 24D. The EL layer 607 in this embodiment corresponds to the EL layer 103 in Embodiment 3 and includes at least a hole-transport layer and a layer containing a light-emitting substance adjoining the hole-transport layer. In addition, the second electrode 608 corresponds to the second electrode 104 in Embodiment 3. The height obtained by adding the height of the partition wall 604 having openings and the height of the inversely tapered partition wall 606 is larger than the sum of the thicknesses of the EL layer 607 and the second electrode 608. Therefore, as illustrated in FIG. 24D, the EL layers 607 and the second electrodes 608 which are separated into a plurality of regions are formed. Note that the plurality of separated regions is electrically isolated from one another.

The second electrodes 608 are electrodes in stripes which are parallel to each other and extend in a direction intersecting with the first electrodes 603. Note that a part of the EL layers 607 and a part of conductive layers forming the second electrodes 608 are formed over the inversely tapered partition walls 606; however, they are separated from the EL layers 607 and the second electrodes 608.

In addition, a sealing member such as a sealing can or a glass substrate may be attached to the substrate 601 with adhesive such as a sealant so that the light-emitting element can be placed in a sealed space, if necessary. In this manner, the light-emitting element can be prevented from deteriorating. The sealed space may be filled with filler or a dry inert gas. In addition, a desiccant or the like may be put between the substrate and the sealing member so that deterioration of the light-emitting element due to moisture or the like can be prevented. The desiccant removes a minute amount of moisture, thereby achieving sufficient desiccation. The desiccant can be a substance which absorbs moisture by chemical adsorption such as an oxide of an alkaline earth metal typified by calcium oxide or barium oxide. Note that a substance which adsorbs moisture by physical adsorption such as zeolite or silica gel may be used as well.

Figure 25:
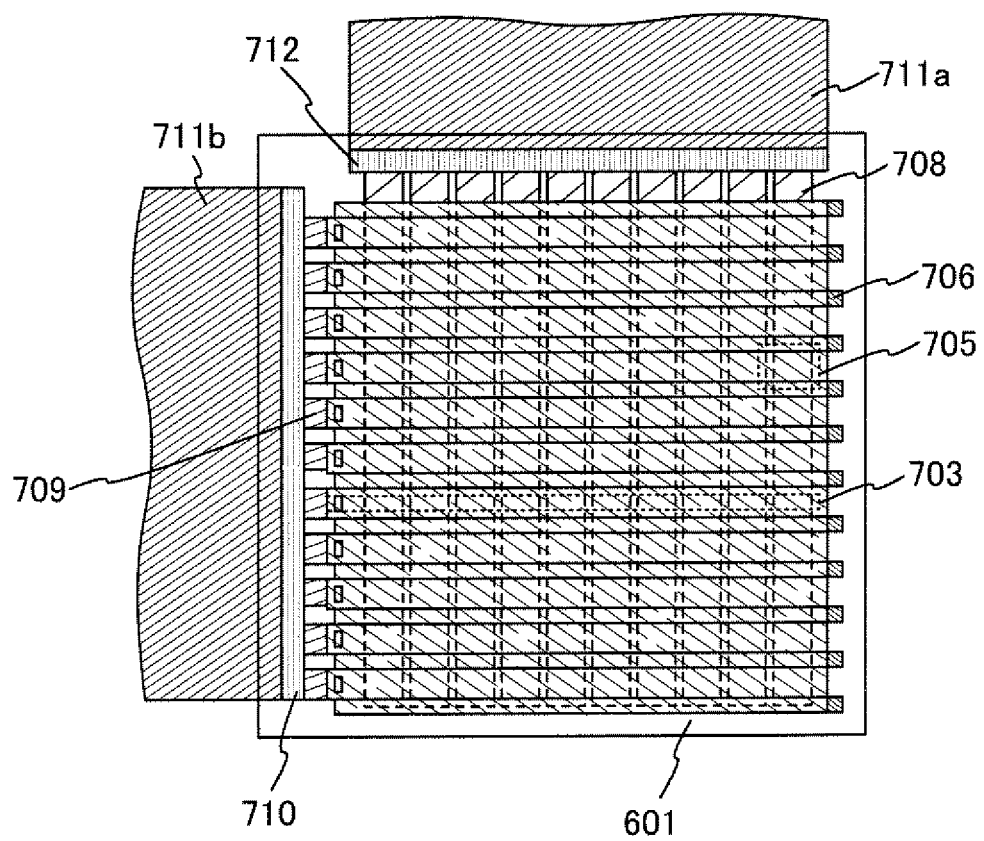
FIG. 25 is a diagram illustrating an example a light-emitting device according to one embodiment of the present invention.

FIG. 25 is a top view in the case where the passive-matrix light-emitting device illustrated in FIGS. 24A to 24D is provided with a flexible printed circuit (FPC) or the like.

As illustrated in FIG. 25, in a pixel portion forming an image display, scanning lines and data lines intersect with each other so that they are orthogonal to each other.

The first electrodes 603 in FIGS. 24A to 24D correspond to scanning lines 703 in FIG. 25; the second electrodes 608 in FIGS. 24A to 24D correspond to data lines 708 in FIG. 25; and the inversely tapered partition walls 606 correspond to partition walls 706. The EL layers 607 illustrated in FIG. 24D are interposed between the data lines 708 and the scanning lines 703, and an intersection indicated by a region 705 corresponds to one pixel.

Note that the scanning lines 703 are electrically connected at their ends to connection wirings 709, and the connection wirings 709 are connected to an FPC 711b via an input terminal 710. The data lines 708 are connected to an FPC 711a via an input terminal 712.

If necessary, a polarizing plate, a circularly polarizing plate (including an elliptically polarizing plate), a retardation plate (a quarter-wave plate or a half-wave plate), or an optical film such as a color filter may be appropriately provided over a light-emitting surface. Further, the polarizing plate or the circularly polarizing plate may be provided with an anti-reflection film. For example, anti-glare treatment may be carried out by which reflected light can be diffused by projections and depressions on the surface so as to reduce the reflection.

Although FIG. 25 illustrates the example in which a driver circuit is not provided over the substrate, an IC chip including a driver circuit may be mounted on the substrate.

When the IC chip is mounted, a data line side IC and a scanning line side IC, in each of which the driver circuit for transmitting a signal to a pixel portion is formed, are mounted on the periphery of (outside) the pixel portion by a COG method. The mounting may be performed using TCP or a wire bonding method other than the COG method. TCP is TAB tape mounted with an IC, and the TAB tape is connected to a wiring over an element formation substrate and the IC is mounted. Each of the data line side IC and the scanning line side IC may be formed using a silicon substrate or may be formed by formation of a driver circuit using a TFT over a glass substrate, a quartz substrate, or a plastic substrate.

Figure 26A:
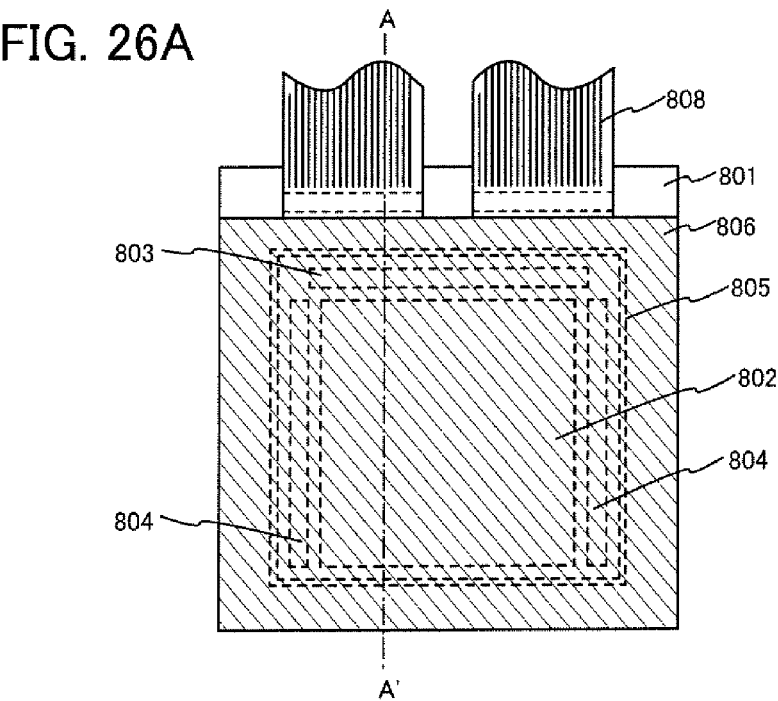
FIGS. 26A and 26B are diagrams illustrating an example of a light-emitting device according to one embodiment of the present invention.
Figure 26B:
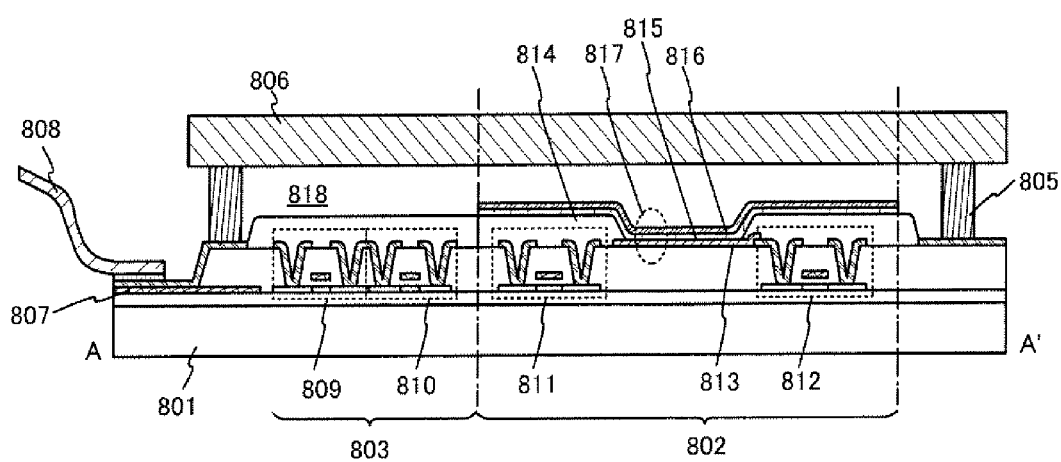

Next, an example of an active-matrix light-emitting device is described with reference to FIGS. 26A and 26B. Note that FIG. 26A is a top view illustrating a light-emitting device and FIG. 26B is a cross-sectional view taken along chain line A-A' in FIG. 26A. The active-matrix light-emitting device of this embodiment includes, over an element substrate 801, a pixel portion 802, a driver circuit portion (a source side driver circuit) 803, and a driver circuit portion (a gate side driver circuit) 804. The pixel portion 802, the driver circuit portion 803, and the driver circuit portion 804 are sealed with a sealant 805 between the element substrate 801 and a sealing substrate 806.

In addition, over the element substrate 801, a lead wiring 807 for connecting an external input terminal, through which a signal (e.g., a video signal, a clock signal, a start signal, a reset signal, or the like) or electric potential from the outside is transmitted to the driver circuit portion 803 and the driver circuit portion 804, is provided. Here, an example is described in which a FPC 808 is provided as the external input terminal. Although only the FPC is illustrated here, this FPC may have a printed wiring board (PWB) attached. The light-emitting device in this specification includes not only a light-emitting device itself but also a state in which an FPC or a PWB is attached thereto.

Next, a cross-sectional structure is described with reference to FIG. 26B. Although the driver circuit portions and the pixel portion are formed over the element substrate 801. The pixel portion 802 and the driver circuit portion 803 which is the source side driver circuit are illustrated.

An example is illustrated in which a CMOS circuit which is a combination of an n-channel TFT 809 and a p-channel TFT 810 is formed as the driver circuit portion 803. Note that a circuit included in the driver circuit portion may be formed using various CMOS circuits, PMOS circuits, or NMOS circuits. Although a driver integrated type in which the driver circuit is formed over the substrate is described in this embodiment, the driver circuit is not necessarily formed over the substrate, and the driver circuit can be formed outside, not over the substrate.

Further, the pixel portion 802 has a plurality of pixels, each including a switching TFT 811, a current control TFT 812, and an anode 813 electrically connected to a wiring (a source electrode or a drain electrode) of the current control TFT 812. An insulator 814 is formed so as to cover an edge portion of the anode 813. In this embodiment, the insulator 814 is formed using a positive photosensitive acrylic resin.

In addition, in order to obtain favorable coverage by a film which is to be stacked over the insulator 814, the insulator 814 is preferably formed so as to have a curved surface with curvature at an upper edge portion or a lower edge portion. For example, in the case of using a positive photosensitive acrylic resin as a material for the insulator 814, the insulator 814 is preferably formed so as to have a curved surface with a curvature radius (0.2 µm to 3 µm) at the upper edge portion. Either a negative photosensitive material which becomes insoluble in an etchant by light or a positive photosensitive material which becomes soluble in an etchant by light can be used for the insulator 814. As the insulator 814, without limitation to an organic compound, an inorganic compound such as silicon oxide or silicon oxynitride can be used.

An EL layer 815 and a cathode 816 are stacked over the anode 813. Note that when an ITO film is used as the anode 813, and a stacked film of a titanium nitride film and a film containing aluminum as its main component or a stacked film of a titanium nitride film, a film containing aluminum as its main component, and a titanium nitride film is used as a wiring of the current control TFT 812 which is connected to the anode 813, resistance of the wiring can be low and favorable ohmic contact with the ITO film can be obtained. Note that, although not illustrated, the cathode 816 is electrically connected to the FPC 808 which is an external input terminal.

The light-emitting element includes the anode 813, the EL layer 815, and the cathode 816 as described above. The specific structures and materials of the light-emitting element have been described in Embodiments 1 to 3, so that the repeated description is omitted. Note that the anode 813, the EL layer 815, and the cathode 816 in FIGS. 26A and 26B correspond to the first electrode 102, the EL layer 103, and the second electrode 104 in Embodiment 3, respectively.

In addition, although the cross-sectional view of FIG. 26B illustrates only one light-emitting element 817, a plurality of light-emitting elements are arranged in matrix in the pixel portion 802. Light-emitting elements that emit light of three kinds of colors (R, G, and B) are formed in the pixel portion 802, whereby a light-emitting device capable of full color display can be obtained. Alternatively, a light-emitting device which is capable of full color display may be manufactured by a combination with color filters.

By attachment of the sealing substrate 806 to the element substrate 801 with the sealant 805, a structure in which the light-emitting element 817 is provided in a space 818 surrounded by the element substrate 801, the sealing substrate 806, and the sealant 805 is obtained. Note that the space 818 may be filled with an inert gas (such as nitrogen and argon) or the sealant 805.

It is preferable to use an epoxy-based resin for the sealant 805. In addition, preferably, the material does not transmit moisture or oxygen as much as possible. As the sealing substrate 806, a plastic substrate formed of FRP (fiberglass-reinforced plastics), PVF (polyvinyl fluoride), polyester, acrylic, or the like can be used besides a glass substrate or a quartz substrate.

As described above, an active-matrix light-emitting device can be obtained.

Note that the structure described in this embodiment can be combined with any of the structures described in other embodiments as appropriate.

Embodiment 7

In this embodiment, various electronic appliances and lighting devices, each of which is completed using the light-emitting device described in the above embodiment, are described with reference to FIGS. 27A to 27E.

As the electronic appliances described in this embodiment, for example, there are a television set (also called TV or a television receiver), a monitor for a computer or the like, a digital camera, a digital video camera, a digital photo frame, a mobile phone set (also called a mobile phone or a portable telephone device), a portable game machine, a portable information terminal, an audio playback device, a large game machine such as a pachinko machine, and the like. Specific examples of these electronic appliances and lighting devices are illustrated in FIGS. 9A to 9E.

Figure 27A:
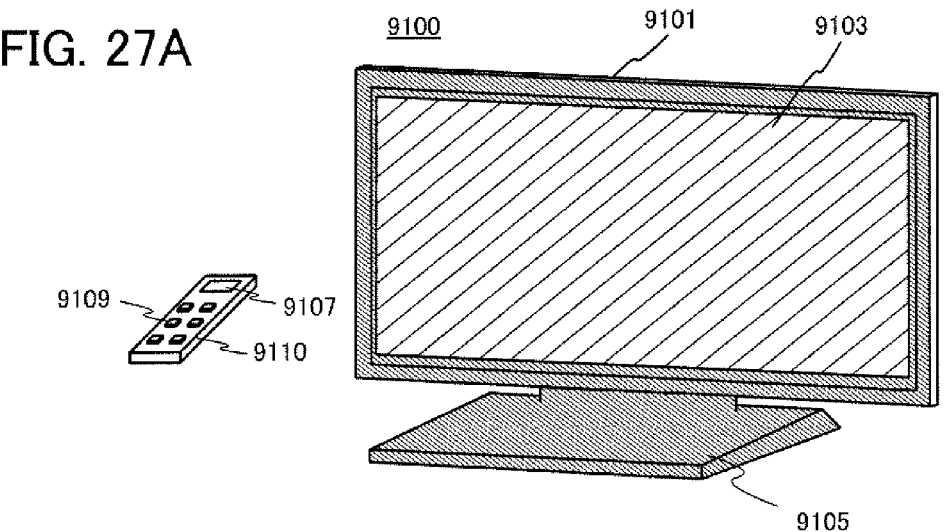
FIGS. 27A to 27E are each a diagram illustrating an example of an electronic appliance according to one embodiment of the present invention.

FIG. 27A illustrates an example of a television set. A display portion 9103 is incorporated in a housing 9101 of the television set 9100. Images can be displayed in the display portion 9103, for which the light-emitting device described in the above embodiment can be used. Further, the housing 9101 is supported by a stand 9105 here.

The television set 9100 can be operated by an operation switch provided on the housing 9101 or a separate remote controller 9110. The channel and volume can be controlled with operation keys 9109 provided on the remote controller 9110 and the images displayed in the display portion 9103 can be controlled. Furthermore, the remote controller 9110 may be provided with a display portion 9107 for displaying data output from the remote controller 9110.

Note that the television set 9100 is provided with a receiver, a modem, and the like. With the receiver, a general television broadcast can be received. Furthermore, when the television set 9100 is connected to a communication network by wired or wireless connection via the modem, one-way (from a transmitter to a receiver) or two-way (between a transmitter and a receiver, between receivers, or the like) data communication can be performed.

Since the light-emitting device formed in accordance with the above embodiments has long lifetime, a television set with long lifetime can be provided by using the light-emitting device for the display portion 9103. Further, since the light-emitting device exhibits high chromaticity, by using the light-emitting device for the display portion 9103 of the television set, an image with improved quality can be displayed.

Figure 27B:
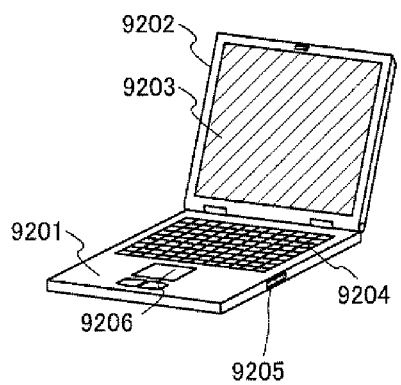

FIG. 27B is a computer including a main body 9201, a housing 9202, a display portion 9203, a keyboard 9204, an external connection port 9205, a pointing device 9206, and the like. Note that the computer is manufactured using the light-emitting device which is formed in accordance with the above embodiments for the display portion 9203.

Since the light-emitting device formed in accordance with the above embodiments has long lifetime, a computer with long lifetime can be provided by using the light-emitting device for the display portion 9203 of the computer. Further, since the light-emitting device exhibits high chromaticity, by using the light-emitting device for the display portion 9203 of the computer, an image with improved quality can be displayed.

Figure 27C:
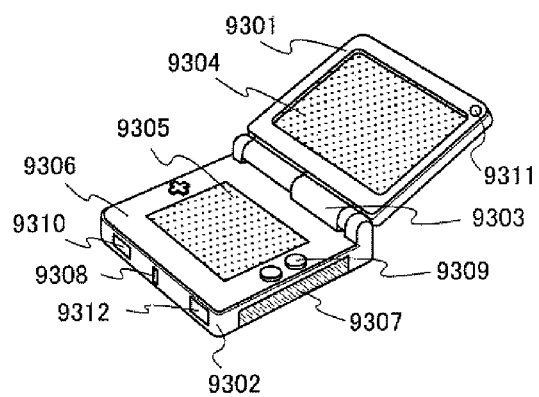

FIG. 27C illustrates a portable amusement machine including two housings: a housing 9301 and a housing 9302. The housing 9301 and 9302 are connected with a connection portion 9303 so as to be opened and closed. A display portion 9304 is incorporated in the housing 9301 and a display portion 9305 is incorporated in the housing 9302. In addition, the portable amusement machine illustrated in FIG. 27C includes an input means such as an operation key 9309, a connection terminal 9310, a sensor 9311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 9312. The portable amusement machine may also be provided with a speaker portion 9306, a recording medium insertion portion 9307, an LED lamp 9308, and the like. The structure of the portable amusement machine is not limited to the above and it is acceptable as long as the light-emitting device formed in according with the above embodiments is used at least for one or both of the display portion 9304 and the display portion 9305. The portable amusement machine may also include other accessories as appropriate.

The portable amusement machine illustrated in FIG. 27C has a function of reading a program or data stored in a recording medium to display it in the display portion, and a function of sharing information with another portable amusement machine by wireless communication. Note that the functions of the portable amusement machine illustrated in FIG. 27C are not limited to these functions, and the portable amusement machine can have various functions.

Since the light-emitting device formed in accordance with the above embodiments has long lifetime, a portable amusement machine with long lifetime can be provided by using the light-emitting device for the display portions 9304 and 9305 of the portable amusement machine. Further, since the light-emitting device exhibits high chromaticity, by using the light-emitting device for the display portions 9304 and 9305 of the portable amusement machine, an image with improved quality can be displayed.

Figure 27D:
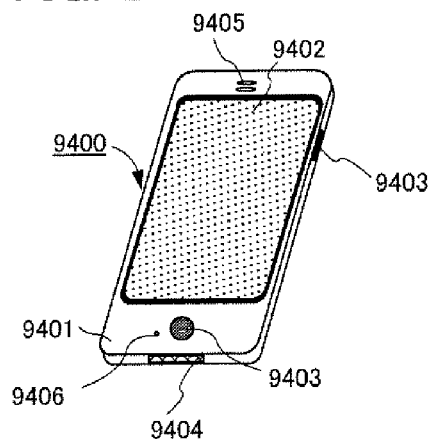

FIG. 27D illustrates an example of a mobile phone set. A mobile phone set 9400 is provided with a display portion 9402 incorporated in a housing 9401, an operation button 9403, an external connection port 9404, a speaker 9405, a microphone 9406, and the like. The mobile phone set 9400 is manufactured using the light-emitting device which is formed in accordance with the above embodiments for the display portion 9402.

When the display portion 9402 of the mobile phone set 9400 illustrated in FIG. 27D is touched with a finger or the like, data can be input to the mobile phone set 9400. In addition, operations such as phone call or composing of a mail can be conducted by touching the display portion 9402 with a finger or the like.

There are mainly three screen modes for the display portion 9402. The first mode is a display mode mainly for displaying an image. The second mode is an input mode mainly for inputting information such as text. The third mode is a display-and-input mode in which two modes of the display mode and the input mode are combined.

For example, in the case of making a phone call or composing a mail, a text input mode mainly for inputting text is selected for the display portion 9402 so that characters displayed on a screen can be input. In this case, it is preferable to display a keyboard or number buttons on almost the entire screen of the display portion 9402.

When a detection device including a sensor for detecting inclination, such as a gyroscope or an acceleration sensor, is provided inside the mobile phone set 9400, display on the screen of the display portion 9402 can be automatically switched by determining the orientation of the mobile phone set 9400 (whether the mobile phone set 9400 is placed horizontally or vertically for a landscape mode or a portrait mode).

Further, the screen modes are switched by touching the display portion 9402 or operating the operation button 9403 provided on the housing 9401. Alternatively, the screen modes can be switched depending on kinds of images displayed in the display portion 9402. For example, when a signal for an image displayed in the display portion is data of moving images, the screen mode is switched to the display mode. When the signal is text data, the screen mode is switched to the input mode.

Moreover, in the input mode, when input by touching the display portion 9402 is not performed within a specified period of time while a signal detected by an optical sensor in the display portion 9402 is detected, the screen mode may be controlled so as to be switched from the input mode to the display mode.

The display portion 9402 may also function as an image sensor. For example, an image of a palm print, a fingerprint, or the like is taken by touching the display portion 9402 with a palm or a finger, whereby personal authentication can be performed. Furthermore, by providing a backlight or a sensing light source emitting near-infrared light for the display portion, an image of a finger vein, a palm vein, or the like can also be taken.

Since the light-emitting device formed in accordance with the above embodiments has long lifetime, a mobile phone set with long lifetime can be provided by using the light-emitting device for the display portion 9402 of the mobile phone set. Further, since the light-emitting device exhibits high chromaticity, by using the light-emitting device for the display portion 9402 of the mobile phone set, an image with improved quality can be displayed.

Figure 27E:
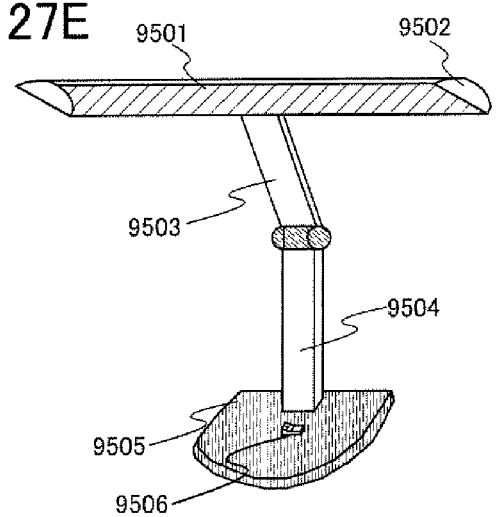

FIG. 27E illustrates a desk lamp including a lighting portion 9501, a shade 9502, an adjustable arm 9503, a support 9504, a base 9505, and a power switch 9506. The desk lamp is manufactured using the light-emitting device which is formed in accordance with the above embodiments for the lighting portion 9501. Note that the lighting device includes a ceiling light, a wall light, and the like.

Since the light-emitting device formed in accordance with the above embodiments has long lifetime, a desk lamp with long lifetime can be provided by using the light-emitting device for the lighting portion 9501 of the desk lamp.

Figure 28:
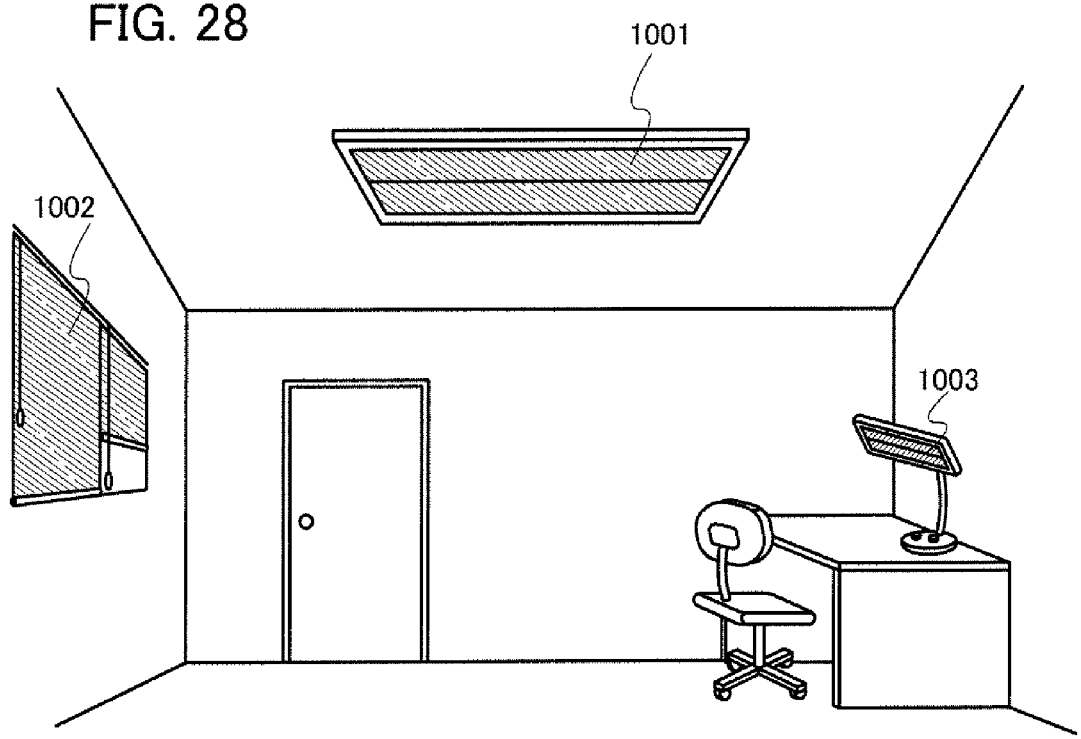
FIG. 28 is a diagram illustrating an example of a lighting device according to one embodiment of the present invention.

FIG. 28 is an example in which the light-emitting device formed in accordance with the above embodiments is used as an indoor lighting device 1001. Since the light-emitting device described in the above embodiments can be increased in area, the light-emitting device can be used as a lighting device having a large area. In addition, the light-emitting device described in the above embodiments can be thinned and thus can be used as a roll-up type lighting device 1002. Since the light-emitting device formed in accordance with the above embodiments has a long-lifetime light-emitting element, the light-emitting device can be used as a long-lifetime lighting device. As illustrated in FIG. 28, a desk lamp 1003 as illustrated in FIG. 27E may be used in a room provided with the indoor lighting device 1001.

As described above, an electronic appliance or a lighting device can be obtained by using the light-emitting device described in the above embodiments. The light-emitting device has a remarkably wide application range, and can be applied to electronic appliances in various fields.

Note that the structure described in this embodiment can be combined with any of the structures described in other embodiments as appropriate.

Example 1

Synthesis Example 1

In this example, a synthesis method of 4-bromo-4'-(1-naphthyl)diphenylamine (abbreviation: BrNBA), which is represented by the following structural formula (100) is described.

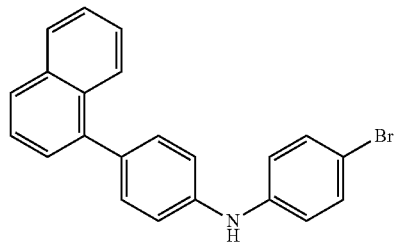

(100)

Step 1: Synthesis of 1-(4-bromophenyl)-naphthalene

In a 500-mL three-neck flask, 46 g (160 mmol) of 4-bromoiodobenzene, 24 g (140 mmol) of 1-naphthaleneboronic acid, 45 mg (0.2 mmol) of palladium(II) acetate, and 60 mg (0.2 mmol) of tris(o-tolyl)phosphine were put, and 100 mL of toluene, 20 mL of ethanol, and 11 mL of a potassium carbonate solution (2 mol/L) were added thereto. This mixture was degassed while being stirred under reduced pressure. After that, the mixture was stirred under a nitrogen atmosphere at 90° C. for 4 hours to be reacted.

After the reaction, 500 mL of toluene was added to the reaction mixture solution, and the resulting suspension was filtrated through Florisil (Catalog No. 540-00135, produced by Wako Pure Chemical Industries, Ltd.) and Celite (Catalog No. 531-16855, produced by Wako Pure Chemical Industries, Ltd.). The obtained filtrate was washed with water, and magnesium sulfate was added thereto to adsorb moisture. This suspension was filtrated through Florisil and Celite to obtain a filtrate. The obtained filtrate was concentrated and purified by silica gel column chromatography (developing solvent: hexane). The obtained fraction was concentrated to obtain 25 g of a colorless transparent liquid which was a desired substance in a yield of 62%. A reaction of the above synthesis method is shown in the following scheme (F-1).

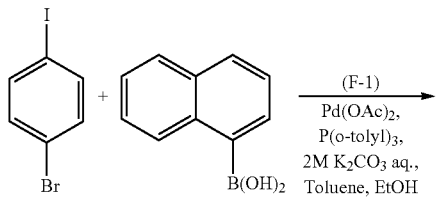

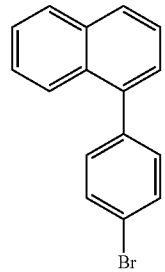

An Rf value of the desired substance by a silica gel thin layer chromatography (TLC) (developing solvent: hexane) was 0.38 and that of 4-bromoiodobenzene was 0.57.

Step 2: Synthesis of 4-(1-naphthyl)diphenylamine

In a 100-mL three-neck flask, 2.8 g (10 mmol) of 1-(4-bromophenyl)-naphthalene, 0.9 g (10 mmol) of aniline, 1.0 g (10 mmol) of sodium tert-butoxide, and 20 mg (0.04 mmol) of bis(dibenzylideneacetone)palladium(0) were put, and the atmosphere of the flask was substituted by nitrogen. Then, 20 mL of toluene was added to this mixture. This mixture was degassed while being stirred under reduced pressure. After that, 0.1 mL (0.06 mmol) of tri(tert-butyl)phosphine (a 10 wt % hexane solution) was added thereto. This mixture was stirred under a nitrogen atmosphere at 110° C. for 4 hours to be reacted.

After the reaction, 150 mL of toluene was added to this reaction mixture solution, and this suspension was filtrated through Florisil and Celite. The obtained filtrate was concentrated and purified by silica gel column chromatography (developing solvent is toluene:hexane=1:4). The obtained fraction was concentrated, and hexane was added thereto. The mixture was irradiated with ultrasonic wave and then recrystallized, so that 2.2 g of a white powder which was a desired substance was obtained in a yield of 75%. A reaction of the above synthesis method is shown in the following scheme (F-2).

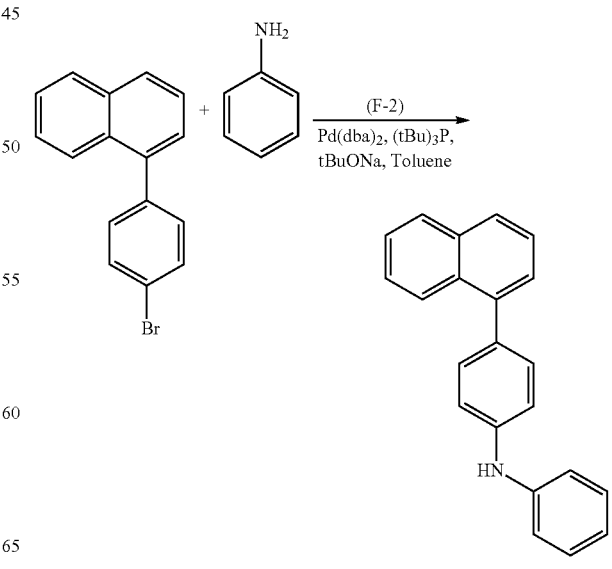

An Rf value of the desired substance by a silica gel thin layer chromatography (TLC) (developing solvent is ethyl acetate:hexane=1:10) was 0.13, and that of 1-(4-bromophenyl)-naphthalene was 0.53.

Step 3: Synthesis of 4-bromo-4'-(1-naphthyl)diphenylamine (Abbreviation: BrNBA)

After 590 mg (2.0 mmol) of 4-(1-naphthyl)diphenylamine was dissolved in 20 mL of ethyl acetate in a 50 mL conical flask, 360 mg (2.0 mmol) of N-bromo succinimide (abbreviation: NBS) was added to this solution. Then, this mixture was stirred at room temperature for 70 hours. After completion of the reaction, this mixture solution was washed with water, and magnesium sulfate was added thereto to adsorb moisture. This suspension was filtrated, and the obtained filtrate was concentrated and dried to obtain 720 mg of a white powder which was a desired substance in a yield of 96%. A reaction of the above synthesis method is shown in the following scheme (F-3).

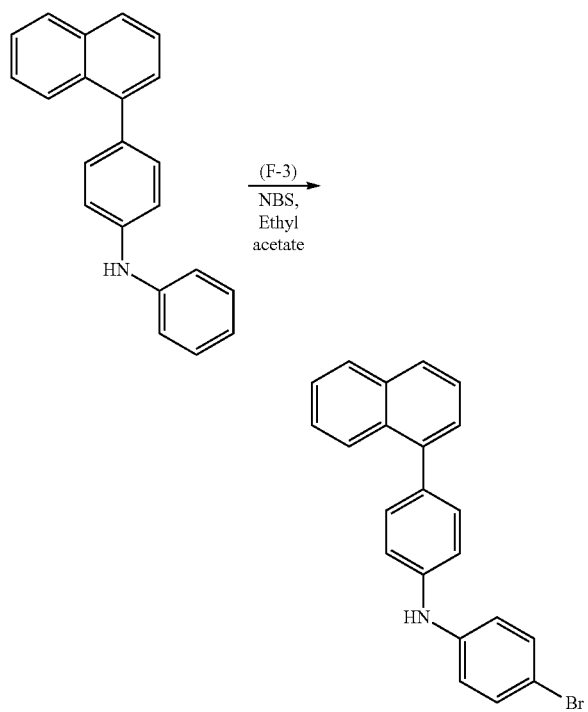 [SMILES: c1ccc(Nc2ccc(-c3cccc4ccccc34)cc2)cc1 ; "(F-3)" ; Brc1ccc(Nc2ccc(-c3cccc4ccccc34)cc2)cc1]

The compound which was obtained through Step 3 was measured by a nuclear magnetic resonance method (NMR). The measurement data are shown below. From the measurement results, it was found that BrNBA that is one embodiment of the halogenated diarylamine compound represented by the general formula (G1) can be obtained.

$^1$H NMR (CDCl$_3$, 300 MHz): δ (ppm)=5.87 (s, 1H), 7.04 (d, J=8.7, 2H), 7.18 (d, J=8.7, 2H), 7.38-7.55 (m, 8H), 7.84 (d, J=8.1, 1H), 7.80 (d, J=7.8, 1H), 7.98 (d, J=7.8, 1H).

At this time, the fourth position of phenylamine of 4-(1-naphthyl)diphenylamine, which is a diarylamine compound, was specifically brominated. Thus, BrNBA which is a halogenated diarylamine compound which was a desired substance can be obtained with high purity in a high yield. The above description reveals that as for the diarylamine compound described in Embodiment 2, the fourth position of phenylamine was specifically-halogenated, so that the halogenated diarylamine compound which was a desired substance can be obtained with high purity in a high yield.

Example 2

Synthesis Example 2

In this example, a synthesis example of a diarylamine compound using, as a source material, a halogenated diarylamine compound which is one embodiment of the present invention is described. Specifically, a synthesis method of 4-(1-naphthyl)-4'-(9-phenyl-9H-carbazol-3-yl)diphenylamine (abbreviation: PCBNA) which is a diarylamine compound is described. A structure of PCBNA is described below. This example is one embodiment of synthesis of PCBNA which is a diarylamine compound, using BrNBA which is the halogenated diarylamine compound synthesized in Synthesis Example 1, as a source material.

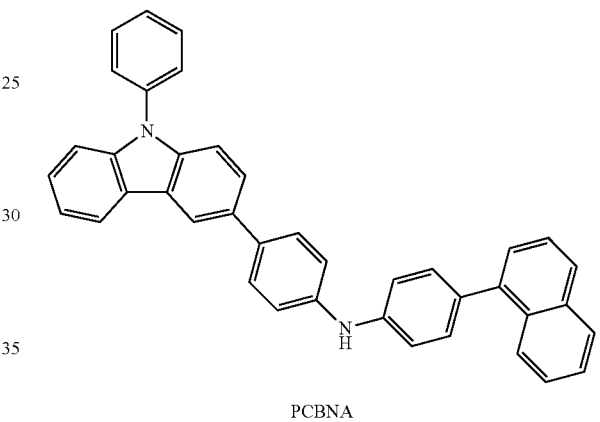

PCBNA

Step 1: Synthesis of 4-(1-naphthyl)-4'-(9-phenyl-9H-carbazol-3-yl)diphenylamine (Abbreviation: PCBNA)

Into a 100-mL three-neck flask, 720 g (1.9 mmol) of 4-bromo-4'-(1-naphthyl)diphenylamine, 570 mg (1.9 mmol) of 9-phenyl-9H-carbazol-3-boronic acid, 4.0 mg (0.02 mmol) of palladium(II) acetate, and 6.0 mg (0.02 mmol) of tris(o-tolyl)phosphine were put, and 15 mL of toluene, 2 mL of ethanol, and 1.3 mL of a potassium carbonate solution (2 mol/L) were added to this mixture. This mixture was degassed while being stirred under reduced pressure. After that, the mixture was stirred under a nitrogen atmosphere at 90° C. for 6 hours to be reacted.

After the reaction, 150 mL of toluene was added to this reaction mixture solution, and this suspension was filtrated through Florisil and Celite. The obtained filtrate was washed with water, and magnesium sulfate was added thereto to adsorb moisture. This suspension was filtrated, and the obtained filtrate was concentrated and purified by silica gel column chromatography (developing solvent is toluene:hexane:ethyl acetate=4:5:1). The obtained fraction was concentrated, and hexane was added thereto. The mixture was irradiated with ultrasonic wave and then recrystallized, so that 800 mg of a white powder which was a desired substance was obtained in a yield of 80%. A reaction of the above synthesis method is shown in the following scheme (F-4).

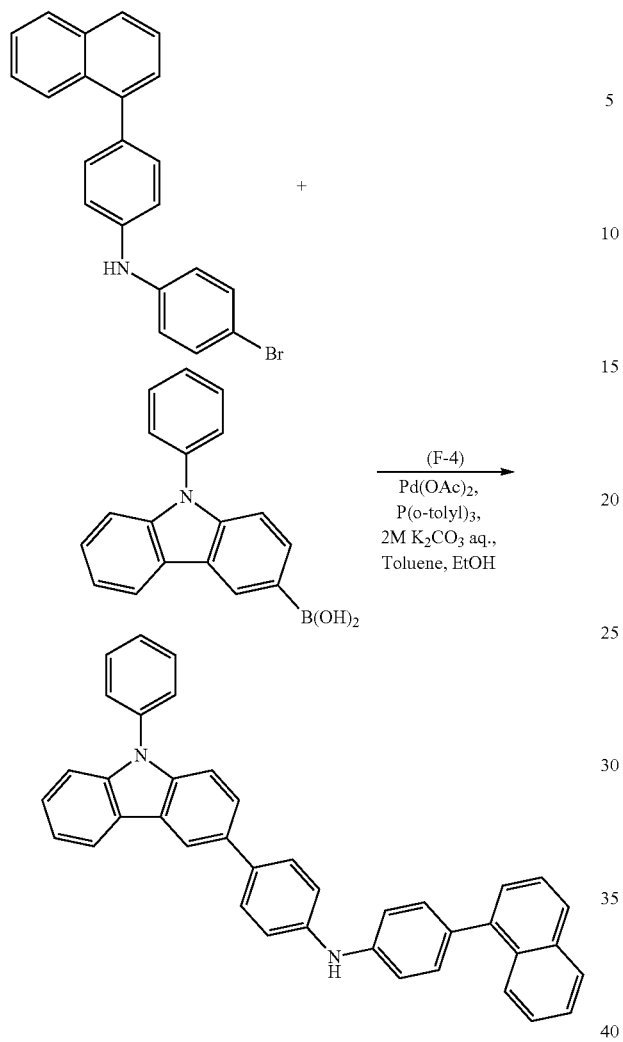

An Rf value of the desired substance by a silica gel thin layer chromatography (TLC) (developing solvent is ethyl acetate:hexane=1:10) was 0.14, and that of 4-bromo-4'-(1-naphthyl)diphenylamine was 0.25.

Figure 3A:
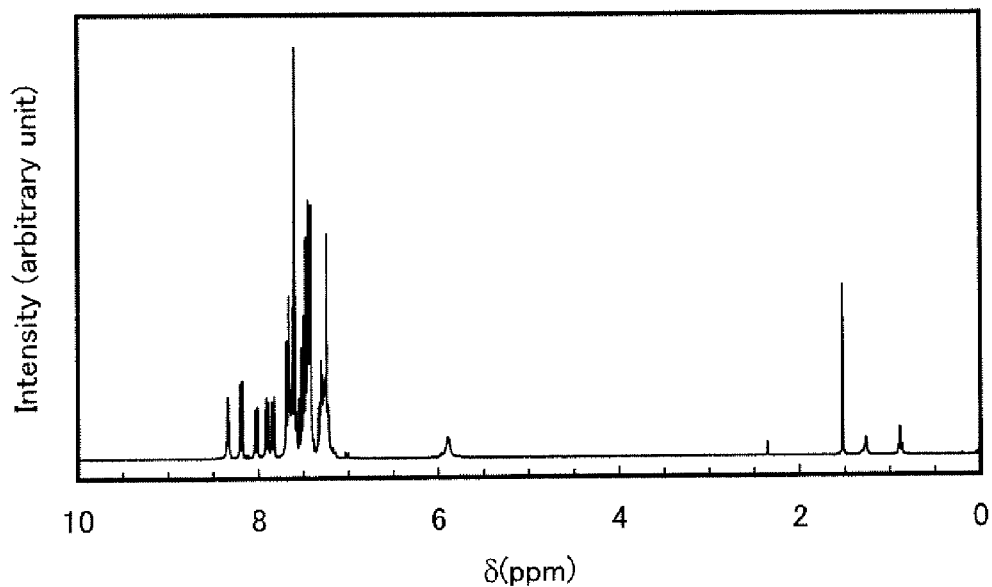
FIGS. 3A and 3B are NMR charts of PCBNA.
Figure 3B:
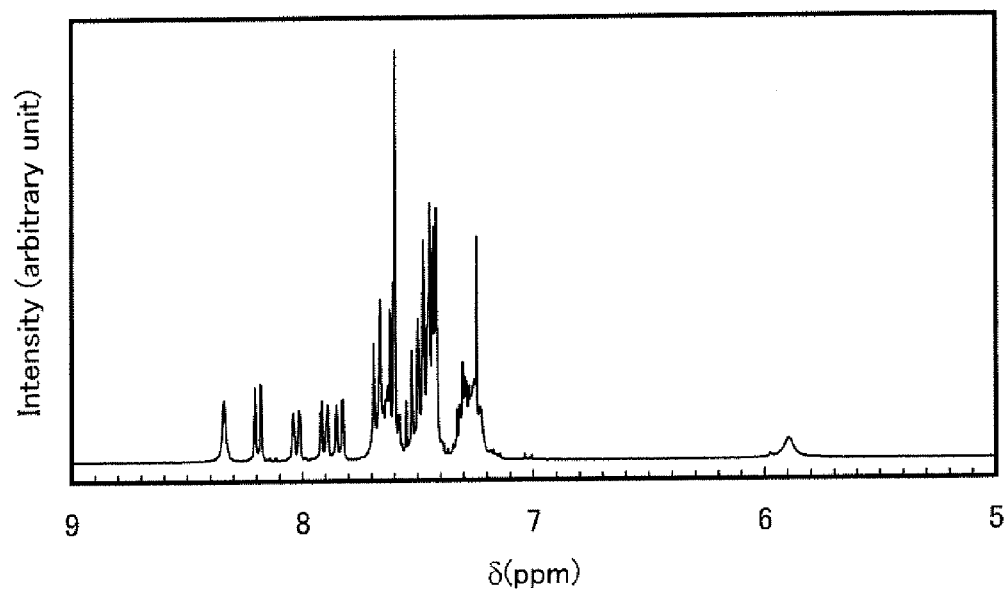

The compound which was obtained through Step 1 was measured by a nuclear magnetic resonance method ($^1$H NMR). The measurement data are shown below. FIGS. 3A and 3B are $^1$H NMR charts. FIG. 3B is an enlarged chart showing a range of 5 ppm to 9 ppm of FIG. 3A. From the measurement results, it was found that PCBNA (abbreviation) that is the diarylamine compound described in Embodiment 2 can be obtained.

$^1$H NMR (CDCl$_3$, 300 MHz): δ (ppm)=5.89 (s, 1H), 7.22-7.69 (m, 22H), 7.84 (d, J=8.4 Hz, 1H), 7.89-7.92 (m, 1H), 803 (d, J=7.8 Hz, 1H), 8.20 (d, J=7.8 Hz, 1H), 8.34 (s, 1H).

Example 3

Synthesis Example 3

In this example, a synthesis example of a triarylamine compound using, as a source material, a halogenated diarylamine compound which is one embodiment of the present invention is described. Specifically, a synthesis method of 4-(1-naphthyl)-4'-(10-phenyl-9-anthryl)-4''-(9-phenyl-9H-carbazol-3-yl)triphenylamine (abbreviation: PCBNAPA) which is a triarylamine compound is described. A structure of PCBNAPA is described below. This example is one embodiment of synthesis of PCBNAPA using PCBNA as a source material. PCBNA is a diarylamine compound synthesized using, as a source material, BrNBA which is the halogenated diarylamine compound synthesized in Synthesis Example 1.

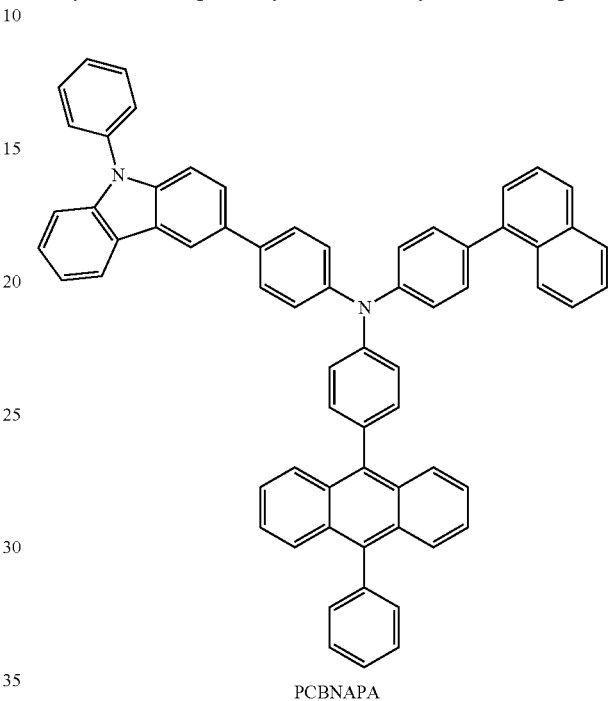

PCBNAPA

Step 1: Synthesis of 4-(1-naphthyl)-4'-(10-phenyl-9-anthryl)-4''-(9-phenyl-9H-carbazol-3-yl)triphenylamine (Abbreviation: PCBNAPA)

Into a 50-mL three-neck flask, 0.45 g (1.1 mmol) of 9-(4-bromophenyl)-10-phenylanthracene and 0.4 g (4.3 mmol) of sodium tert-butoxide were put, and the atmosphere in the flask was substituted by nitrogen. Then, 0.8 g (1.4 mmol) of PCBNA (abbreviation) dissolved in 10 mL of toluene was added to this mixture, and after that, 4.3 mL of toluene and 0.1 mL of tri(tert-butyl)phosphine (a 10 wt % hexane solution) were added thereto. This mixture was heated to 60° C., and then 23 mg (4.0 mmol) of bis(dibenzylideneacetone)palladium(0) was added. This mixture was stirred at 80° C. for 2 hours. After the stirring, the mixture was filtered through Celite, Florisil, and alumina to obtain a filtrate.

The resulting filtrate was concentrated to obtain a solid, and the solid was purified by silica gel column chromatography (developing solvent is hexane:toluene=3:7). Then the obtained fraction was concentrated to obtain a yellow solid which was a desired substance. The resulting solid was recrystallized with a mixed solvent of toluene and hexane, so that 1.07 g of a pale yellow powder which was a desired substance was obtained in a yield of 85%. The synthesis scheme of PCBNAPA is shown in the following (F-5).

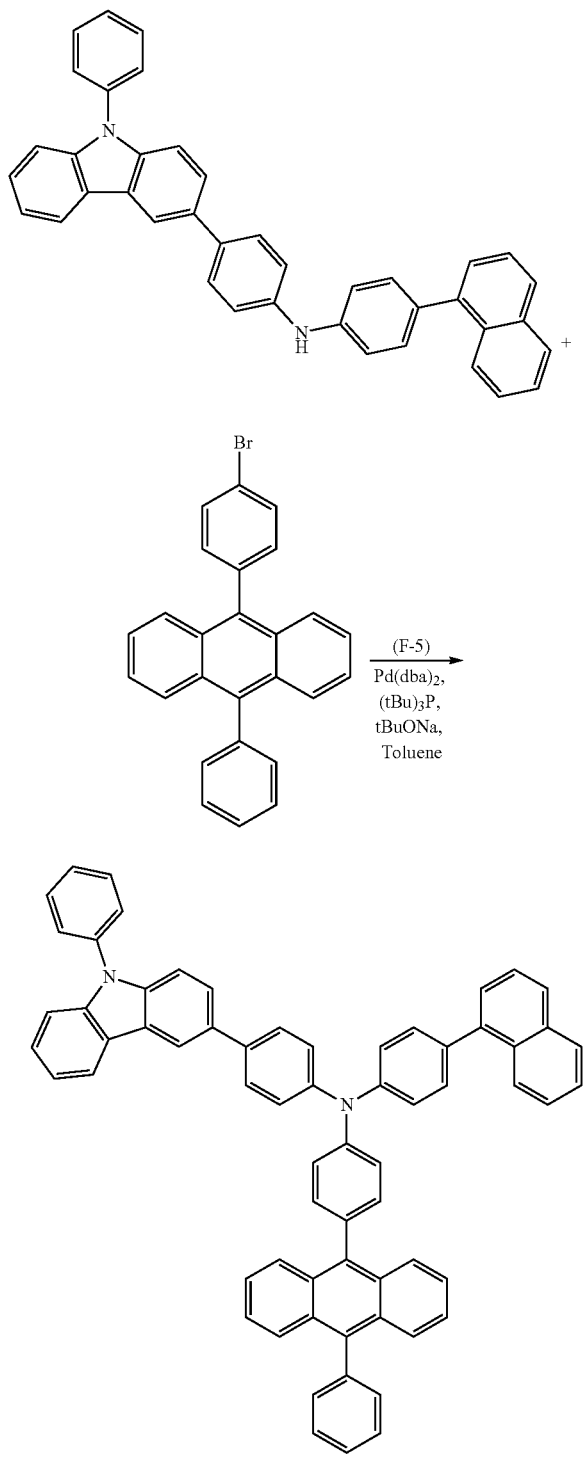

By a train sublimation method, 0.84 g of the obtained yellow solid was sublimated and purified. For sublimation purification conditions, the pale yellow solid was heated at 380° C. under a pressure of 4.5 Pa with a flow rate of argon gas of 5 mL/min. After the sublimation purification, 0.76 g of a yellow prismatic crystal which was the desired substance was recovered in a yield of 91%.

The thermogravimetry-differential thermal analysis (TG-DTA) of the obtained PCBNAPA was carried out. The measurement was conducted using a high vacuum differential type differential thermal balance (TG/DTA 2410SA, produced by Bruker AXS K.K.). The measurement was carried out under nitrogen stream (flow rate: 200 mL/min) and a normal pressure at a temperature rising rate of 10° C./min. From the relationship between weight and temperature (thermogravimetry), it was understood that the 5% weight loss temperature was higher than or equal to 500° C., which is indicative of high thermal stability.

The absorption spectrum and the emission spectrum of a toluene solution of PCBNAPA were measured. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation), and the solution was put into a quart cell to be measured. The absorption spectrum was obtained with an absorption spectrum measured by putting only toluene in a quartz cell subtracted. The absorption peak of the toluene solution was observed around 337 nm, 375 nm, and 397 nm. The maximum emission wavelength of this solution was 457 nm (excitation wavelength: 370 nm).

The absorption spectrum and the emission spectrum of a thin film of PCBNAPA were measured. The absorption spectrum was measured using an ultraviolet-visible spectrophotometer (V-550, produced by JASCO Corporation). The emission spectrum was measured using a fluorescence spectrophotometer (FS920, produced by Hamamatsu Photonics Corporation), and the solution was put into a quart cell. A sample thereof was prepared by evaporation on a quartz substrate to be measured. The absorption spectrum was obtained with an absorption spectrum measured by putting only toluene in a quartz cell subtracted. The absorption peak of the thin film PCBNAPA was observed around 339 nm, 357 nm, 375 nm, and 401 nm. The maximum emission wavelength was 476 nm (excitation wavelength: 401 nm) in the case of the thin film.

Figure 4A:
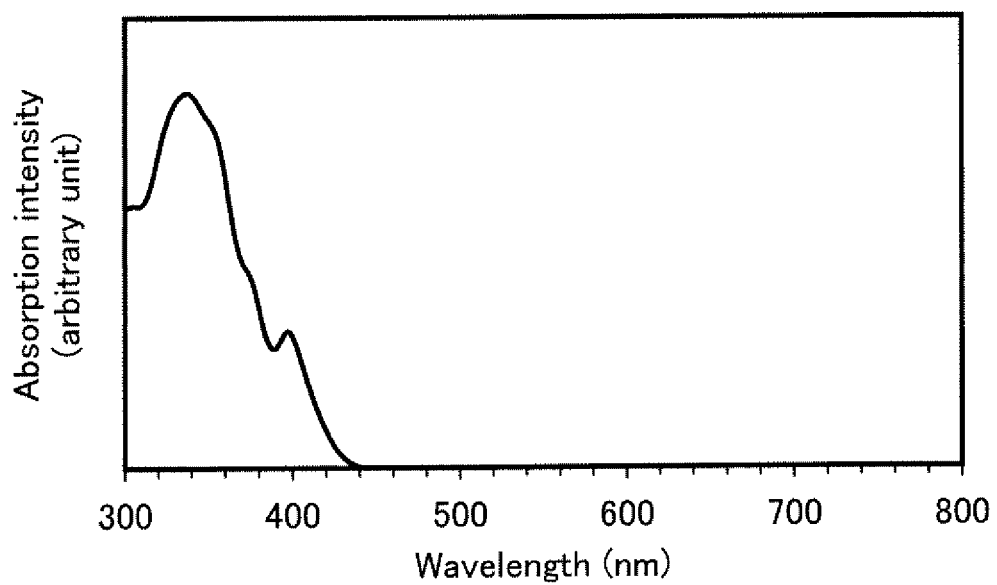
FIGS. 4A and 4B are graphs of an absorption spectrum and an emission spectrum of PCBNAPA in a toluene solution.
Figure 4B:
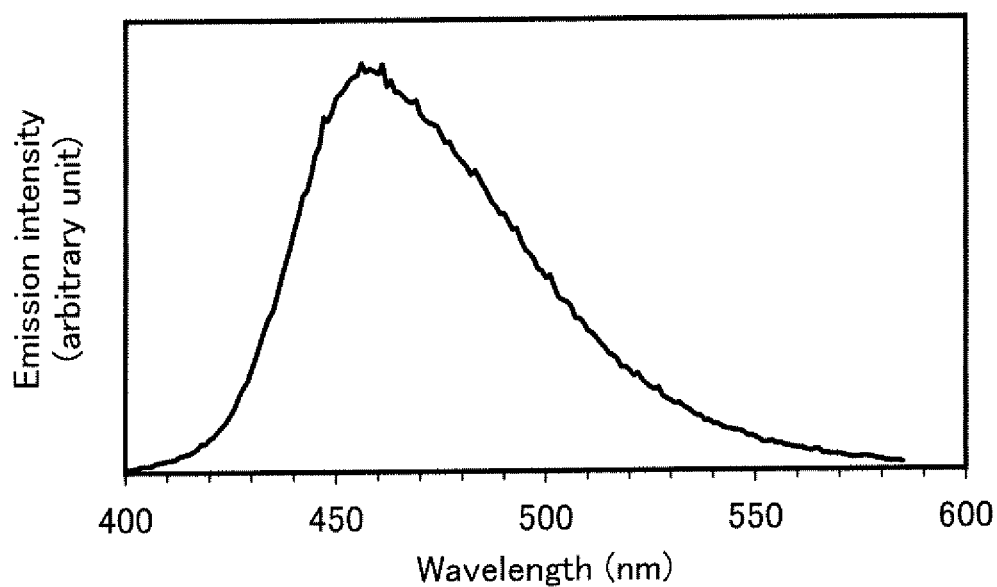
Figure 5A:
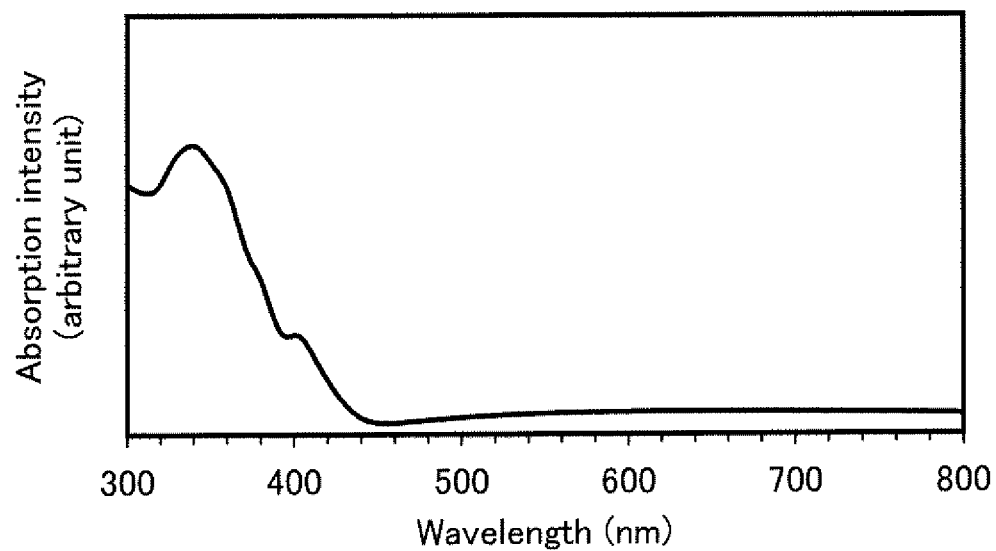
FIGS. 5A and 5B are graphs showing an absorption spectrum and an emission spectrum of PCBNAPA in a thin film.
Figure 5B:
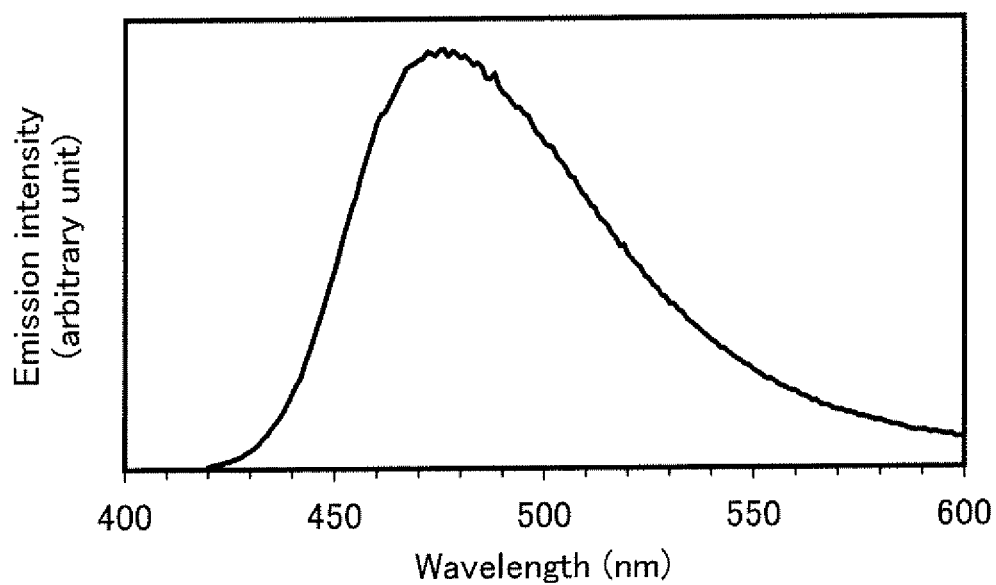

The obtained absorption spectrum and emission spectrum of the toluene solution are shown in FIGS. 4A and 4B, and the obtained absorption spectrum and emission spectrum of the thin film are shown in FIGS. 5A and 5B.

As discussed above, PCBNAPA represented by the structural formula (67) exhibits blue light emission of a sufficiently short wavelength with favorable chromaticity both in the toluene solution and in the thin film.

The oxidation characteristics and reduction characteristics of PCBNAPA were measured. The oxidation characteristics and reduction characteristics were measured by cyclic voltammetry (CV) measurement. Note that an electrochemical analyzer (ALS model 600A, produced by BAS Inc.) was used for the measurement.

The solution for the CV measurement was prepared by using dehydrated N,N-dimethylformamide (DMF) (catalog number: 22705-6, produced by Sigma-Aldrich Corp., 99.8%) as a solvent, dissolving tetra-n-butylammonium perchlorate (n-Bu$_4$NClO$_4$) (catalog number: T0836, produced by Tokyo Chemical Industry Co., Ltd.), which is a supporting electrolyte, to have a concentration of 100 mmol/L, and dissolving PCBNAPA to have a concentration of 1 mmol/L. A platinum electrode (a PTE platinum electrode, produced by BAS Inc.) was used as a working electrode; a platinum electrode (a VC-3 Pt counter electrode (5 cm), produced by BAS Inc., was used as an auxiliary electrode; and an Ag/Ag+ electrode (an RE5 nonaqueous solvent reference electrode, produced by BAS Inc.) was used as a reference electrode. The measurement was carried out at room temperature. The scan speed at the CV measurement was 0.1 V/s.

The reduction characteristics of PCBNAPA were evaluated by 100 measurement cycles where the potential of the working electrode with respect to the reference electrode was scanned from −1.22 V to −2.40 V and then scanned from −2.40 V to −1.22 V in each of the cycles. Similarly, the oxidation characteristics were evaluated by 100 measurement cycles where the potential was scanned from 0.28 V to 0.60 V and then scanned from 0.60 V to 0.28 V in each of the cycles.

Figure 6A:
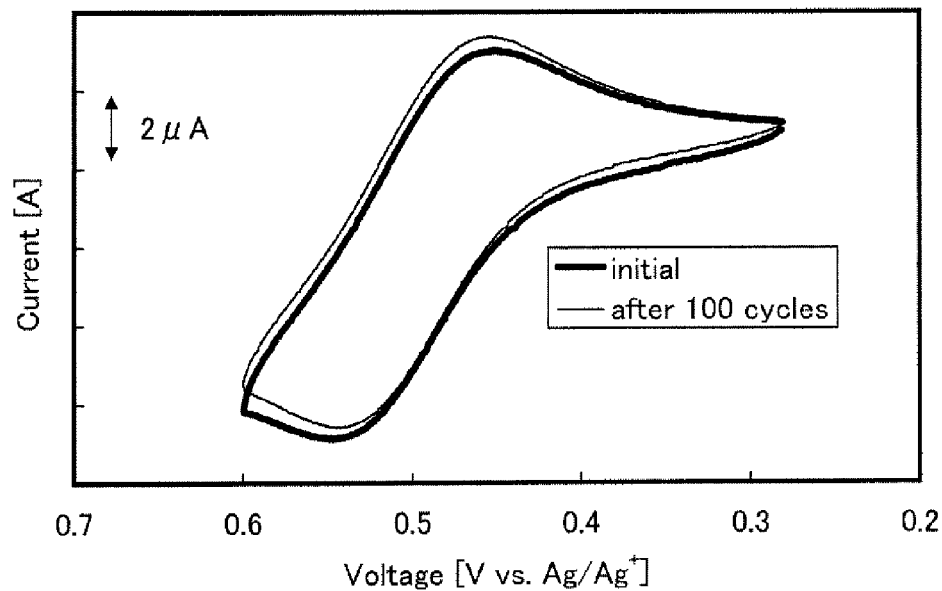
FIGS. 6A and 6B are CV charts of PCBNAPA.
Figure 6B:
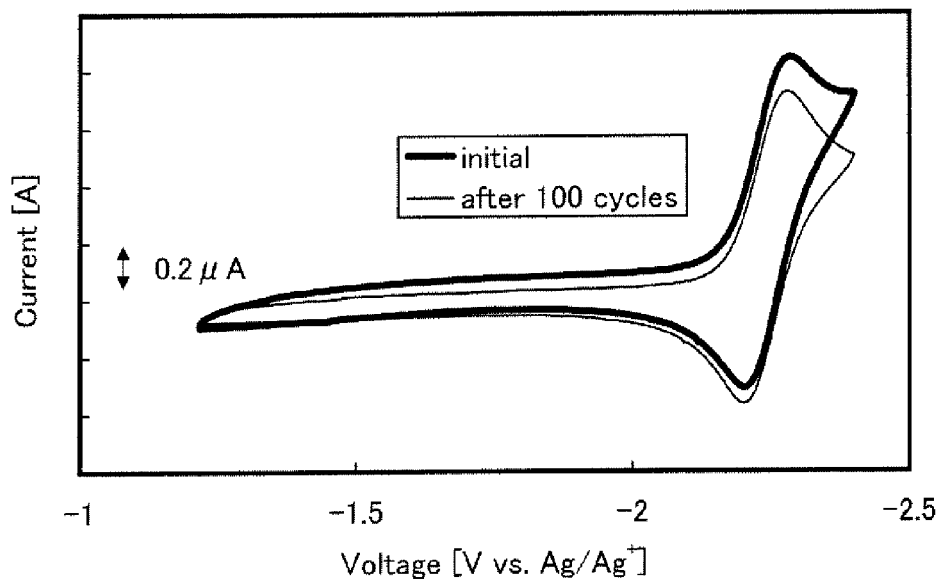

The peak current corresponding to the oxidation was observed around 0.50 eV (vs. Ag/Ae) and the peak current corresponding to the reduction was observed around −2.24 eV (vs. Ag/Ag+). The obtained spectra are shown in FIGS. 6A and 6B.

Although the scan was repeated as many as 100 cycles, PCBNAPA showed no significant change in the peak position of the CV curves in the oxidation and the reduction. The peak intensity remained 96% of the initial state on the oxidation side and 86% of the initial state on the reduction side. Thus, it was understood that PCBNAPA is relatively stable even when an oxidation from a neutral state to an oxidized state and a reduction from the oxidized state to the neutral state are repeated and when a reduction from the neutral state to a reduced state and an oxidation from the reduced state to the neutral state are repeated.

The results of the measurement of the thin film of PCB-NAPA by photoelectron spectrometry (AC-2, produced by Riken Keiki Co., Ltd.) under air indicate that the HOMO level of PCBNAPA is −5.47 eV. The absorption edge was obtained from Tauc plot, with an assumption of direct transition, using data on the absorption spectrum of the thin film, and the energy gap thereof was estimated to be 2.92 eV assuming that the absorption edge corresponds to the optical energy gap. The LUMO level was obtained to be −2.55 eV by calculation from the value of the energy gap and the HOMO level. Accordingly, it was found that PCBNAPA has a wide energy gap of 2.92 eV.

Example 4

Synthesis Example 4

In this example, a synthesis example of the halogenated diarylamine compound which is one embodiment of the present invention and represented by the structural formula (G1) in Embodiment 1 is described. Specifically, a synthesis example of 4-bromo-4'-(10-phenyl-9-anthryl)diphenylamine (abbreviation: BrAPA) represented by the structural formula (126) in Embodiment 1 is described. A structure of BrAPA is shown below.

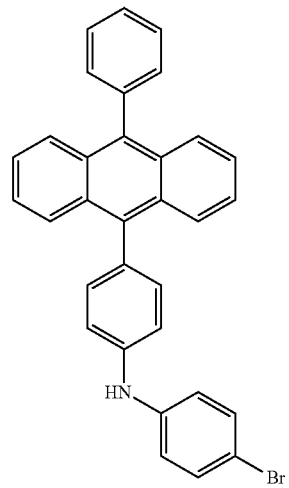

(126)

Step 1: Synthesis of
4-(10-Phenyl-9-anthryl)diphenylamine
(Abbreviation: APA

In a 100-mL three-neck flask, 2.0 g (5.0 mmol) of 9-(4-bromophenyl)-10-phenylanthracene, 0.4 g (5.0 mmol) of aniline, 0.7 g (7.0 mmol) of sodium tert-butoxide, and 30 mg (0.1 mmol) of bis(dibenzylideneacetone)palladium(0) were put, and the atmosphere of the flask was substituted by nitrogen. Then, 20 mL of toluene was added to this mixture. This mixture was degassed while being stirred under reduced pressure. After that, 0.3 mL (0.2 mmol) of tri(tert-butyl)phosphine (a 10 wt % hexane solution) was added thereto. This mixture was stirred under a nitrogen atmosphere at 110° C. for 2 hours to be reacted.

After the reaction, 150 mL of toluene was added to this reaction mixture solution, and this suspension was filtrated through Florisil, alumina, and Celite. The obtained filtrate was concentrated, and hexane was added thereto. The mixture was irradiated with ultrasonic wave and then recrystallized, so that 1.75 g of a yellow powder which was a desired substance was obtained in a yield of 83%. A reaction of the above synthesis method is shown in the following scheme (G-1).

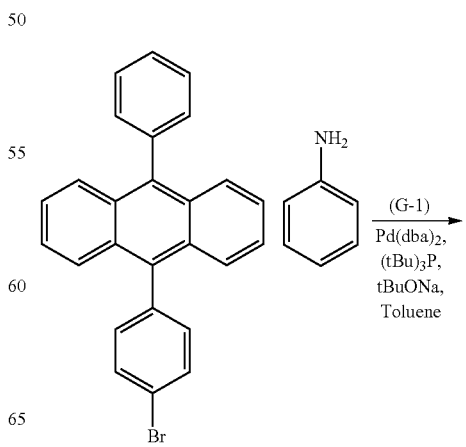

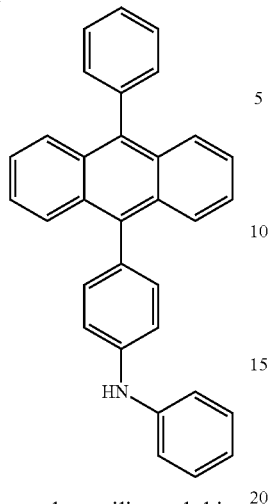

An Rf value of the desired substance by a silica gel thin layer chromatography (TLC) (developing solvent is ethyl acetate:hexane=1:10) was 0.24, and that of 9-(4-bromophenyl)-10-phenylanthracene was 0.52.

Figure 7A:
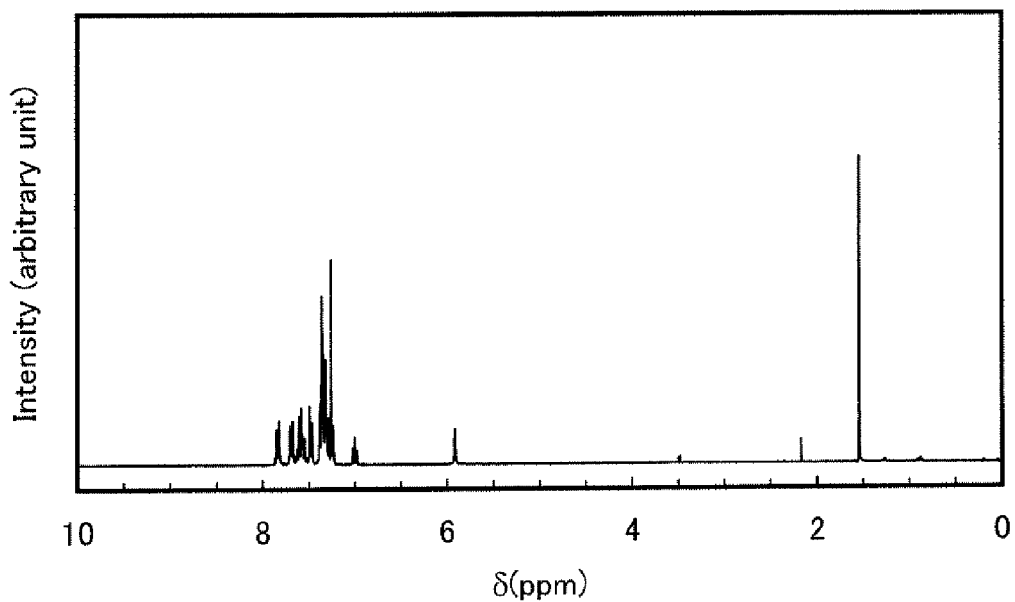
FIGS. 7A and 7B are $^1$H NMR charts of APA.
Figure 7B:
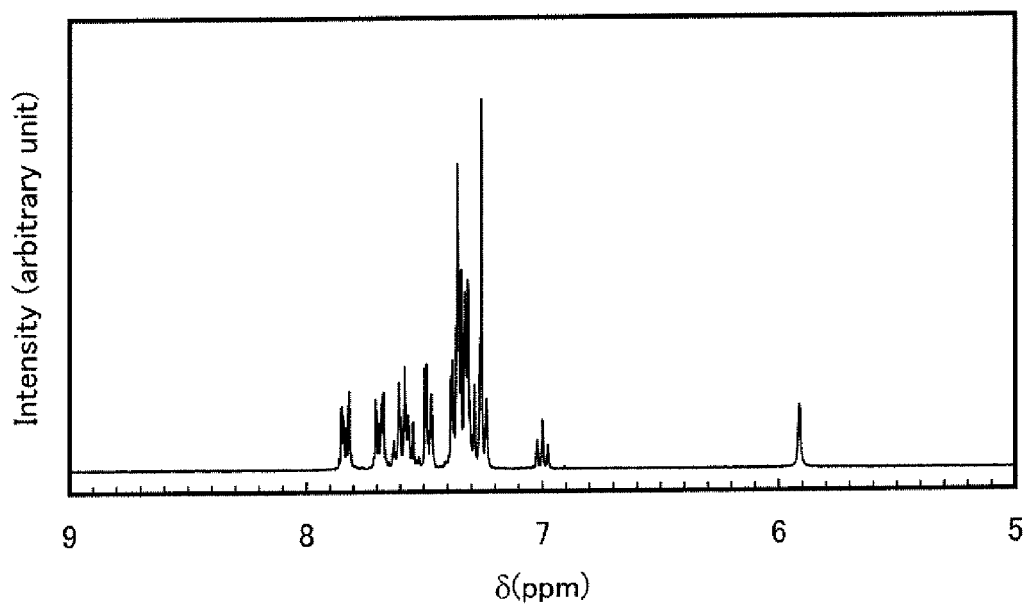

The compound which was obtained through Step 1 was measured by a nuclear magnetic resonance method ($^1$H NMR). The measurement data are shown below. FIGS. 7A and 7B are $^1$H NMR charts. FIG. 7B is an enlarged chart showing a range of 5 ppm to 9 ppm of FIG. 7A. From the measurement results, it was found that APA (abbreviation) that is the desired diarylamine compound can be obtained.

$^1$H NMR (CDCl$_3$, 300 MHz): δ (ppm)=5.91 (s, 1H), 7.00 (t, J=2.9, 1H), 7.23-7.39 (m, 12H), 7.46-7.50 (m, 2H), 7.54-7.63 (m, 3H), 7.67-7.71 (m, 2H), 7.82-7.85 (m, 2H).

Step 2: Synthesis of 4-bromo-4'-(10-phenyl-9-anthryl)diphenylamine (Abbreviation: BrAPA)

After 84 mg (0.2 mmol) of 4-(10-phenyl-9-anthryl)diphenylamine was dissolved in 5 mL of chloroform in a 20 mL conical flask, 36 mg (0.2 mmol) of N-bromo succinimide (abbreviation: NBS) was added to this solution. Then, this mixture was stirred at room temperature for an hour. After completion of the reaction, this mixture solution was washed with water, and magnesium sulfate was added thereto to adsorb moisture. This suspension was filtrated, and the obtained filtrate was concentrated. Hexane was added thereto. The mixture was irradiated with ultrasonic wave and then recrystallized, so that 400 mg of a pale green powder which was a desired substance was obtained in a yield of 40%. A reaction of the above synthesis method is shown in the following scheme (G-2).

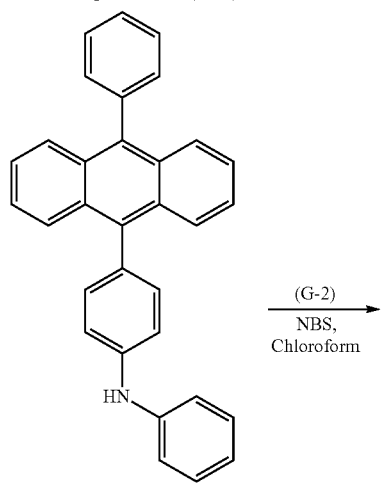

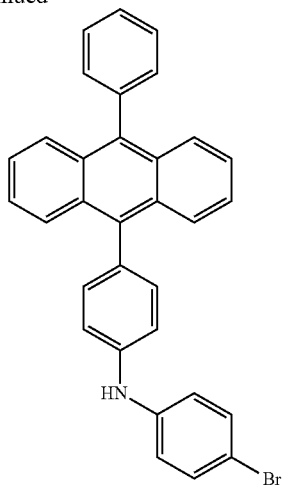

At this time, the fourth position of phenylamine of 4-(10-phenyl-9-anthryl)diphenylamine, which is a diarylamine compound, was specifically brominated. Thus, BrABA which is a halogenated diarylamine compound which was a desired substance can be obtained with high purity in a high yield. The above description reveals that as for the diarylamine compound of the present invention, the fourth position of phenylamine was specifically-halogenated, so that the halogenated diarylamine compound which was a desired substance can be obtained with high purity in a high yield.

Figure 8A:
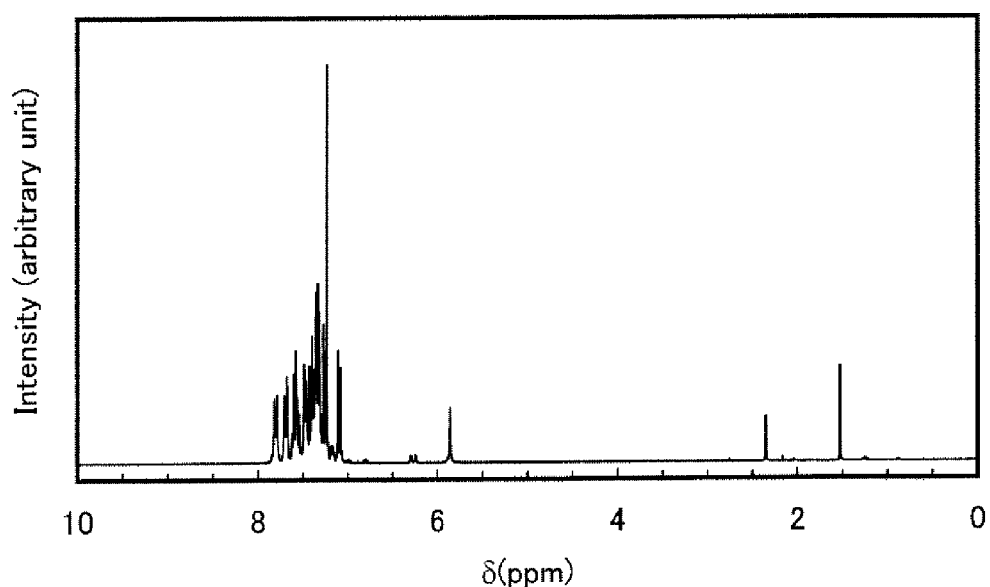
FIGS. 8A and 8B are $^1$H NMR charts of BrAPA.
Figure 8B:
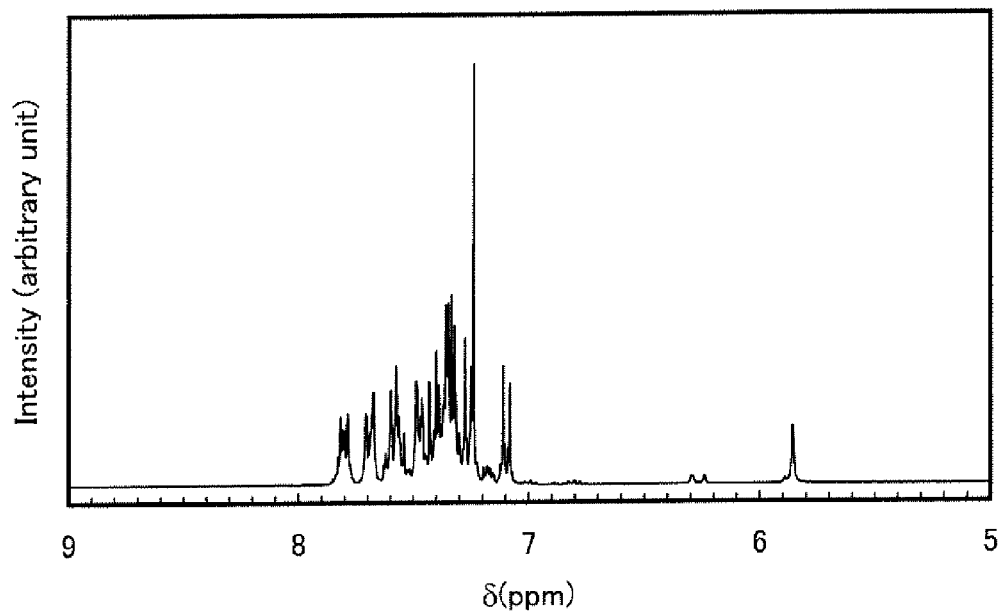

The compound which was obtained through Step 2 was measured by a nuclear magnetic resonance method ($^1$H NMR). The measurement data are shown below. FIGS. 8A and 8B are $^1$H NMR charts. FIG. 8B is an enlarged chart showing a range of 5 ppm to 9 ppm of FIG. 8A. From the measurement results, it was found that BrAPA (abbreviation) represented by the structural formula (126), which is one embodiment of the halogenated diarylamine compound of the present invention can be obtained.

$^1$H NMR (CDCl$_3$, 300 MHz): δ (ppm)=5.89 (s, 1H), 7.12 (d, J=8.4, 2H), 7.26-7.49 (m, 12H), 7.55-7.63 (m, 3H), 7.68-7.71 (m, 2H), 7.79-7.82 (m, 2H).

Example 5

In this example, another synthesis method of 4-bromo-4'-(10-phenyl-9-anthryl)diphenylamine (abbreviation: BrAPA) represented by the structural formula (126) in Example 4 is described.

Synthesis Example 5

Step 1: Synthesis of 4-(10-phenyl-9-anthryl)diphenylamine (Abbreviation: APA)

Synthesis was performed in a manner similar to that of Step 1 in Example 4.

Step 2: Synthesis of 4-bromo-4'-(10-phenyl-9-anthryl)diphenylamine (Abbreviation: BrAPA)

First, 840 mg (2.0 mmol) of 4-(10-phenyl-9-anthryl)diphenylamine was dissolved in 80 mL of ethyl acetate in a 100-mL conical flask, and then, 360 mg (2.0 mmol) of N-bromo succinimide (abbreviation: NBS) was added thereto. Then, this mixture was stirred at room temperature for 24 hours. After completion of the reaction, this mixture solution was washed with water, and magnesium sulfate was added thereto to adsorb moisture. This suspension was filtrated, and the obtained filtrate was concentrated. Hexane was added thereto. The mixture was irradiated with ultrasonic wave and then recrystallized, so that 700 g of a pale green powder which was a desired substance was obtained in a yield of 70%. A reaction of the synthesis method is shown in the following scheme (G-3).

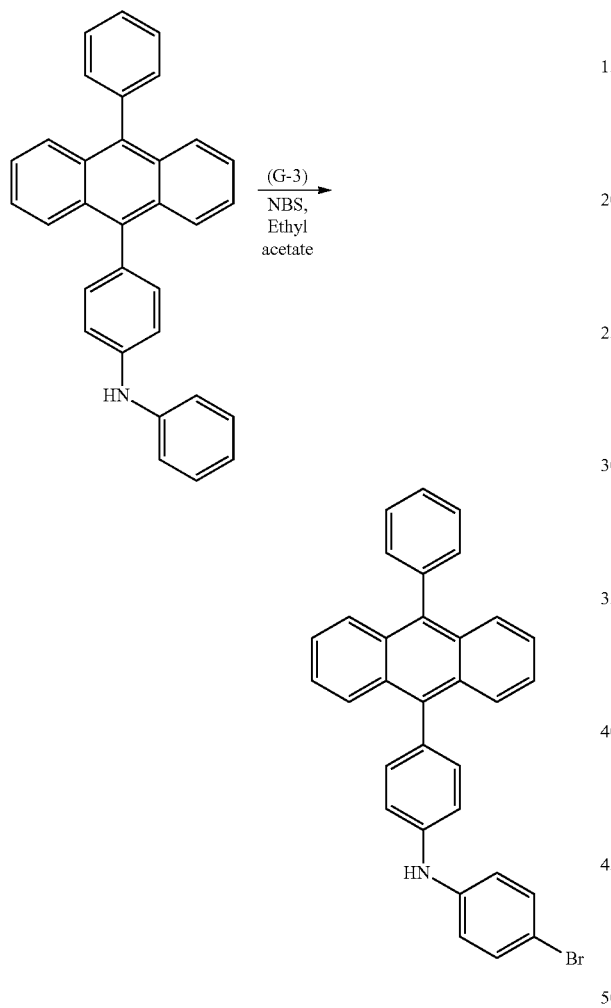

At this time, the fourth position of phenylamine of 4-(1-naphthyl)diphenylamine which is a diarylamine compound was specifically brominated. Thus, BrNBA which is a halogenated diarylamine compound which was a desired substance can be obtained with high purity in a high yield. The above description reveals that as for the diarylamine compound of the present invention, the fourth position of phenylamine was specifically-halogenated, so that the halogenated diarylamine compound which was a desired substance can be obtained with high purity in a high yield.

According to Step 2 in Example 4 and Step 2 in Example 5, the following was confirmed: NBS that is a halogenating agent acts in a polar solvent such as chloroform or ethyl acetate (the dielectric constant of chloroform is 4.8 and the dielectric constant of ethyl acetate is 6.0), whereby a specified position (the fourth position of phenylamine of a compound) is specifically-halogenated (brominated in this case)

Example 6

Figure 9A:
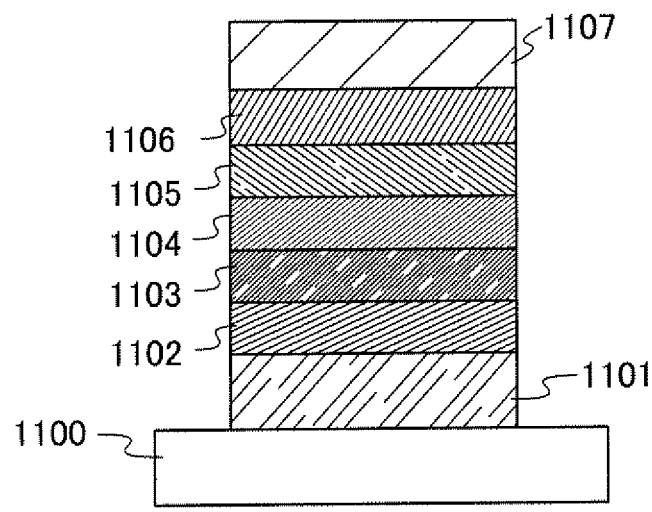
FIGS. 9A and 9B are conceptual diagrams of a light-emitting element 1 and a light-emitting element 2.
Figure 9B:
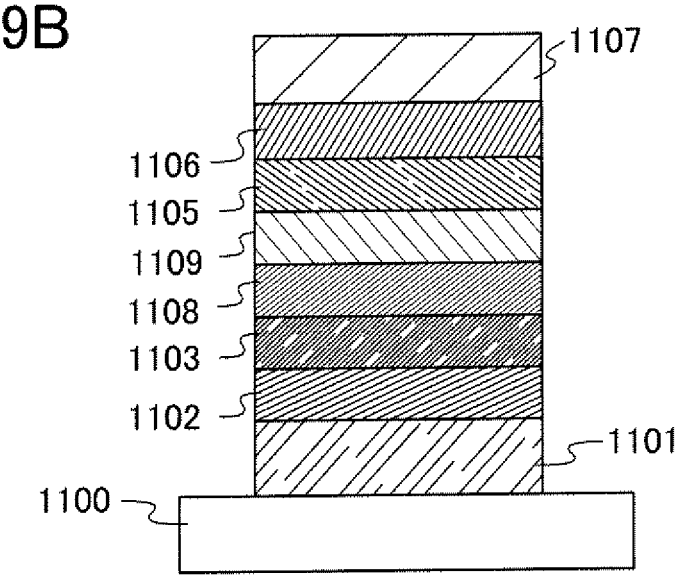

In this example, an example of a light-emitting element of one embodiment of the present invention is described with reference to FIGS. 9A and 9B. Chemical formulae of materials used in this example are shown below.

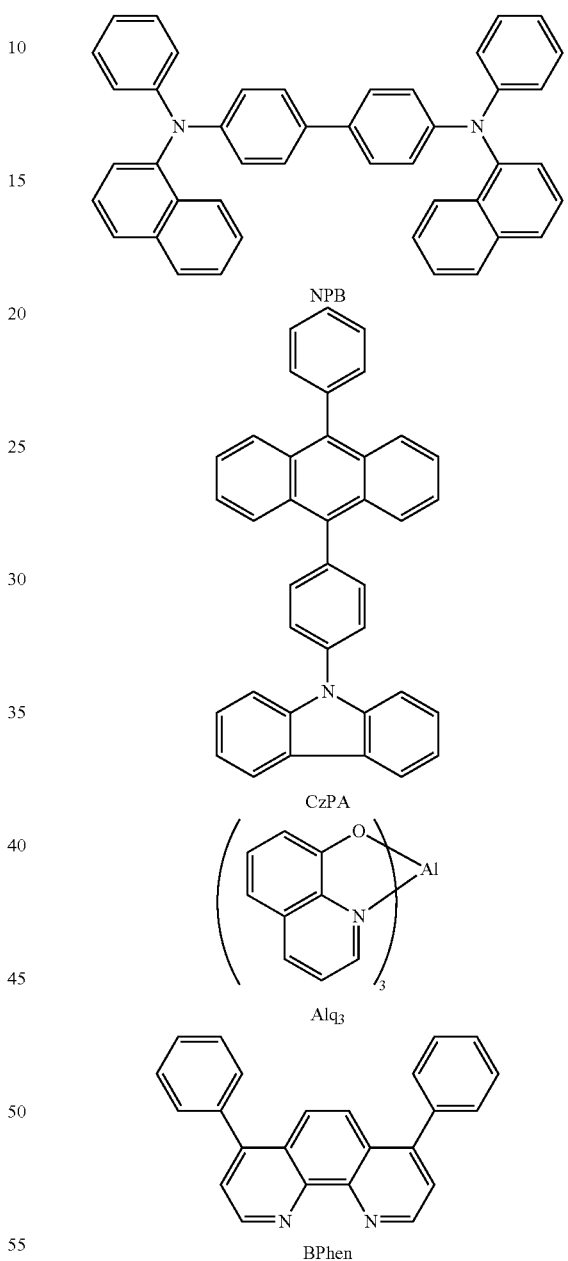

(Light-Emitting Element 1)

The structure of a light-emitting element 1 is described with reference to FIG. 9A. First, indium tin oxide containing silicon oxide was deposited over a glass substrate 1100 by a sputtering method to form a first electrode 1101. The thickness was 110 nm and the electrode area was 2 mm×2 mm.

Next, the glass substrate 1100 was fixed to a substrate holder provided in a vacuum evaporation apparatus in such a way that a surface of the glass substrate 1100, over which the first electrode 1101 was formed, faced downward, and then the pressure was reduced to about 10$^{-4}$ Pa. Then, 4,4'-bis[N-(1-naphthyl)-N-phenylamino]biphenyl (abbreviation: NPB) and molybdenum(VI) oxide were co-evaporated over the first electrode 1101, whereby a layer 1102 containing a composite material of an organic compound and an inorganic compound was formed. The film thickness of the layer 1102 was set to 50 nm, and the weight ratio between NPB and molybdenum oxide (=NPB:molybdenum oxide) was adjusted to 4:1. Note that the co-evaporation method is an evaporation method in which evaporation of a plurality of materials is performed from a plurality of evaporation sources at the same time in one treatment chamber.

Next, NPB was deposited to a thickness of 10 nm over the layer 1102 containing the composite material by the evaporation method utilizing resistive heating, whereby a hole-transport layer 1103 was formed.

Further, by co-evaporation of 9-[4-(10-phenyl-9-anthryl)phenyl]-9H-carbazole (abbreviation: CzPA) and PCBNAPA, a light-emitting layer 1104 was formed to a thickness of 30 nm over the hole-transport layer 1103. The weight ratio of CzPA to PCBNAPA was adjusted so as to be 1:0.1 (=CzPA:PCBNAPA).

Then, tris(8-quinolinolato)aluminum (abbreviation: Alq) was deposited to a thickness of 10 nm over the light-emitting layer 1104, and bathophenanthroline (abbreviation: BPhen) was deposited to a thickness of 20 nm over the Alq layer by the evaporation method utilizing resistive heating to form an electron-transport layer 1105 formed using Alq and BPhen.

Furthermore, lithium fluoride was deposited to a thickness of 1 nm over the electron-transport layer 1105, whereby an electron-injection layer 1106 was formed.

Lastly, aluminum was deposited to a thickness of 200 nm over the electron-injection layer 1106 by the evaporation method utilizing resistive heating to form a second electrode 1107. Accordingly, the light-emitting element 1 was manufactured.

Figure 10:
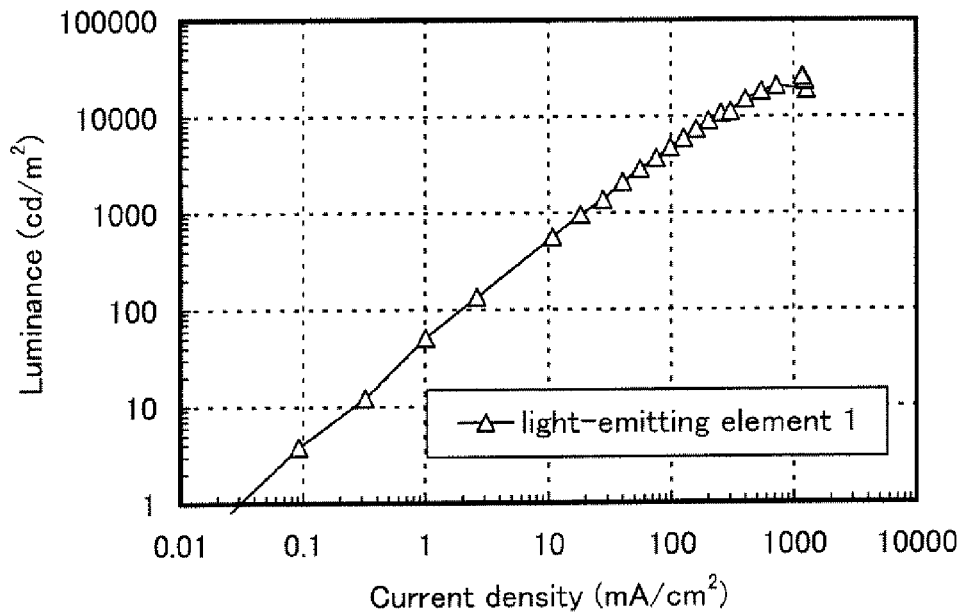
FIG. 10 is a graph showing current density-luminance characteristics of the light-emitting element 1.
Figure 11:
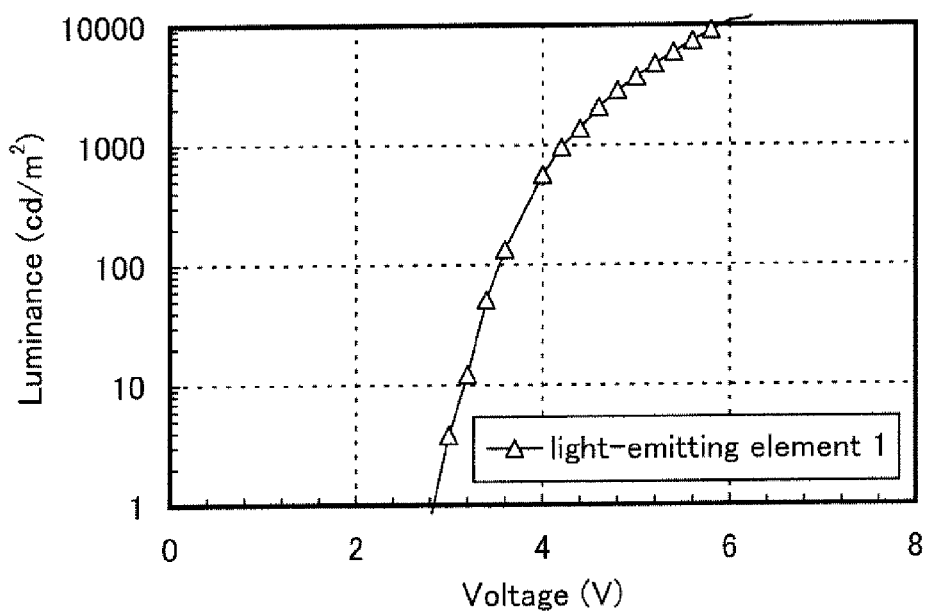
FIG. 11 is a graph showing voltage-luminance characteristics of the light-emitting element 1.
Figure 12:
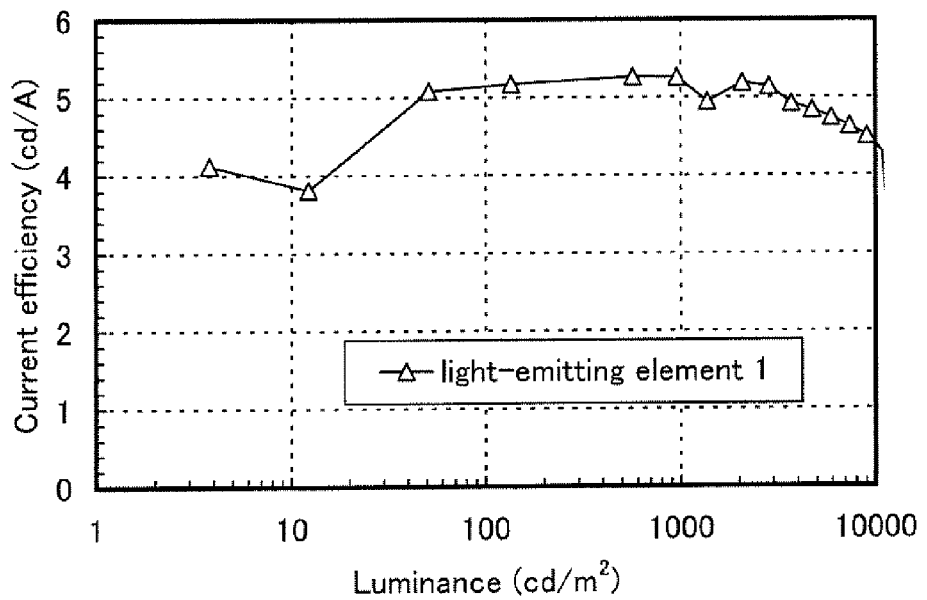
FIG. 12 is a graph showing luminance-current-efficiency characteristics of the light-emitting element 1.
Figure 13:
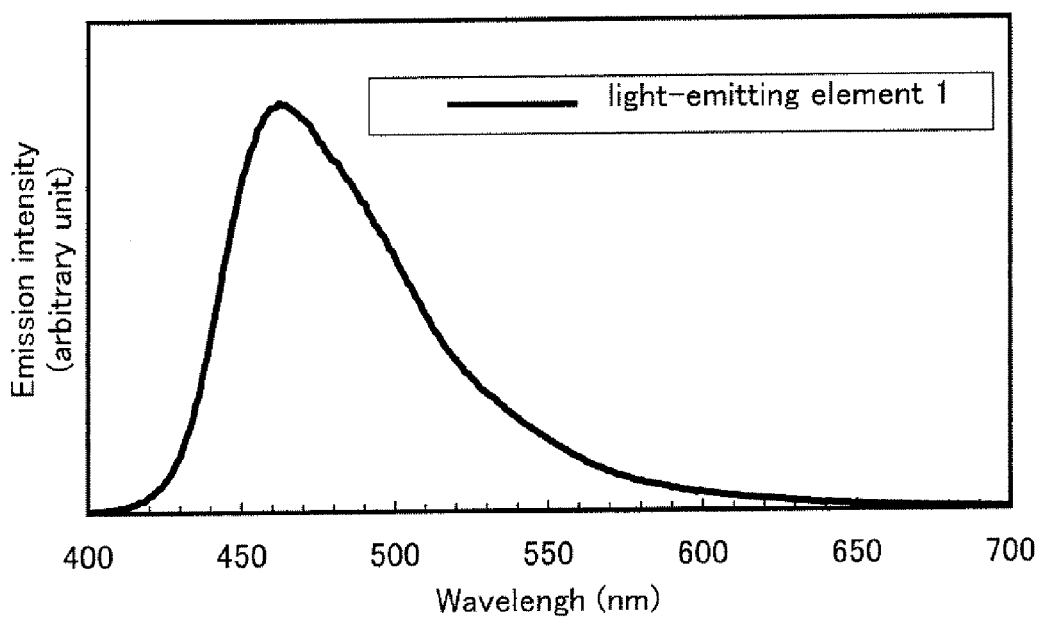
FIG. 13 is a graph showing an emission spectrum of the light-emitting element

FIG. 10 shows the current density-luminance characteristics of the light-emitting element 1. FIG. 11 shows the voltage-luminance characteristics thereof. FIG. 12 shows the luminance-current efficiency characteristics thereof. FIG. 13 shows an emission spectrum at a current of 1 mA. From FIG. 13, it is understood that the light emission of the light-emitting element 1 originates from PCBNAPA. The CIE chromaticity coordinates of the light-emitting element 1 at a luminance of 960 cd/m$^2$ are (x, y)=(0.16, 0.20), which exhibits blue emission with high color purity. FIG. 12 reveals that current efficiency of the light-emitting element 1 at a luminance of 960 cd/m$^2$ is 5.3 cd/A, which is indicative of high current efficiency of the light-emitting element 1. FIG. 11 shows that the driving voltage at 960 cd/m$^2$ is 4.2 V, and power efficiency is 3.9 μm/W. From these results, it is found that a voltage required to obtain a certain luminance is low and power consumption is also low in the case of the light-emitting element 1.

Figure 14:
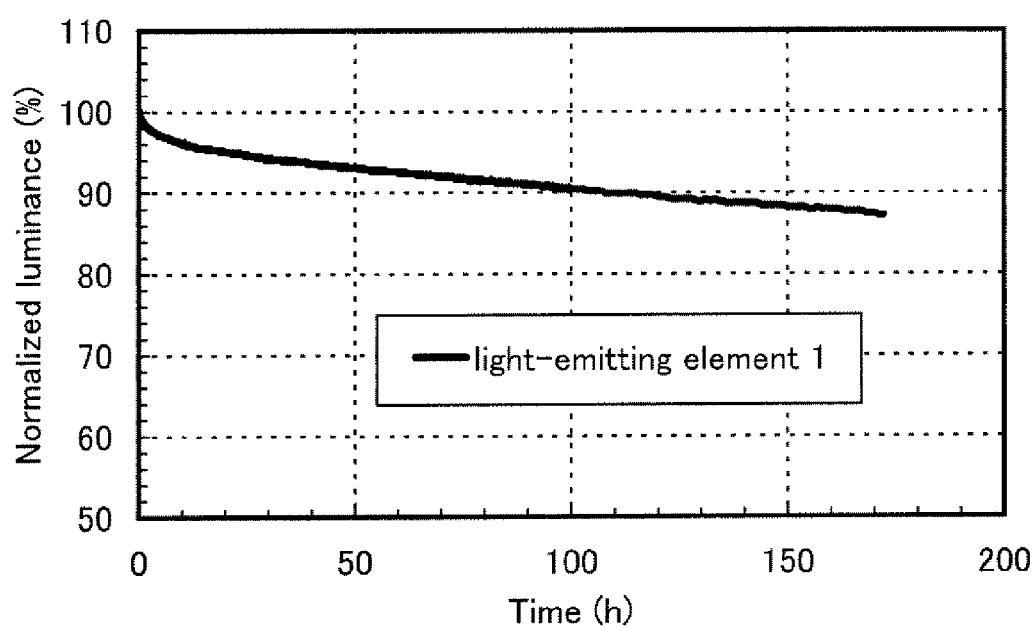
FIG. 14 is a graph showing time-normalized luminance characteristics of the light-emitting element 1.

Next, a reliability test of the light-emitting element 1 was carried out. Results of the reliability test are shown in FIG. 14. In FIG. 14, the vertical axis represents normalized luminance (%) on the assumption that an initial luminance is 100%, and the horizontal axis represents driving time (h) of the light-emitting element. The reliability test was carried out by driving the light-emitting element 1 of this example under the conditions that the initial luminance was set at 1000 cd/m$^2$ and the current density is constant. FIG. 14 shows that the light-emitting element 1 keeps 88% of the initial luminance after the driving for 150 hours. Therefore, it was confirmed that the light-emitting element 1 is indicative of high reliability. Thus, it was found that with the use of the triarylamine compound, which can be synthesized using the halogenated diarylamine compound of one embodiment of the present invention, a light-emitting element with long lifetime can be obtained.

Example 7

In this example, an example of a light-emitting element of one embodiment of the present invention is described with reference to FIG. 9B. Materials used in this example are the same as those used in Example 6.
(Light-Emitting Element 2)

First, over the glass substrate 1100, the first electrode 1101, the layer 1102 containing a composite material of an organic compound and an inorganic compound, and the hole-transport layer 1103 were formed in a manner similar to that of the light-emitting element 1 in Example 6.

Next, PCBNAPA was evaporated to a thickness of 20 nm over the hole-transport layer 1103 to form a first light-emitting layer 1108.

Further, by co-evaporation of CzPA and PCBNAPA, a second light-emitting layer 1109 with a thickness of 30 nm was formed over the first light-emitting layer 1108. The weight ratio of CzPA to PCBNAPA was adjusted to 1:0.05 (=CzPA:PCBNAPA).

Then, Alq was deposited over the second light-emitting layer 1109 to a thickness of 30 nm by the evaporation method utilizing resistive heating to form an electron-transport layer 1105.

Next, over the electron-transport layer 1105, the electron-injection layer 1106 and the second electrode 1107 were formed in a manner similar to that of the light-emitting element 1 in Example 6, so that the light-emitting element 2 was manufactured.

Figure 15:
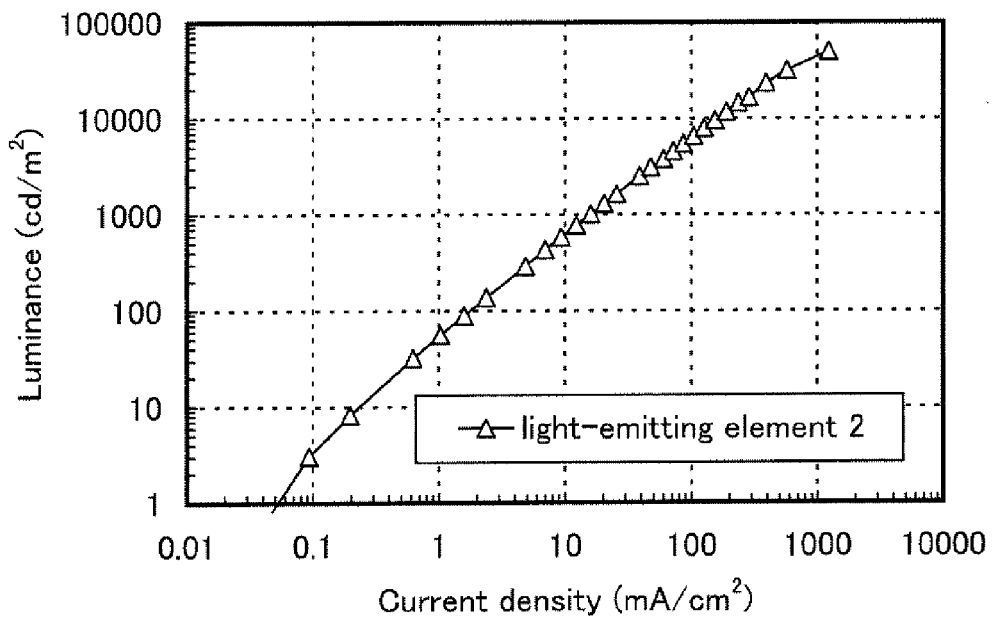
FIG. 15 is a graph showing current density-luminance characteristics of the light-emitting element 2.
Figure 16:
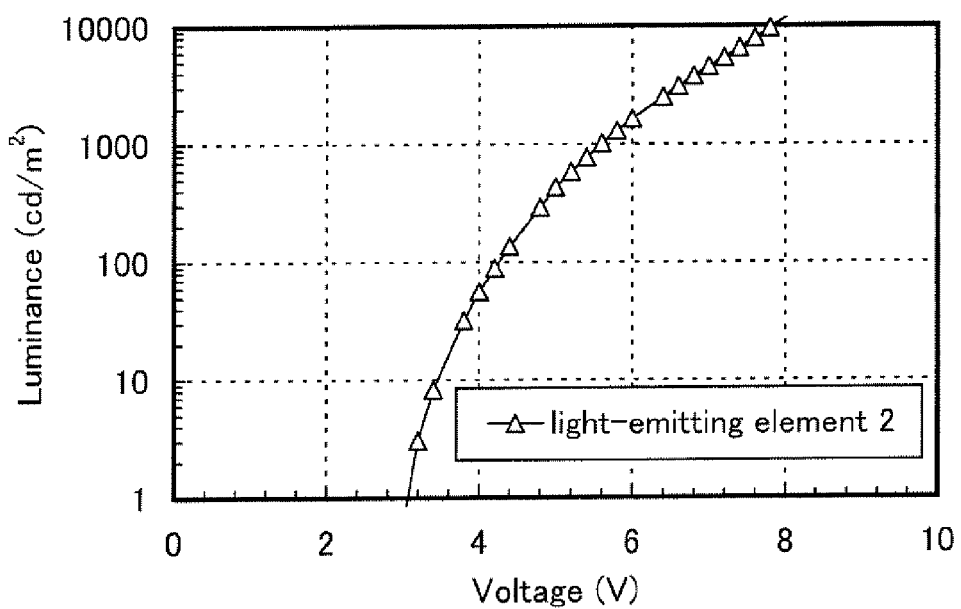
FIG. 16 is a graph showing voltage-luminance characteristics of the light-emitting element 2.
Figure 17:
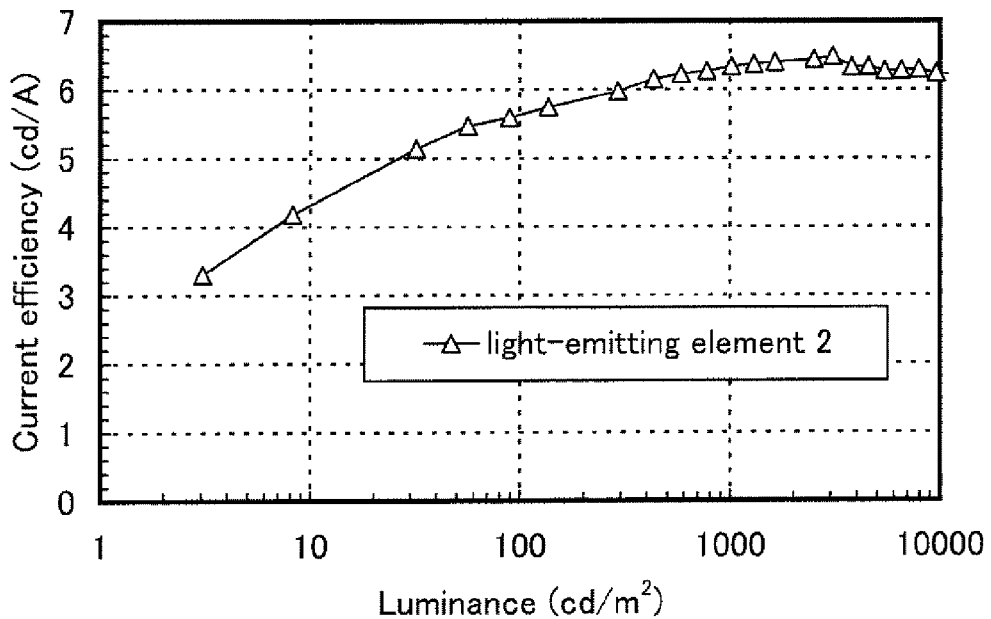
FIG. 17 is a graph showing luminance-current efficiency characteristics of the light-emitting element 2.
Figure 18:
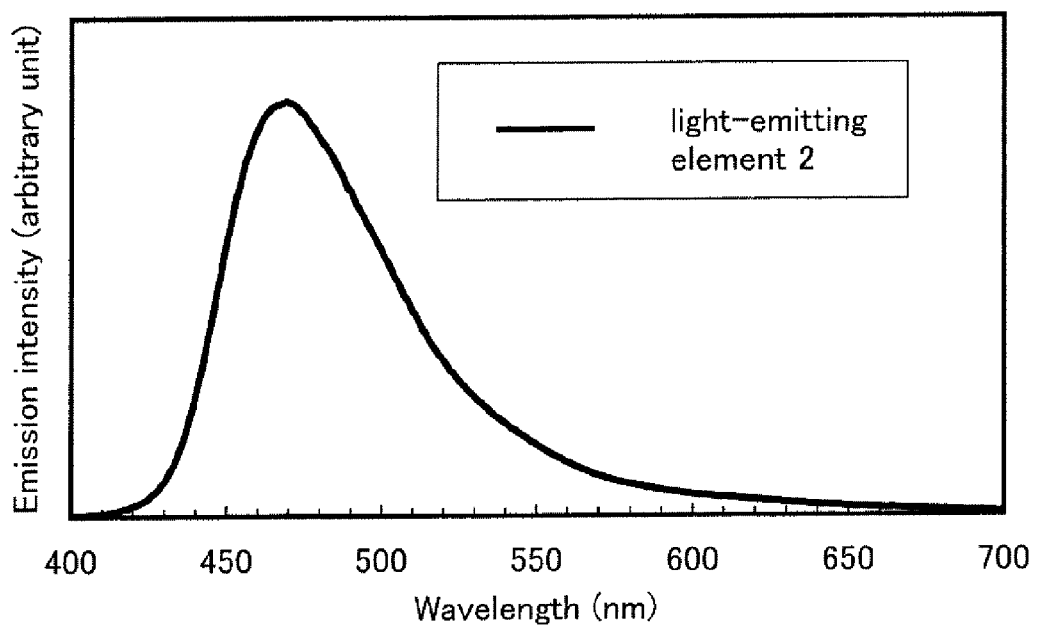
FIG. 18 a graph showing an emission spectrum of the light-emitting element 2.

FIG. 15 shows the current density-luminance characteristics of the light-emitting element 2. FIG. 16 shows the voltage-luminance characteristics thereof. FIG. 17 shows the luminance-current efficiency characteristics thereof. FIG. 18 shows an emission spectrum at a current of 1 mA. From FIG. 18, it is understood that the light emission of the light-emitting element 2 originates from PCBNAPA. The CIE chromaticity coordinates of the light-emitting element 2 at a luminance of 1010 cd/m$^2$ are (x, y)=(0.16, 0.22), which exhibits blue emission. FIG. 17 reveals that current efficiency of the light-emitting element 2 at a luminance of 1010 cd/m$^2$ is 6.3 cd/A, which is indicative of high current efficiency of the light-emitting element 2. FIG. 16 shows that the driving voltage at 1010 cd/m$^2$ is 5.6 V, and power efficiency is 3.9 lm/W. From these results, it is found that a voltage required to obtain a certain luminance is low and power consumption is also low in the case of the light-emitting element 1.

Accordingly, it was found that with the use of the triarylamine compound, which can be synthesized using the halogenated diarylamine compound of one embodiment of the present invention, capable of being driven at low voltage. Moreover, it was confirmed that a light-emitting element which has high efficiency and low power consumption and is able to be driven at a low voltage can be provided.

Figure 19:
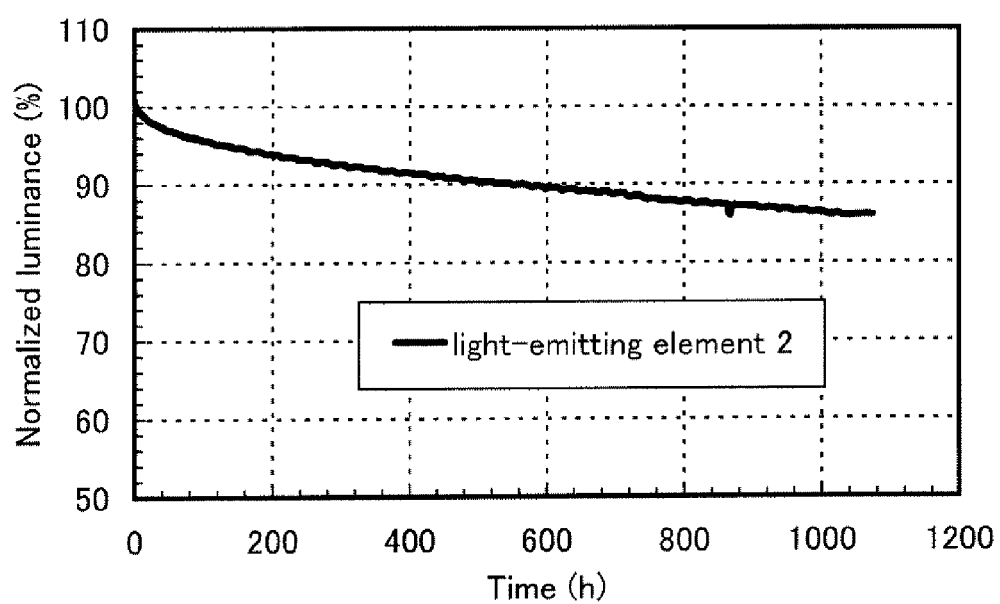
FIG. 19 is a graph showing time-normalized luminance characteristics of the light-emitting element 2.

Next, a reliability test of the light-emitting element 2 was carried out. Results of the reliability test are shown in FIG. 19. In FIG. 19, the vertical axis represents normalized luminance (%) on the assumption that an initial luminance is 100%, and the horizontal axis represents driving time (h) of the light-emitting element. The reliability test was carried out by driving the light-emitting element 2 of this example at a constant current density under the conditions that an initial luminance was set at 1000 cd/m$^2$. FIG. 19 shows that the light-emitting element 1 keeps 86% of the initial luminance after the driving for 1000 hours. Therefore, it was confirmed that the light-emitting element 2 is indicative of high reliability. Thus, it was found that with the use of the triarylamine compound of one embodiment of the present invention, a light-emitting element with long lifetime can be obtained.

Example 8

In an aromatic ring that has an electron-donating group such as amine and a high electron density, hydrogen can be directly substituted by halogen. For example, aniline acts with N-bromosuccinimide (abbreviation: NBS) that is a halogenating agent in the presence of ethyl acetate that is a polar solvent, the para position can be directly brominated. On the other hand, in the case where a substrate that does not have a high electron density such as benzene or fluorene is halogenated, a catalyst such as iron salt or acid is added thereto.

In the diarylamine compound represented by the general formula (G0), one of positions which is likely to be halogenated (para positions of phenylamine) is occupied by a substituent (Ar or α) which is not likely to be halogenated as compared with the position. Accordingly, bromide of the general formula (G0) which is a compound represented by the following general formula (G1-Br) can be efficiently obtained. Therefore, in the case where bromine is attached in the reaction of NBS and the diarylamine compound represented by the general formula (G0), it is considered that the following reaction occurs.

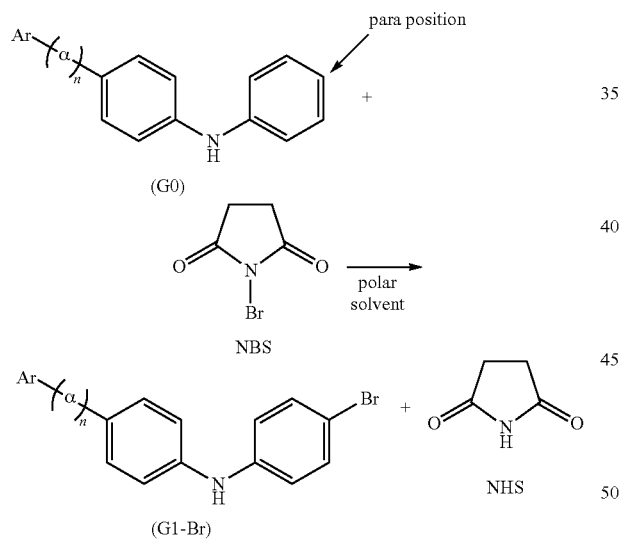

This reaction is electrophilic substitution; therefore, it is considered that hindrance is hardly generated and bromine easily attaches to a position with a large number of electrons (the fourth position of phenylamine, the para position denoted by the arrow).

In this example, the most stable structures in the singlet state of the diarylamine compound represented by the general formula (G0) and NBS were calculated depending on the density functional theory. The diarylamine compound represented by the general formula (G0) is used as a source material for synthesis of one embodiment of the halogenated diarylamine compound, which is one embodiment of the present invention and represented by the general formula (G1) described in Embodiment 1. The quantum chemistry computational program used here is Gaussian 03. As a basis function, 6-311G (d, p) was adopted. As a functional, B3LYP was used. Since the reaction occurs in a polar solvent such as ethyl acetate, acetic acid, or dichloromethane, solvent effect was considered as calculation conditions by a PCM method (polarizable continuum model). In this calculation, dichloromethane was employed. In addition, the number of electrons in the highest occupied molecular orbital (abbreviation: HOMO) of the structure and the number of electrons in the lowest unoccupied molecular orbital (abbreviation: LUMO) of NBS were calculated on the basis of the following formula.

$$\Psi_{HOMO} = \sum_r c_{HOMO,r} \phi_r$$

$$N_r = 2 \sum_{s=1}^{N} c_{HOMO,r} c_{HOMO,s} S_{rs}$$

$$N_A = \sum_r^{onA} N_r$$

Here, $\Psi_{HOMO}$ is the highest occupied molecular orbital, $\phi_r$, is the rth atomic orbital, $C_{HOMO,\ r}$ is a coefficient of the rth atomic orbital in the highest occupied molecular orbital, N is the number of doubly occupied orbitals, and $N_A$ is the number of electrons in HOMO of an atom A.

The calculation on the number of electrons in HOMO was curried out in the case where any one of the following substituents (Ar-1) to (Ar-3), (Ar-5) to (Ar-8), (Ar-9) to (Ar-11), and (Ar-13) to (Ar-15) corresponds to aryl (Ar) in the following general formulae (300) and (301).

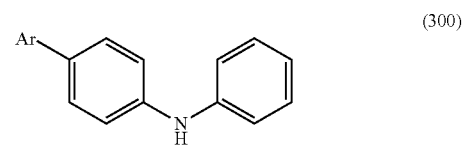

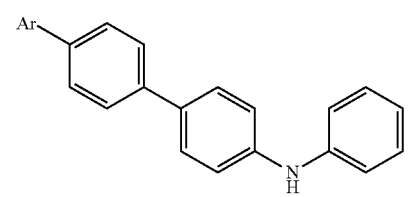

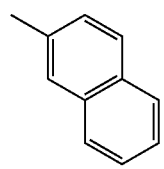

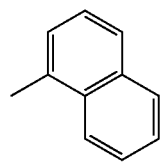

-continued (Ar-3)

(Ar-5)

(Ar-6)

(Ar-7)

(Ar-8)

(Ar-9)

(Ar-10)

(Ar-11)

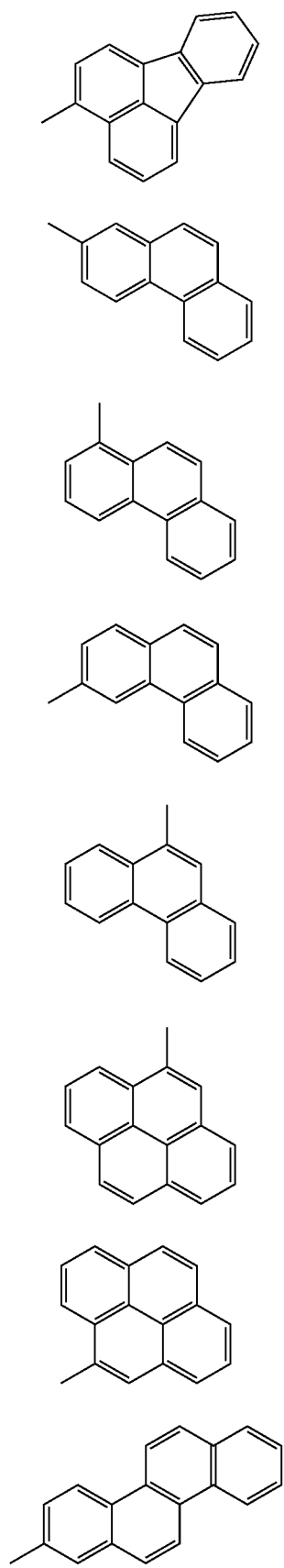

-continued

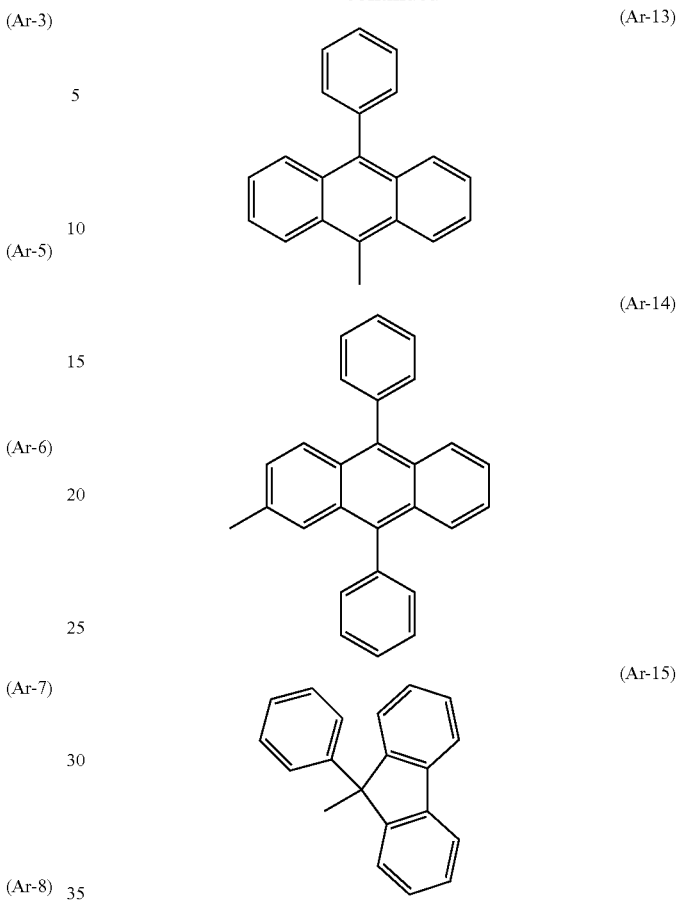

Figure 20A:
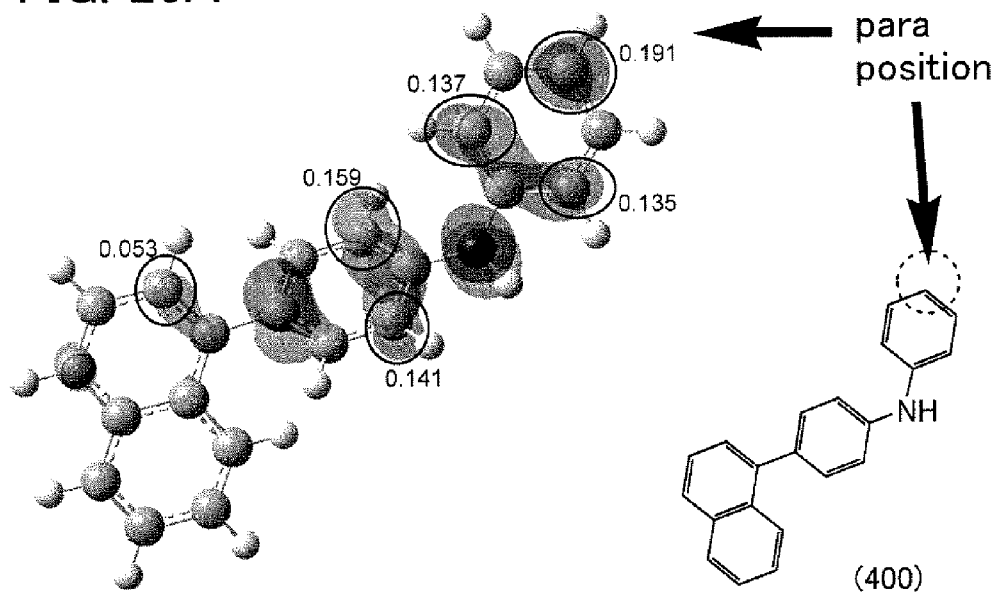
FIGS. 20A and 20B are diagrams illustrating the highest occupied molecular orbitals (HOMO) of structural formulae (400) and (401), respectively.
Figure 20B:
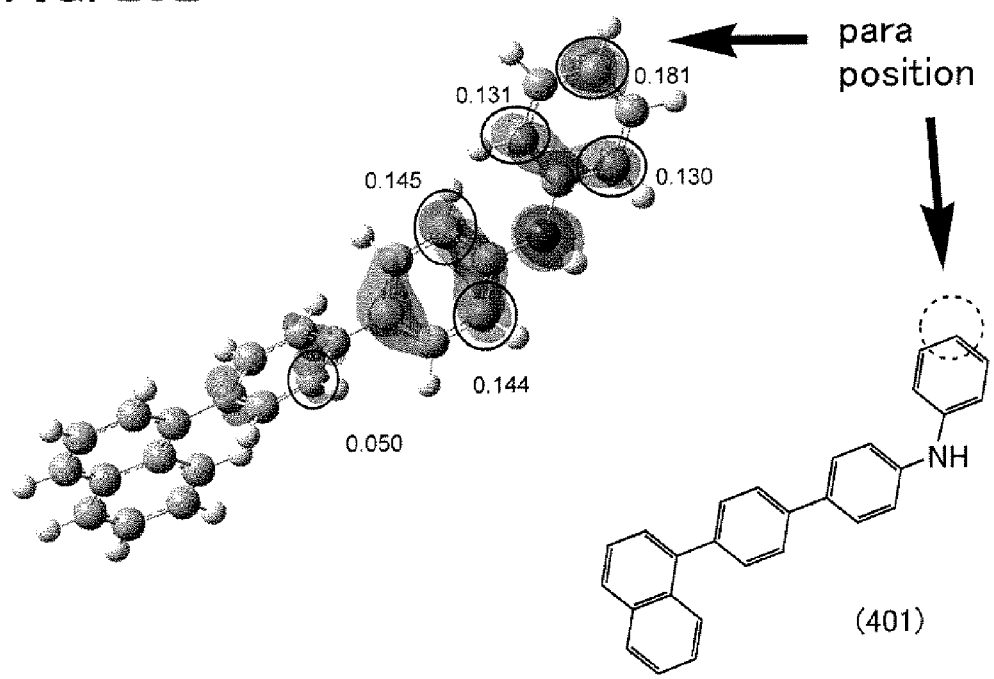

The calculation results (electron distribution in HOMO) in the case where an aryl group (Ar) in each of the general formulae (300) and (301) is 1-naphthyl (Ar-2) are shown in FIGS. 20A and 20B, respectively.

Figure 21A:
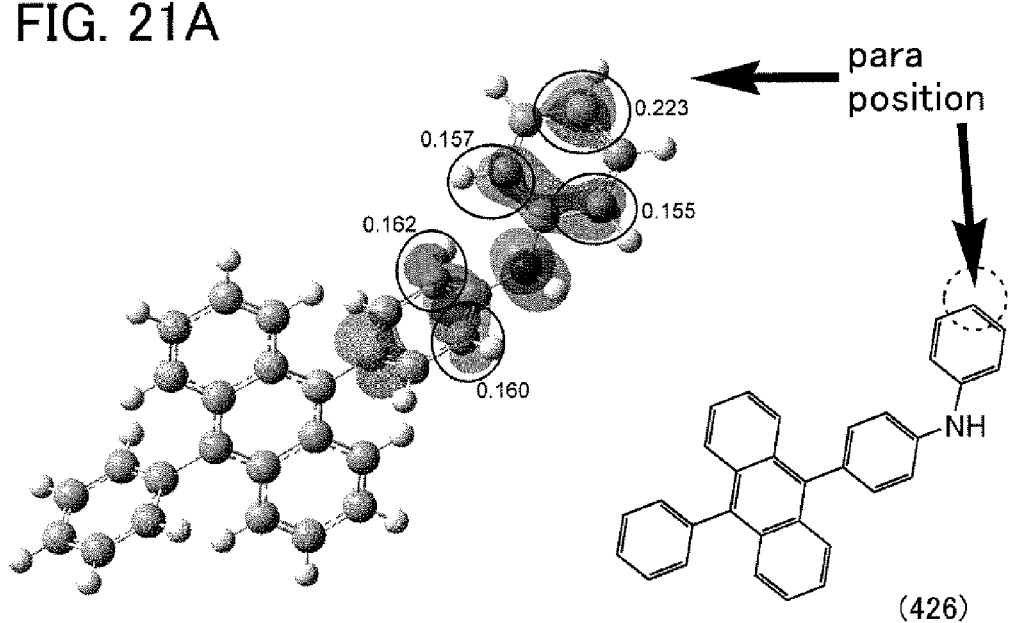
Figure 21B:
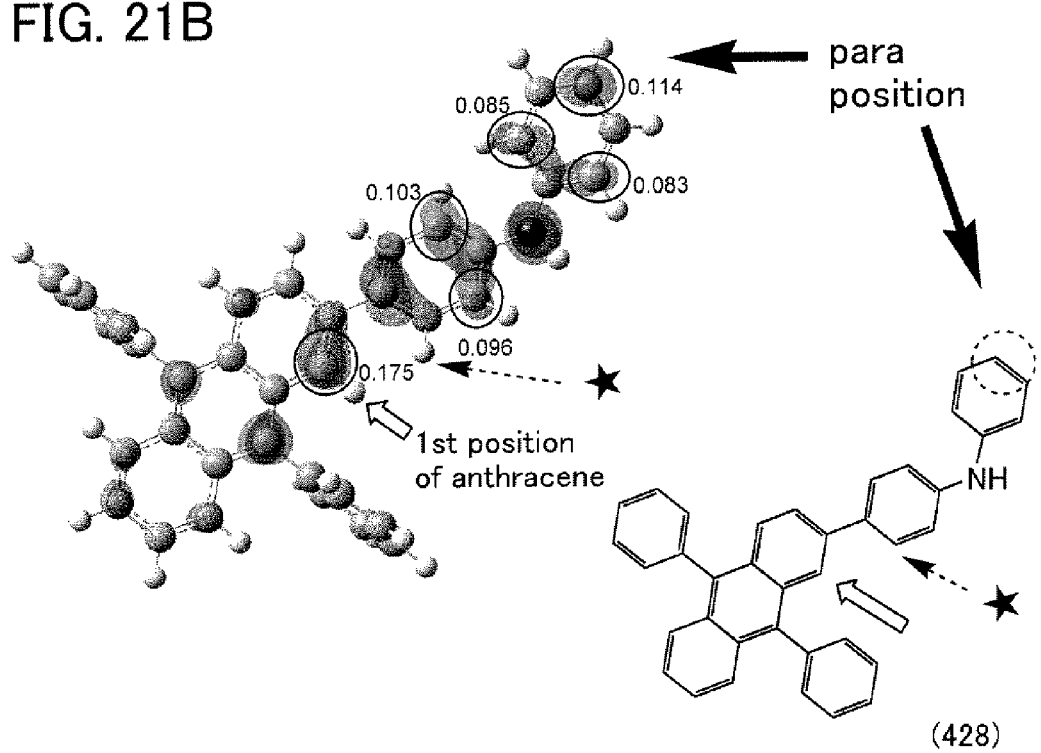
Figure 22:
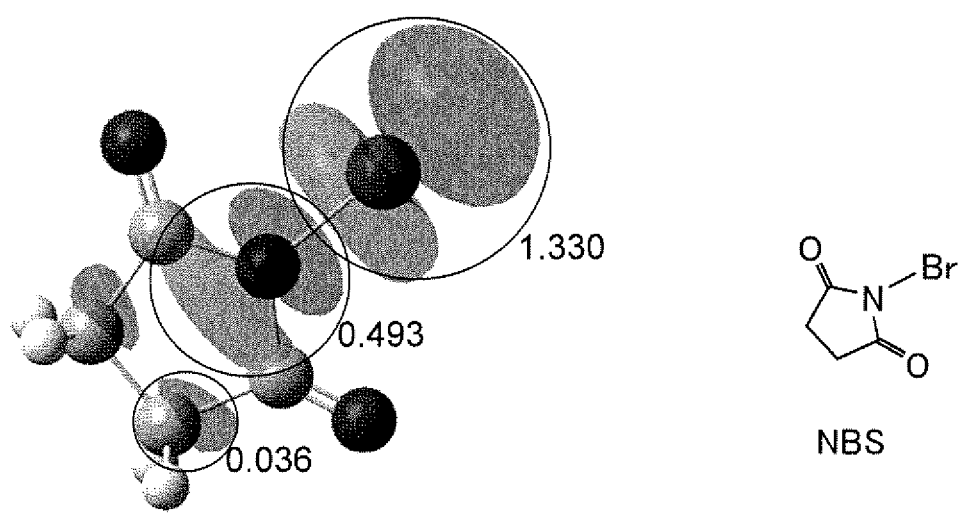
FIG. 22 is a diagram illustrating the lowest unoccupied molecular orbital (LUMO) of N-bromosuccinimide (NBS)

The calculation result (electron distribution in HOMO) in the case where Ar in the general formula (300) is 9-(10-phenylanthryl) (Ar-13) is shown in FIG. 21A, and the calculation result in the case where Ar in the general formula (300) is 2-(9,10-diphenyl)anthryl (Ar-14) is shown in FIG. 21B. The calculation result of NBS (electron distribution in LUMO) is shown in FIG. 22.

FIGS. 20A and 20B are drawings illustrating electron diffusion and numerals therein denote the number of electrons. The sum of the numerals with respect to all atoms is 2. Accordingly, the number of electrons (0.191 in FIG. 20A, 0.181 in FIG. 20B) in the para position (the fourth position of phenylamine denoted by the arrow) is the largest; thus, it is understood that bromine is most likely to attach to the para position. It is considered that bromine hardly attaches to other carbon divisions in arylphenylamine with a large number of electrons since steric hindrance is large.

Similarly, FIGS. 21A and 21B are drawings illustrating electron diffusion and numerals therein denote the number of electrons. The sum of the numerals with respect to all atoms is 2.

According to FIG. 21A, the number of electrons (0.223) in the para position (the fourth position of phenylamine denoted by the arrow) is the largest; thus, it is understood that bromine is most likely to attach to the para position. It is considered that bromine hardly attaches to other carbon divisions in arylphenylamine with a large number of electrons since steric hindrance is large.

The ninth and tenth positions of anthracene are likely to be oxidized (halogenated); thus, it is preferable that the ninth and tenth positions be capped by a phenyl group or the like in advance, in this manner. Accordingly, a desired position (the fourth position of phenylamine denoted by the arrow) is preferentially halogenated when halogenation reaction is carried out. Similarly, it is preferable that positions which are likely to be oxidized in the other aryl groups be capped in advance.

According to FIG. 21B, the number of electrons (0.175) in the first position of an anthryl group is the largest, followed by the number of electrons (0.114) in the para position (the fourth position of phenylamine). However, it is considered that bromine hardly attaches to the first position of the anthryl group. This is because there is a large steric hindrance between a phenylene group bonded to the anthryl group and hydrogen in the ortho position (denoted by a star mark) with respect to the anthryl group.

According to the other calculations on arylphenylamine, the number of electrons is largest in the para position (the fourth position of phenylamine), similarly. It is considered that bromine hardly attaches to other carbon divisions in arylphenylamine with a large number of electrons since steric hindrance is large.

FIG. 22 illustrates LUMO of NBS. The number of electrons of bromine is 1.330, which is the largest. This means that an electron is likely to enter the position of bromine. It was also found that bonding between nitrogen and bromine is easily broken since it is an antibonding orbital.

The calculation on the number of electrons in HOMO was curried out in the case where the above-mentioned substituent (Ar-2) corresponds to aryl (Ar) in the following general formulae (302) and (303).

Figure 23A:
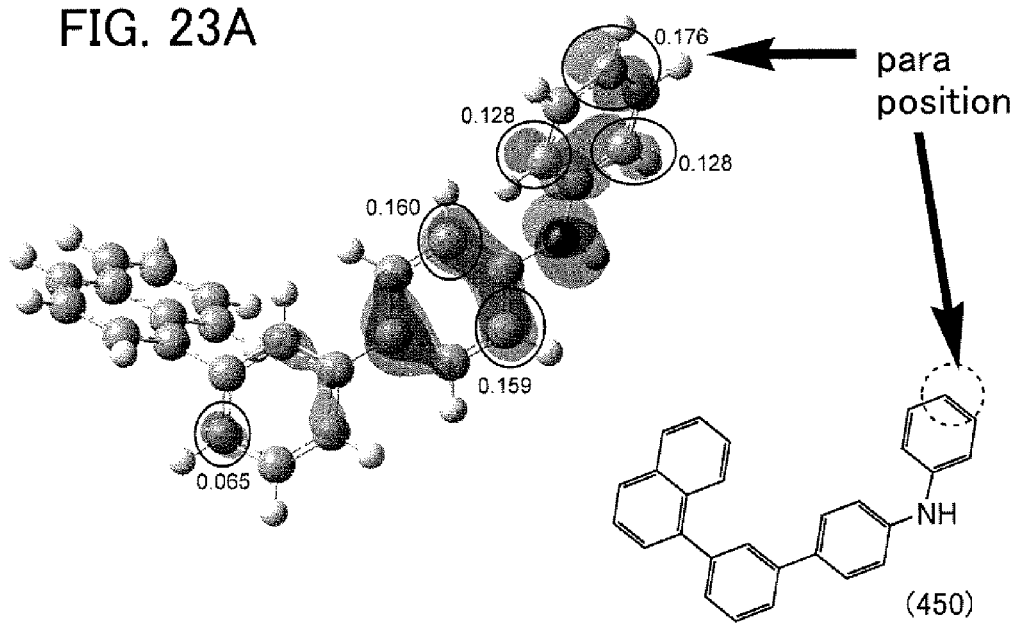
FIGS. 23A and 23B are diagrams illustrating the highest occupied molecular orbitals (HOMO) of structural formulae (450) and (451), respectively.
Figure 23B:
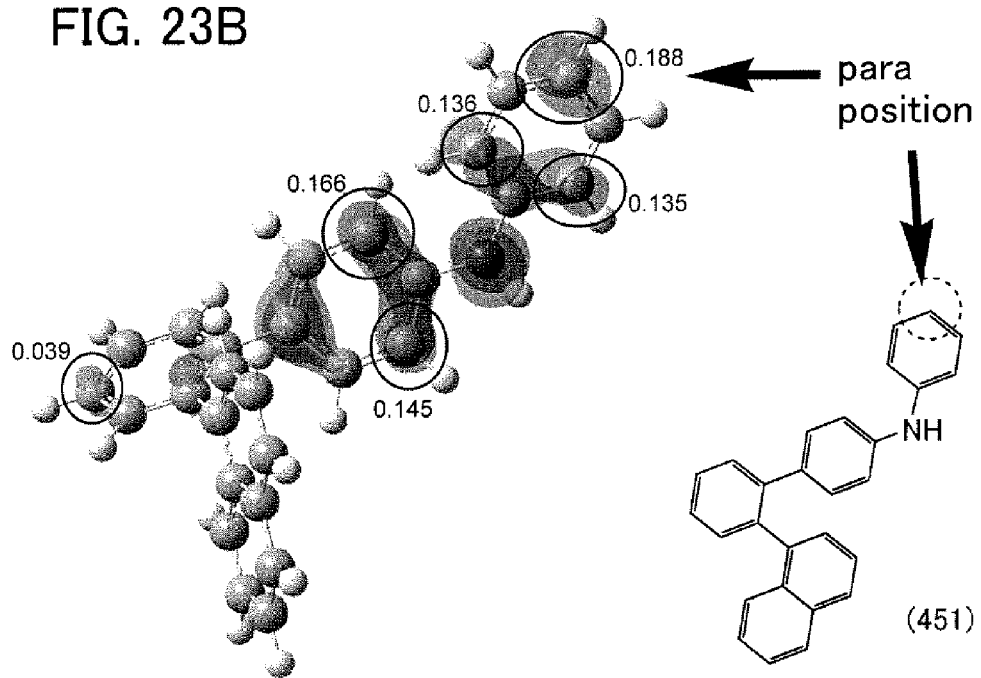

The calculation results (electron diffusion in HOMO) are shown in FIGS. 23A and 23B.

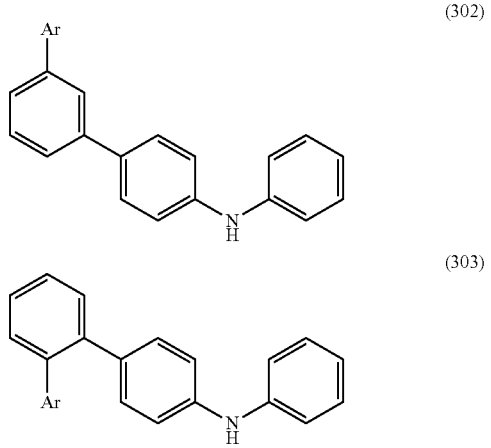

According to both FIGS. 23A and 23B, the number of electrons (0.176 in FIG. 23A, 0.188 in FIG. 23B) in the para position (the fourth position of phenylamine denoted by the arrow) is the largest; thus, it is understood that bromine is most likely to attach to the para position. It is considered that bromine hardly attaches to other carbon divisions in arylphenylamine with a large number of electrons since steric hindrance is large.

As described above, it is considered that a reaction where bromine attaches to the para position (the fourth position of phenylamine) of the diarylamine compound represented by the general formula (G0) is likely to occur. The same assumption can be applied to the case of other halogen (iodine or chlorine) since it reacts in the same reaction mechanism. That is, as shown in the following formulae, when a halogenating agent acts with the arylphenylamine compound represented by the general formula (G0) in a polar atmosphere, the halogenated arylamine compound, which is one embodiment of the present invention and represented by the following general formula (G1) can be selectively and efficiently synthesized.

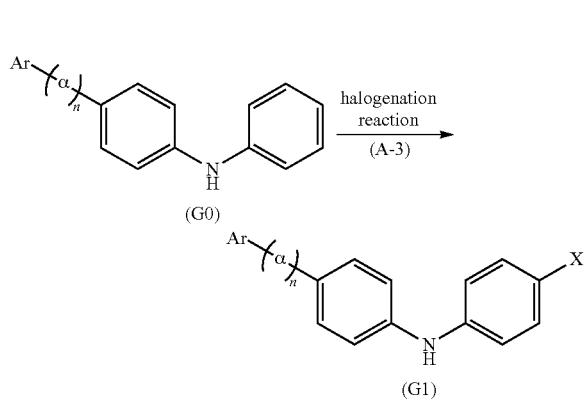

Note that in the general formulae in Example 8, Ar represents any of substituted or unsubstituted polycyclic aromatic hydrocarbon groups having 2 to 6 rings, α represents a substituted or unsubstituted phenylene group, and n represents 0 or 1. Further, X represents any of chlorine, bromine, and iodine. Furthermore, $E^1$ and $E^2$ independently represent an aryl group and the aryl group includes a heteroaryl group.

This application is based on Japanese Patent Application serial no. 2009-218290 filed with Japan Patent Office on Sep. 22, 2009, the entire contents of which are hereby incorporated by reference.

What is claimed is:

1. A halogenated diarylamine compound represented by a general formula (G1),

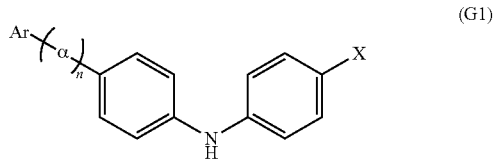

wherein in the general formula (G1), Ar represents any of substituted or unsubstituted polycyclic aromatic hydrocarbon groups having 2 to 6 rings, wherein α represents a substituted or unsubstituted phenylene group, wherein n represents 0 or 1; and wherein X represents chlorine, bromine, or iodine.

2. The halogenated diarylamine compound according to claim 1, wherein Ar in the general formula (G1) is any one of a substituted or unsubstituted naphthyl group, a substituted or unsubstituted fluoranthenyl group, a substituted or unsubstituted fluorenyl group, a substituted or unsubstituted 9,9'-spirofluorenyl group, a substituted or unsubstituted phenanthryl group, a substituted or unsubstituted pyrenyl group, a substituted or unsubstituted triphenylenyl group, a substituted or unsubstituted chrysenyl group, a substituted or unsubstituted anthryl group, a substituted or unsubstituted pentacenyl group, and a substituted or unsubstituted tetracenyl group.
3. The halogenated diarylamine compound according to claim 1,
wherein Ar in the general formula (G1) is represented by any one of the structural formulae (Ar-1) to (Ar-17),
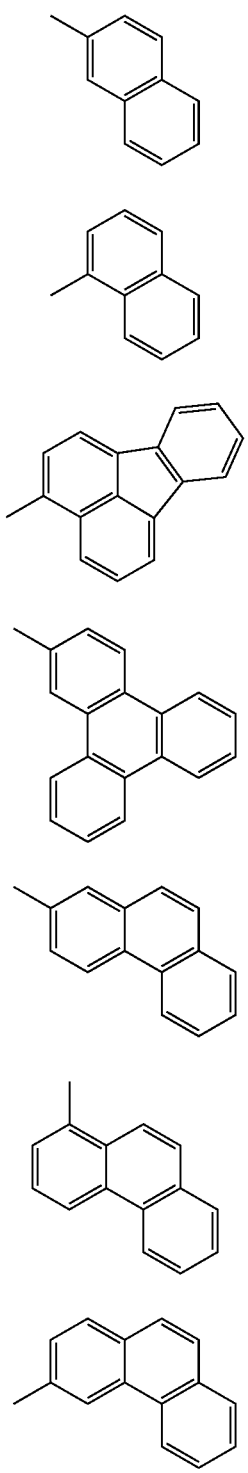
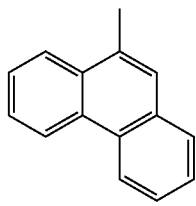
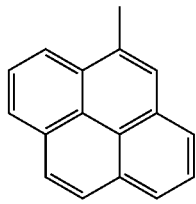
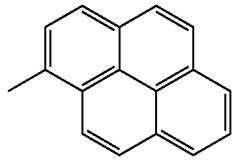
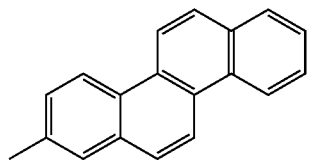
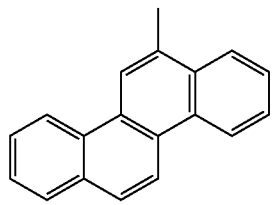
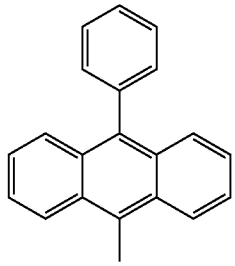
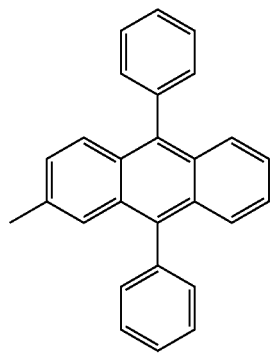

(Ar-15)

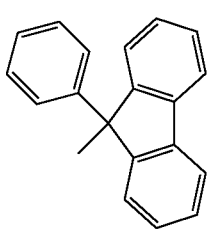

(Ar-16)

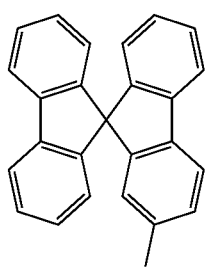

(Ar-17)

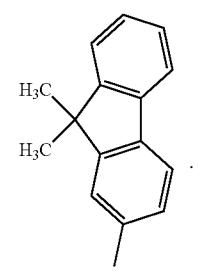

4. The halogenated diarylamine compound according to claim 1,
wherein α in the general formula (G1) corresponds to any one of structural formulae (α-1) to (α-3), (α-1)

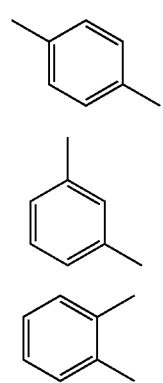

(α-2)

(α-3)

5. The halogenated diarylamine compound according to claim 1,
wherein a substituent of Ar and a substituent of α in the general formula (G1) are each independently any one of an alkyl group having 1 to 6 carbon atoms and an aryl group having 6 to 12 carbon atoms.

6. The halogenated diarylamine compound according to claim 1,
wherein a substituent of Ar and a substituent of α in the general formula (G1) are each independently represented by any one of structural formulae (R-1) to (R-8), (R-1)
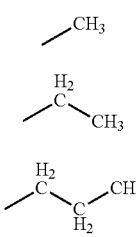

(R-2)
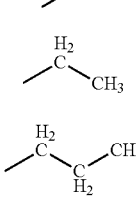

(R-3)
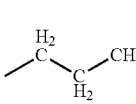

(R-4)
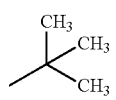

(R-5)
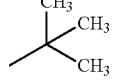

(R-6)
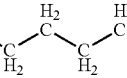

(R-7)
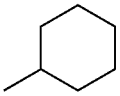

(R-8)
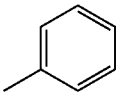

7. A halogenated diarylamine compound represented by a structural formula (100), (100)
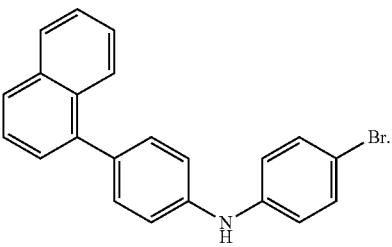

8. A halogenated diarylamine compound represented by a structural formula (126), (126)
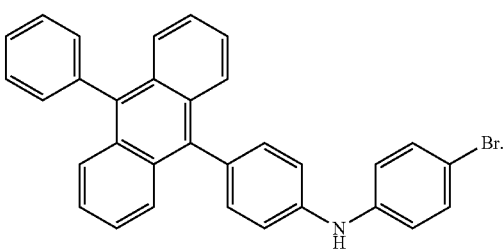

9. A synthesis method of a halogenated diarylamine compound represented by a general formula (G1), comprising the step of halogenating a diarylamine compound represented by a general formula (G0) to synthesize a halogenated diarylamine compound represented by the general formula (G1),

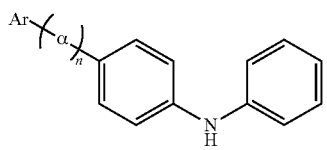
(G0)

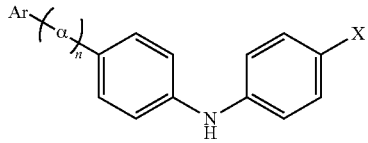
(G1)

wherein in the general formula (G0), Ar represents any of substituted or unsubstituted polycyclic aromatic hydrocarbon groups having 2 to 6 rings, α represents a substituted or unsubstituted phenylene group, and n represents 0 or 1; and wherein in the general formula (G1), Ar represents any of substituted or unsubstituted polycyclic aromatic hydrocarbon groups having 2 to 6 rings, α represents a substituted or unsubstituted phenylene group, n represents 0 or 1, and X represents chlorine, bromine, or iodine.

* * * * *

UNITED STATES PATENT AND TRADEMARK OFFICE
CERTIFICATE OF CORRECTION

PATENT NO.         : 8,729,310 B2
APPLICATION NO.    : 12/885698
DATED              : May 20, 2014
INVENTOR(S)        : Osaka et al.

It is certified that error appears in the above-identified patent and that said Letters Patent is hereby corrected as shown below:

In the Specification

Column 8, line 1, "NMR" should read --$^1$H NMR--.

Column 8, line 18, "element" should read --element 1;--.

Column 8, lines 18-20, should read --FIG. 14 is a graph showing time-normalized luminance characteristics of the light-emitting element 1;--.

Column 8, line 34, "2113" should read --21B--.

Column 9, line 26, "a represents" should read --α represents--.

Column 14, line 58, "a represents" should read --α represents--.

Column 15, line 38, "particular." should read --particular,--.

Column 15, line 65, "a represents" should read --α represents--.

Column 16, line 52, "a represents" should read --α represents--.

Column 38, line 57, "E' can" should read --Ar and E$^1$ can--.

Column 38, line 60, "E' can" should read --Ar and E$^1$ can--.

Column 57, line 56, "803" should read --8.03--.

Column 60, line 62, "Co., Ltd.)" should read --Co., Ltd.,)--.

Column 61, line 1, "Inc., was" should read --Inc.,) was--.

Column 61, line 19, "(vs. Ag/Ae)" should read --(vs. Ag/Ag$^+$)--.

Column 67, line 51, "μm/W" should read --lm/W--.

Column 70, line 25, "ϕ$_r$," should read --ϕ$_r$--.

Signed and Sealed this
Sixteenth Day of December, 2014

Michelle K. Lee
*Deputy Director of the United States Patent and Trademark Office*